(12) United States Patent
Kong et al.

(10) Patent No.: US 12,215,149 B2
(45) Date of Patent: Feb. 4, 2025

(54) ANTI-MS4A6A ANTIBODIES AND METHODS OF USE THEREOF

(71) Applicant: Alector LLC, South San Francisco, CA (US)

(72) Inventors: Philip Kong, San Francisco, CA (US); Herve Rhinn, San Francisco, CA (US); Tina Schwabe, San Francisco, CA (US); Angie Yee, San Francisco, CA (US); Arnon Rosenthal, Woodside, CA (US)

(73) Assignee: Alector LLC, South San Francisco, CA (US)

( * ) Notice: Subject to any disclaimer, the term of this patent is extended or adjusted under 35 U.S.C. 154(b) by 142 days.

(21) Appl. No.: 17/722,624

(22) Filed: Apr. 18, 2022

(65) Prior Publication Data
US 2022/0380455 A1     Dec. 1, 2022

Related U.S. Application Data

(63) Continuation of application No. 16/965,675, filed as application No. PCT/US2019/016141 on Jan. 31, 2019, now abandoned.

(60) Provisional application No. 62/624,578, filed on Jan. 31, 2018, provisional application No. 62/646,846, filed on Mar. 22, 2018.

(51) Int. Cl.
| | |
|---|---|
| *C07K 16/18* | (2006.01) |
| *A61K 39/00* | (2006.01) |
| *A61P 25/28* | (2006.01) |
| *C07K 16/28* | (2006.01) |

(52) U.S. Cl.
CPC .............. *C07K 16/28* (2013.01); *A61P 25/28* (2018.01); *A61K 2039/505* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 9,969,799 B2 | 5/2018 | Wang et al. | |
| 11,472,874 B2 | 10/2022 | Kong et al. | |

(Continued)

FOREIGN PATENT DOCUMENTS

| | | |
|---|---|---|
| CN | 101001879 A | 7/2007 |
| CN | 101998992 A | 3/2011 |

(Continued)

OTHER PUBLICATIONS

Edwards et al., The remarkable flexibility of the human antibody repertoire; isolation of over one thousand different antibodies to a single protein, BLyS. J Mol Biol. Nov. 14, 2003;334(1):103-18. (Year: 2003).*

(Continued)

*Primary Examiner* — Aurora M Fontainhas
(74) *Attorney, Agent, or Firm* — Sterne, Kessler, Goldstein & Fox P.L.L.C.

(57) ABSTRACT

The present disclosure is generally directed to compositions that include antibodies, e.g., monoclonal, antibodies, antibody fragments, etc., that specifically bind a MS4A6A polypeptide, e.g., a mammalian MS4A6A or human MS4A6A, and use of such compositions in preventing, reducing risk, or treating an individual in need thereof.

19 Claims, 3 Drawing Sheets

Specification includes a Sequence Listing.

(56) References Cited

U.S. PATENT DOCUMENTS

| | | | |
|---|---|---|---|
| 11,667,699 | B2 | 6/2023 | Sun et al. |
| 2009/0011409 | A1 | 1/2009 | Sharma et al. |
| 2011/0027297 | A1 | 2/2011 | Sahin et al. |
| 2016/0376359 | A1 | 12/2016 | Wang et al. |
| 2017/0355756 | A1 | 12/2017 | Julien et al. |
| 2021/0040200 | A1 | 2/2021 | Kong et al. |
| 2021/0079074 | A1 | 3/2021 | Sun et al. |
| 2021/0122817 | A1 | 4/2021 | Kong et al. |
| 2023/0126400 | A1 | 4/2023 | Kong et al. |
| 2024/0076362 | A1 | 3/2024 | Sun et al. |

FOREIGN PATENT DOCUMENTS

| | | |
|---|---|---|
| CN | 105759057 A | 7/2016 |
| CN | 105969901 A | 9/2016 |
| WO | WO-2002062946 A2 | 8/2002 |
| WO | WO-2003035689 A1 | 5/2003 |
| WO | WO-2005040796 A1 | 5/2005 |
| WO | WO-2005123779 A2 | 12/2005 |
| WO | WO-2008068048 A2 | 6/2008 |
| WO | WO-2011147851 A1 | 12/2011 |
| WO | WO-2017143036 A1 | 8/2017 |
| WO | WO-2019152706 A1 | 8/2019 |
| WO | WO-2019152715 A1 | 8/2019 |
| WO | WO-2020160468 A1 | 8/2020 |
| WO | WO-2021022083 A2 | 2/2021 |
| WO | WO-2021081101 A1 | 4/2021 |
| WO | WO-2024086796 A1 | 4/2024 |

OTHER PUBLICATIONS

Allen, M., et al., "Novel late-onset Alzheimer disease loci variants associate with brain gene expression," Neurology 79(3):221-228, Lippincott Williams and Wilkins Ltd., United States (Jul. 2012).

Antúnez, C., et al., "The membrane-spanning 4-domains, subfamily A (MS4A) gene cluster contains a common variant associated with Alzheimer's disease," Genome Medicine 3:33, BioMed Central Ltd., United Kingdom (May 2011).

Arnett, M.J., et al., "Pro-NGF, Sortilin, and p75$^{NTR}$: Potential Mediators of Injury-induced Apoptosis in the Mouse Dorsal Root Ganglion," Brain Research 1183:32-42, Elsevier, Netherland (Dec. 2007).

Barber, R.C., "The Genetics of Alzheimer's Disease," Scientifica (Cairo) 2012:246210, 14 pages, Hindawi Publishing Corporation, Egypt (Dec. 2012).

Beattie, M.S., et al., "ProNGF Induces p75-mediated Death of Oligodendrocytes Following Spinal Cord Injury," Neuron 36(3):375-386, Cell Press, United States (Oct. 2002).

Bubien, J.K., et al., "Transfection of the CD20 Cell Surface Molecule Into Ectopic Cell Types Generates a Ca2+ Conductance Found Constitutively in B Lymphocytes," The Journal of Cell Biology 121(5):1121-1132, Rockefeller University Press, United States (Jun. 1993).

Cruse, G., et al., "The CD20 Homologue MS4A4 Directs Trafficking of KIT Toward Clathrin-independent Endocytosis Pathways and Thus Regulates Receptor Signaling and Recycling," Molecular Biology of the Cell 26(9):1711-1727, American Society for Cell Biology, United States (May 2015).

Efthymiou, A.G., and Goate A.M., "Late Onset Alzheimer's Disease Genetics Implicates Microglial Pathways in Disease Risk," Molecular Neurodegeneration 12:43, BioMed Central Ltd., United Kingdom (May 2017).

Elias-Sonnenschein, L.S., et al., "Genetic loci associated with Alzheimer's disease and cerebrospinal fluid biomarkers in a Finnish case-control cohort," PLoS One 8(4):e59676, Public Library of Science, United States (Apr. 2013).

Fahnestock, M., et al., "The Precursor Pro-nerve Growth Factor is the Predominant Form of Nerve Growth Factor in Brain and is Increased in Alzheimer's Disease," Molecular and Cellular Neurosciences 18(2):210-220, Academic Press, United States (Aug. 2001).

Fan, Y.J., et al., "Differential Effects of Pro-BDNF on Sensory Neurons After Sciatic Nerve Transection in Neonatal Rats," European Journal of Neuroscience 27(9):2380-2390, Wiley-Blackwell, France (May 2008).

Greer, P.L., et al., "A Family of Non-GPCR Chemosensors Defines an Alternative Logic for Mammalian Olfaction," Cell 165(7):1734-1748, MIT Press, United States (Jun. 2016).

Harrington, A.W., et al., "Secreted ProNGF is a Pathophysiological Deat-inducing Ligand After Adult CNS Injury," Proceedings of the National Academy of Sciences of the United States of America 101(16):6226-6230, National Academy of Sciences, United States (Apr. 2004).

Hollingworth, P., et al., "Common Variants at ABCA7, MS4A6AIMS4A4E, EPHA1, CD33 and CD2AP Are Associated With Alzheimer's Disease," Nature Genetics 43(5):429-435, Nature Publishing Group, United Kingdom (May 2011).

Hu, X., et al., "Genome-wide association study identifies multiple novel loci associated with disease progression in subjects with mild cognitive impairment," Transl Psychiatry 1:e54, Macmillan Publishers Ltd., United Kingdom (Aug. 2011).

International Search Report and Written Opinion for International Application No. PCT/US2019/016141, Korean Intellectual Property Office, Korea, mailed on May 30, 2019, 11 pages.

Ishibashi, K., et al., "Identification of a New Multigene Four-transmembrane Family (MS4A) Related to CD20, HTm4 and β Subunit of the High-affinity IgE Receptor," Gene 264(1):87-93, Elsevier, Netherlands (Feb. 2001).

Jansen, P., et al., "Roles for the Pro-neurotrophin Receptor Sortilin in Neuronal Development, Aging and Brain Injury," Nature Neuroscience 10(11):1449-1457, Nature America Inc., United States (Nov. 2007).

Karch, C.M., et al., "Expression of novel Alzheimer's disease risk genes in control and Alzheimer's disease brains," PLoS One 7(11):e50976, Public Library of Science, United States (Nov. 2012).

Karch, C.M., et al., "Alzheimer's disease risk genes and mechanisms of disease pathogenesis," Biol Psychiatry 77(1):43-51, Elsevier Inc., Netherlands (Jan. 2015).

Kay, B.K., et al., "The Importance of Being Proline: the Interaction of Proline-rich Motifs in Signaling Proteins With Their Cognate Domains," FASEB 14(2):231-241, The Federation of American Societies for Experimental Biology, United States (Feb. 2000).

Koslowski, M., et al., "MS4A12 is a Colon-selective Store-operated Calcium Channel Promoting Malignant Cell Processes," Cancer Research 68(9):3458-3466, American Association for Cancer Research, United States (May 2008).

Lacher, S.E., et al., "A Hypermorphic Antioxidant Response Element is Associated With Increased MS4A6A Expression and Alzheimer's Disease," Redox Biology 14:686-693, Elsevier B.V., Netherlands (Apr. 2018).

Lambert, J.C., et al., "Meta-analysis of 74,046 Individuals Identifies 11 New Susceptibility Loci for Alzheimer's Disease," Nature Genetics 45(12):1452-1458, Nature Publishing Group, United Kingdom (Dec. 2013).

Liang, C.C., et al., "In Vitro Scratch Assay: a Convenient and Inexpensive Method for Analysis of Cell Migration in Vitro," Nature Protocols 2(2):329-333, Nature Publishing Group, United Kingdom (2007).

Liang, Y., and Tedder, T.F., "Identification of a CD20-, FcεRIβ-, and HTm4-related Gene Family: Sixteen New MS4A Family Members Expressed in Human and Mouse," Genomics 72(2):119-127, Academic Press, United States (Mar. 2001).

Ma, J., et al., "MS4A Cluster in Alzheimer's Disease," Molecular Neurobiology 51(3):1240-1248, Humana Press, United States (2015).

Ma, J., et al., "MS4A6A genotypes are associated with the atrophy rates of Alzheimer's disease related brain structures," Oncotarget 7(37):58779-58788, Impact Journals LLC, United States (Sep. 2016).

Maximov, A., et al., "Monitoring Synaptic Transmission In Primary Neuronal Cultures Using Local Extracellular Stimulation," Journal of Neuroscience Methods 161(1):75-87, Elsevier/North-Holland Biomedical Press, Netherlands (Mar. 2007).

(56) References Cited

OTHER PUBLICATIONS

Naj, A.C., et al., "Common Variants at MS4A4/MS4A6E, CD2AP, CD33 and EPHA1 Are Associated With Late-onset Alzheimer's Disease," *Nature Genetics* 43(5):436-441, Nature Publishing Group, United Kingdom (May 2011).

Nakamura, K., et al., "Intracellular Sortilin Expression Pattern Regulates ProNGF-induced Naturally Occurring Cell Death During Development," *Cell Death and Differentiation* 14(8):1552-1554, Edward Arnold, United Kingdom (Aug. 2007).

Nykjaer, A., et al., "Sortilin is Essential for ProNGF-induced Neuronal Cell Death," *Nature* 427(6977):843-848, Macmillan Journals, United Kingdom (Feb. 2004).

Nykjaer, A., et al., "p75$^{NTR}$—Live or Let Die," *Current Opinion in Neurobiology* 15(1):49-57, Current Biology, United Kingdom (Feb. 2005).

Proitsi, P., et al. "Alzheimer's disease susceptibility variants in the MS4A6A gene are associated with altered levels of MS4A6A expression in blood," *Neurobiology of Aging* 35(2):279-290, Elsevier, Netherlands (2014).

Provenzano, M.J., et al., "p75$^{NTR}$ and Sortilin Increase After Facial Nerve Injury," *Laryngoscope* 118(1):87-93, Wiley-Blackwell, United States (Jan. 2008).

Shawi, R.A., et al., "Neurotoxic and Neurotrophic Roles of ProNGF and the Receptor Sortilin in the Adult and Ageing Nervous System," *European Journal of Neuroscience* 28(9):2103-2114, Wiley-Blackwell Publishing Ltd., United Kingdom (Dec. 2008).

Teng, H.K., et al., "ProBDNF Induces Neuronal Apoptosis via Activation of a Receptor Complex of p75$^{NTR}$ and Sortilin," *The Journal of Neuroscience* 25(22):5455-5463, Society for Neuroscience, United States (Jun. 2005).

Volosin, M., et al., "Induction of Proneurotrophins and Activation of p75$^{NTR}$-mediated Apoptosis via Neurotrophin Receptor-interacting Factor in Hippocampal Neurons After Seizures," *The Journal of Neuroscience* 28(39):9870-9879, Society for Neuroscience, Unites States (Sep. 2008).

Volosin, M., et al., "Interaction of Survival and Death Signaling in Basal Forebrain Neurons: Roles of Neurotrophins and Proneurotrophins," *The Journal of Neuroscience* 26(29):7756-7766, Society for Neuroscience, United States (Jul. 2006).

Wei, Y., et al., "Enhanced Protein Expressions of Sortilin and p75$^{NTR}$ in Retina of Rat Following Elevated Intraocular Pressure-induced Retinal Ischemia," *Neuroscience Letters* 429(2-3):169-174, Elsevier, Ireland (Dec. 2007).

Yano, H., et al., "Proneurotrophin-3 Is a Neuronal Apoptotic Ligand:Evidence for Retrograde-Directed Cell Killing," *The Journal of Neuroscience* 29(47):14790-14802, Society for Neuroscience, United States (Nov. 2009).

Chen, C., et al., "Enhancement and destruction of antibody function by somatic mutation: unequal occurrence is controlled by V gene combinatorial associations," EMBO Journal 14(12):2784-2794, Oxford University Press, United Kingdom (1995).

Deming, Y., et al., "The MS4A gene cluster is a key regulator of soluble TREM2 and Alzheimer disease risk," *Science Translational Medicine* 11(505):2291, 18 pages, American Association for the Advancement of Science, United States (Aug. 2019).

Denardo, D.G., et al., "Leukocyte Complexity Predicts Breast Cancer Survival and Functionally Regulates Response to Chemotherapy," *Cancer Discovery* 1(1):54-67, American Association for Cancer Research, United States (Jun. 2011).

Dondelinger, M., et al., "Understanding the Significance and Implications of Antibody Numbering and Antigen-Binding Surface/Residue Definition," Front Immunol 9:2278, Frontiers Media SA., Switzerland (Oct. 2018).

Drake, A.W., and Klakamp, S.L., "A Rigorous Multiple Independent Binding Site Model for Determining Cell-based Equilibrium Dissociation Constants," *Journal of Immunological Methods* 318(1-2):147-152, Elsevier, Netherlands (Jan. 2007).

Engle, S.J., et al., "Best Practices For Translational Disease Modeling Using Human iPSC-derived Neurons," *Neuron* 100(4):783-797, Cell Press, United States (Nov. 2018).

He Li, W., "Research progress in MS4A gene family and tumor," Tumor 36:345-350, China Academic Journal Electronic Publishing House, China (Mar. 2016).

He Li, W., "Research progress on MS4A gene family and clinically relevant diseases," Chin J Clin Lab Sci 34(3):202-204, Chinese Medical Journals Publishing House, China (Mar. 2016).

Idusogie, E.E., et al., "Mapping of the C1q Binding Site on Rituxan, A Chimeric Antibody with a Human IgG1 Fc," *The Journal of Immunology* 164(8):4178-4184, American Association of Immunologists, United States (2000).

International Search Report and Written Opinion for Application No. PCT/US2019/016156, European Patent Office, Netherlands, mailed on Apr. 23, 2019, 13 pages.

International Search Report and Written Opinion mailed Jan. 28, 2021, in Application No. PCT/US2020/044335, EPO, Netherlands, 15 pages.

International Search Report for International Application No. PCT/US2019/016141, Korean Intellectual Property Office, Republic of Korea, mailed May 20, 2019, 11 pages.

Koenig, P., et al., "Mutational landscape of antibody variable domains reveals a switch modulating the interdomain conformational dynamics and antigen binding," *PNAS* 114(4):E486-E496, National Academy of Sciences, United States (2017).

Kuek, L.E., et al., "The MS4A family: counting past 1, 2 and 3," *Immunology and Cell Biology* 94:11-23, American Society for Immunology Inc., United States (Apr. 2015).

Kussie, P.H., et al., "A Single Engineered Amino Acid Substitution Changes Antibody Fine Specificity," Journal of Immunology 152(1):146-152, American Association of Immunology, United States (1994).

Morris, G.E., "Epitope Mapping of Protein Antigens by Competition ELISA," The Protein Protocols Handbook, pp. 595-600, Humana Press, United States (1996).

Murthy, M.N., et al., "Increased Brain Expression of GPNMB Is Associated with Genome Wide Significant Risk for Parkinson's Disease on Chromosome 7p15.3," *Neurogenetics* 18(3):121-133, Springer-Verlag, Germany (Jul. 2017).

Office Action mailed Feb. 28, 2022, in U.S. Appl. No. 16/965,676, Kong, P., et al., filed Jul. 29, 2020, 16 pages.

Office Action mailed Jun. 16, 2022, in U.S. Appl. No. 16/943,123, Sun, J., et al., filed Jul. 30, 2020, 7 pages.

Office Action mailed Oct. 18, 2021 in U.S. Appl. No. 16/943,123, Sun, J., et al., filed Jul. 30, 2020, 15 pages.

Office Action mailed Oct. 3, 2022, in U.S. Appl. No. 16/943,123, Sun, J., et al., filed Jul. 30, 2020, 3 pages.

Peng, X., et al., "Preclinical Evaluation of 3D185, a Novel Potent Inhibitor of FGFR1/2/3 and CSF-1R, in FGFR-Dependent and Macrophage-Dominant Cancer models," *Journal of Experimental & Clinical Cancer Research* 38(1):372, 16 pages, BioMed Central, United Kingdom (Aug. 2019).

Piccio, L., et al., "Cerebrospinal Fluid Soluble TREM2 is Higher in Alzheimer Disease and Associated With Mutation Status," *Acta Neuropathologica* 131(6):925-933, Springer Verlag, Germany (Jun. 2016).

Pocock, J.M., et al., "Modelling Microglial Function With Induced Pluripotent Stem Cells: An Update," *Nature Reviews Neuroscience* 19(8):445-452, Nature Publishing Group, United Kingdom (Aug. 2018).

Puri, M., et al., "The Evaluation of MS4A4A and MS4A8B Expression in Hematopoietic Cells," retrieved from: https://prism.ucalgary.ca/bitstream/handle/11023/1791/ucalgary2014purmandip.pdf;jsessionid=cda23b615634fb7f5836e43810707090?sequence=2, retrieved Oct. 21, 2020, 160 pages (2014).

Reitz, C., "Toward Precision medicine in Alzheimer's Disease," Ann. Transl. Med 4(6):107, 7 pages, AME Publishing Corp, United States (2016).

Rudikoff, S., et al., "Single amino acid substitution altering antigen-binding specificity," Proc Natl Acad Sci USA 79(6):1979-1983, National Academy of Sciences, United States (Mar. 1982).

Salimi, A., et al., "Comparison Of Different Protocols For Neural Differentiation Of Human Induced Pluripotent Stem Cells," *Molecular Biology Reports* 41(3):1713-1721, Springer, Netherlands (Mar. 2014).

(56) References Cited

OTHER PUBLICATIONS

Sanyal, R., et al., "MS4A4A: a novel cell surface marker for M2 macrophages and plasma cells," *Immunology and Cell Biology* 95(7):611-619, American Society for Immunology Inc., United States (Apr. 2017).

Sekine, S. "The Current State and the Issues of Antibody Drugs," *Science and Technology Trends*, 10:13-25, (Oct. 2009).

Sela-Culang, I., et al., "The structural basis of antibody-antigen recognition," Front Immunol 4:302, Frontiers Media SA., Switzerland (Oct. 2013).

Shang, L., et al., "Selective Antibody Intervention of Toll-like Receptor 4 Activation through Fc γ Receptor Tethering," *The Journal of Biological Chemistry* 289(22):15309-15318, American Society for Biochemistry and Molecular Biology, United States (May 2014).

Shih-Feng, Y., et al., "MS4A4A modifies the risk of Alzheimer disease by regulating lipid metabolism and immune response in a unique microglia state," MedRxiv 10.1101/2023.02.06.23285545, accessed at https://www.medrixiv.org/content/10.1101/2023.02.06.23285545v1.full.pdf, accessed on Feb. 26, 2024 (Feb. 2023).

Stanford Health Now, "Alzheimer's Prevention, Treatment and Research—A Q&A with Dr. Frank Longo," retrieved from: stanfordhealthcare.org/Stanford-health-now/2016/alzheimers-prevention-treatment-research-qa-longo.html, accessed on May 3, 2016, 2 pages.

TCW, J., et al., "An Efficient Platform For Astrocyte Differentiation From Human Induced Pluripotent Stem Cells," *Stem Cell Reports* 9(2):600-614, Cell Press, United States (Aug. 2017).

Thornton, P., et al., "TREM2 shedding by cleavage at the H157-S158 bond is accelerated for the Alzheimer's disease-associated H157Y variant," *EMBO Mol Med* 9:1366-1378, Wiley-Blackwell, United Kingdom (Oct. 2017).

Tomay, F., "Regulation and function of the tetraspanin-like molecule MS4A4A in alternatively activated and tumor-associated macrophages," XP055578452, Retrieved from the Internet: https://air.unimi.it/retrieve/handle/2434/248877/338927/phd_unimi_R09505.pdf, Feb. 10, 2015, pp. 1-160.

International Search Report and Written Opinion for International Application No. PCT/US2023/077418, European Patent Office, Netherlands, mailed Feb. 12, 2024, 11 pages.

NCBI, "Membrane-spanning 4-domains subfamily A member 4A isoform 1 [*Homo sapiens*]," Accession No. NP_683876, May 2, 2019, accessed at https://www.ncbi.nlm.nih.gov/protein/NP_683876.1/, 3 pages.

\* cited by examiner

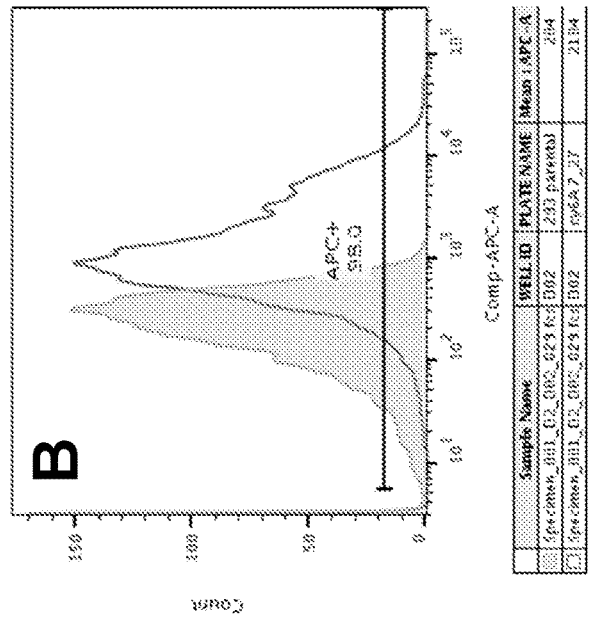
FIG. 2A
FIG. 2B
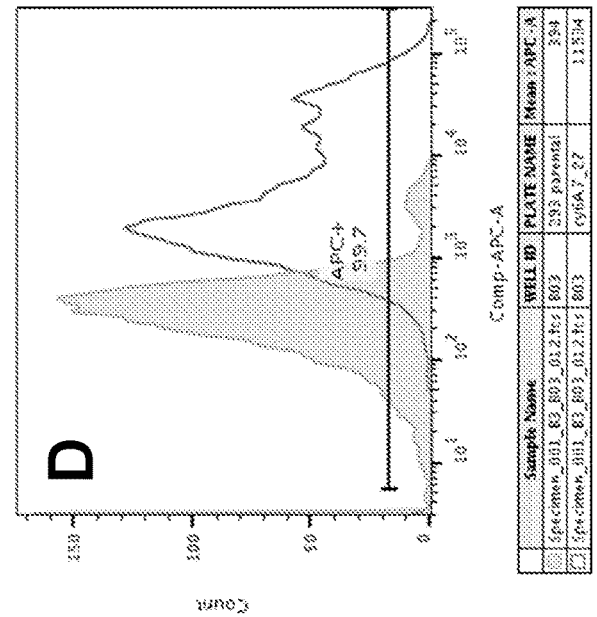
FIG. 2C
FIG. 2D

ANTI-MS4A6A ANTIBODIES AND METHODS OF USE THEREOF

CROSS-REFERENCE TO RELATED APPLICATIONS

This application is a Continuation of U.S. application Ser. No. 16/965,675, § 371(c) date: Jul. 29, 2020, which is a U.S. national stage entry of PCT/US2019/016141, filed Jan. 31, 2019, which claims the benefit of U.S. Provisional Application No. 62/624,578, filed Jan. 31, 2018, and U.S. Provisional Application No. 62/646,846 filed Mar. 22, 2018, each of which is hereby incorporated by reference in its entirety.

REFERENCE TO A SEQUENCE LISTING SUBMITTED ELECTRONICALLY VIA EFS-WEB

The content of the electronically submitted sequence listing (Name: 4503_0030003_Seqlisting_ST25. txt; Size: 64,712 bytes; and Date of Creation: Jul. 26, 2022) is herein incorporated by reference in its entirety.

FIELD OF THE PRESENT DISCLOSURE

The present disclosure relates to anti-MS4A6A antibodies and therapeutic uses of such antibodies.

BACKGROUND OF THE PRESENT DISCLOSURE

The membrane-spanning 4-domain subfamily A (MS4A) gene cluster is present on chromosome 11q12 and includes eighteen genes. The MS4A gene family encodes membrane proteins typically having tetra-spanning topology (Ishibashi et al., 2001, Gene, 265:87-93; Liang and Tedder, 2001, Genomics, 72:119-127; Efthymiou and Goate, 2017, Molecular Neurodegeneration, 12:43). The membrane spanning domains are interconnected by one intracellular loop and two extracellular loops with both N- and C-termini residing within the cytosol. Most MS4A proteins share amino acid sequence homology to that of MS4A1 (CD20) (20-30% similarity), with the highest degree of sequence identity occurring in the first three transmembrane domains. The highly conserved motifs within these transmembrane regions across different MS4A proteins suggest that the membrane spanning domains have an important general role in MS4A protein function. The regions of greatest variation between MS4A proteins occur within their N- and C-terminal cytoplasmic domains and the putative second extracellular loop (Ishibashi et al., 2001, Gene, 265:87-93), suggesting that these regions impart unique functional properties.

Despite this diversity, the MS4A domains possess some shared elements. For instance, one notable feature conserved in MS4A proteins (with the exception of MS4A8B and MS4A12) is the conservation of two cysteine residues in the putative second extracellular loop that may form a disulfide bridge. The N- and C-terminal domains of MS4A proteins are also rich in proline residues, although the functional significance of this remains to be elucidated (Hulett et al., 2001, Genomics, 72:119-127). Proline rich regions are, however, commonly involved in various cellular processes such as cytoskeletal rearrangement, initiation of transcription, signaling cascades, and association with SH3 domains as part of an adaptor system to facilitate protein-protein interactions (Kay et al., 2000, FASEB J, 14:231-241).

The MS4A protein family is relatively uncharacterized functionally, with some important exceptions: MS4A1 (CD20) is expressed exclusively in B lymphocytes, where the protein has a function in signaling by the B cell antigen receptor, and calcium influx. CD20 is the target of immunotherapeutic antibodies used to deplete pathogenic B cells in chronic lymphocytic leukemia, lymphomas, autoimmune diseases, and in solid organ transplantation. MS4A2 (FcεRβ) is a signaling subunit of the high affinity IgE receptor (FcγRI) and the low affinity IgG receptor (FcγRIII) on mast cells, having a key role in hypersensitivity and allergic reactions. MS4A2 is an ITAM-domain protein that amplifies signals through a 4-protein high affinity IgE receptor complex. MS4A3 (Htm4) is expressed on intracellular membranes of lymphoid and myeloid cells, and functions as an adaptor protein in cell cycle regulation.

While the majority of MS4A family members are uncharacterized, reports suggest MS4A proteins act as chemosensors and chemoreceptors for a variety of exogenous and endogenous ligands, including fatty acids, peptides, and sulfated steroids, and have been implicated in mediating calcium influx, regulating endocytosis, trafficking, and may act as adapters for signal transduction complexes (Cruse et al., 2015, Mol Biol Cell, 26:1711-1727; Greer et al., 2016, Cell, 165:1734-1748; Eon Kuek et al., 2016, Cell, 165:1734-1748; Koslowski et al., 2008, Cancer Res, 68:3458-3466; Bubien et al., 1993; J Cell Biol, 121:1121-1132).

Certain MS4A genes have been genetically linked to various disorders and diseases, in particular neurodegenerative disorders. For example, genome-wide significance association analyses have identified the MS4A gene cluster, located on chromosome 11q12, as one of the most significant Alzheimer's disease loci. One gene of particular interest identified is MS4A6A (Lambert et al., 2013, Nat Genet, 45:1452-1458; Hollingworth et al., 2011, Nat Genet, 43:429-435; Naj et al., 2011, Nat Genet, 43:436-441). Various SNPs and associated alleles within the MS4A6A locus may contribute to differential expression (e.g., decreased expression or activity) of MS4A6A protein associated with disease risk (Ma et al, 2015, Mol Neurobiol, 51:1240-1248; Lacher et al., 2018, Redox Biology, 14:686-693).

Accordingly, there is a need for therapies targeting MS4A6A, including antibodies that specifically bind to MS4A6A, and/or therapies that are capable of modulating (e.g., activating or enhancing) the activity of MS4A6A, such as by increasing MS4A6A protein levels or activity, in order to treat various diseases, disorders, and conditions associated with MS4A6A activity.

All references cited herein, including patent applications and publications, are hereby incorporated by reference in their entirety.

SUMMARY OF THE PRESENT DISCLOSURE

The present disclosure is generally directed to anti-MS4A6A antibodies and methods of using such antibodies. The methods provided herein find use in preventing, reducing risk, or treating an individual having a neurodegenerative disease, disorder, or condition. In some embodiments, the present disclosure provides a method for preventing, reducing risk, or treating an individual having a neurodegenerative disease, disorder, or condition selected from the group consisting of Alzheimer's disease, late onset Alzheimer's disease, dementia, and cognitive impairment, the method comprising administering to the individual in need thereof a therapeutically effective amount of an anti-MS4A6A antibody. In some embodiments, the present disclosure provides a method for preventing, reducing risk, or treating an individual having a disease, disorder, or condition associated with reduced expression or activity of MS4A6A, the method comprising administering to the individual in need thereof a therapeutically effective amount of an anti-MS4A6A antibody.

In some embodiments, the present disclosure provides a method of preventing, reducing risk, or treating an individual having a disease, disorder, condition, or injury caused by or associated with reduced activity or expression of MS4A6A, the method comprising administering to the individual in need thereof a therapeutically effective amount of an anti-MS4A6A antibody. In some embodiments, the present disclosure provides a method of preventing, reducing risk, or treating an individual having a disease, disorder, condition, or injury caused by or associated with loss of function of MS4A6A, the method comprising administering to the individual in need thereof a therapeutically effective amount of an anti-MS4A6A antibody. In some embodiments, the present disclosure provides a method of preventing, reducing the risk, or treating a neurodegenerative disease, disorder, condition, or injury in an individual having at least one genetic allele associated with Alzheimer's disease risk or susceptibility, the method comprising administering to the individual in need thereof a therapeutically effective amount of an anti-MS4A6A antibody. In some embodiments, the genetic allele associated with Alzheimer's disease risk or susceptibility is selected from the group consisting of rs583791(C) allele, rs7232(T) allele, and rs610932(G) allele.

In certain embodiments that may be combined with any of the preceding embodiments, an anti-MS4A6A antibody of the present disclosure binds a discontinuous MS4A6A epitope. In certain embodiments that may be combined with any of the preceding embodiments, the discontinuous MS4A6A epitope comprises two or more peptides, three or more peptides, four or more peptides, five or more peptides, six or more peptides, seven or more peptides, eight or more peptides, nine or more peptides, or 10 or more peptides. In certain embodiments that may be combined with any of the preceding embodiments, each of the peptides comprise five or more, six or more, seven or more, eight or more, nine or more, 10 or more, 11 or more, 12 or more, 13 or more 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, or 30 or more amino acid residues of the amino acid sequence of SEQ ID NO: 1, of the amino acid sequence of SEQ ID NO:2, or of the amino acid sequence of SEQ ID NO:3; or five or more, six or more, seven or more, eight or more, nine or more, 10 or more, 11 or more, 12 or more, 13 or more 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, or 30 or more amino acid residues on a mammalian MS4A6A protein corresponding to the amino acid sequence of SEQ ID NO: 1, to the amino acid sequence of SEQ ID NO:2, or to the amino acid sequence of SEQ ID NO:3.

In certain embodiments that may be combined with any of the preceding embodiments, an anti-MS4A6A antibody of the present disclosure binds to a conformational epitope of MS4A6A. In certain embodiments that may be combined with any of the preceding embodiments, an anti-MS4A6A antibody of the present disclosure binds to a linear epitope of MS4A6A.

In some embodiments that may be combined with any of the preceding embodiments, an anti-MS4A6A antibody of the present disclosure competes with one or more reference anti-MS4A6A antibodies selected from the group consisting of 6A-1, 6A-2, 6A-3, 6A-4, 6A-5, 6A-6, 6A-7, 6A-8, 6A-9, 6A-10, 6A-11, 6A-12, 6A-13, 6A-14, 6A-15, 6A-16, 6A-17, 6A-18, 6A-20, 6A-21, 6A-22, 6A-23. In some embodiments, the anti-MS4A6A antibody comprises the $V_H$ an $V_L$ (e.g., as shown in Table 4B below) of an antibody selected from the group consisting of: 6A-1, 6A-2, 6A-3, 6A-4, 6A-5, 6A-6, 6A-7, 6A-8, 6A-9, 6A-10, 6A-11, 6A-12, 6A-13, 6A-14, 6A-15, 6A-16, 6A-17, 6A-18, 6A-20, 6A-21, 6A-22, and 6A-23. [16] In some embodiments that may be combined with any of the preceding embodiments, an anti-MS4A6A antibody of the present disclosure binds to an epitope of human MS4A6A that is the same as or overlaps with the MS4A6A epitope bound by at least one reference antibody selected from 6A-1, 6A-2, 6A-3, 6A-4, 6A-5, 6A-6, 6A-7, 6A-8, 6A-9, 6A-10, 6A-11, 6A-12, 6A-13, 6A-14, 6A-15, 6A-16, 6A-17, 6A-18, 6A-20, 6A-21, 6A-22, 6A-23. In some embodiments, the anti-MS4A6A antibody comprises the $V_H$ an $V_L$ (e.g., as shown in Table 4B below) of an antibody selected from the group consisting of: 6A-1, 6A-2, 6A-3, 6A-4, 6A-5, 6A-6, 6A-7, 6A-8, 6A-9, 6A-10, 6A-11, 6A-12, 6A-13, 6A-14, 6A-15, 6A-16, 6A-17, 6A-18, 6A-20, 6A-21, 6A-22, and 6A-23. [17] In some embodiments that may be combined with any of the preceding embodiments, an anti-MS4A6A antibody of the present disclosure binds essentially the same MS4A6A epitope bound by at least one reference antibody selected from 6A-1, 6A-2, 6A-3, 6A-4, 6A-5, 6A-6, 6A-7, 6A-8, 6A-9, 6A-10, 6A-11, 6A-12, 6A-13, 6A-14, 6A-15, 6A-16, 6A-17, 6A-18, 6A-20, 6A-21, 6A-22, 6A-23, and any combination thereof. In some embodiments, the anti-MS4A6A antibody comprises the $V_H$ an $V_L$ (e.g., as shown in Table 4B below) of an antibody selected from the group consisting of: 6A-1, 6A-2, 6A-3, 6A-4, 6A-5, 6A-6, 6A-7, 6A-8, 6A-9, 6A-10, 6A-11, 6A-12, 6A-13, 6A-14, 6A-15, 6A-16, 6A-17, 6A-18, 6A-20, 6A-21, 6A-22, and 6A-23. [18] In some embodiments that may be combined with any of the preceding embodiments, an anti-MS4A6A antibody of the present disclosure binds to a linear epitope on MS4A6A. In some embodiments that may be combined with any of the preceding embodiments, an anti-MS4A6A antibody of the present disclosure binds to one or more amino acids within amino acid residues 1-46 of human MS4A6A. In some embodiments that may be combined with any of the preceding embodiments, an anti-MS4A6A antibody of the present disclosure binds to one or more amino acids within amino acid residues 47-67 of human MS4A6A. In some embodiments that may be combined with any of the preceding embodiments, an anti-MS4A6A antibody of the present disclosure bind to one or more amino acids within amino acid residues 68-84 of human MS4A6A. In some embodiments that may be combined with any of the preceding embodiments, an anti-MS4A6A antibody of the present disclosure binds to one or more amino acids within amino acid residues 85-105 of human MS4A6A. In some embodiments that may be combined with any of the preceding embodiments, an anti-MS4A6A of the present disclosure binds to one or more amino acids within amino acid residues 106-116 of human MS4A6A. In some embodiments, an anti-MS4A6A of the present disclosure binds to one or more amino acids within amino acid residues 117-137 of human MS4A6A. In some embodiments that may be combined with any of the preceding embodiments, an anti-MS4A6 of the present disclosure binds to one or more amino acids within amino acid residues 138-185 of human MS4A6A. In some embodiments that may be combined with any of the preceding embodiments, an anti-MS4A6A of the present disclosure binds to one or more amino acids within amino acid residues 186-206 of human MS4A6A. In some embodiments that may be combined with any of the preceding embodiments, an anti-MS4A6A of the present disclosure binds to one or more amino acids within amino acid residues 207-248 of human MS4A6A. In some embodiments that may be combined with any of the preceding embodiments, an anti-MS4A6A antibody of the present disclosure binds to the amino acid residue at position 185 of human MS4A6A. In some embodiments that may be combined with any of the preceding embodiments, an anti-MS4A6A antibody of the present disclosure binds to extracellular domain 1 (ECL1) of MS4A6A. In some embodiments, an anti-MS4A6A antibody of the present disclosure binds to extracellular domain 2 (ECL2) of MS4A6A. In some embodiments, an anti-MS4A6A antibody of the present disclosure binds to ECL1 domain and ECL2 domain of MS4A6A.

In some embodiments that may be combined with any of the preceding embodiments, an anti-MS4A6A of the present disclosure is an isolated antibody that binds to human MS4A6A, wherein the antibody comprises a heavy chain variable region and a light chain variable region, wherein the heavy chain variable region comprises: an HVR-H1 comprising an amino acid sequence selected from the group consisting of SEQ ID NOs:4-16; an HVR-H2 comprising an amino acid sequence selected from the group consisting of SEQ ID NOs:17-31; and an HVR-H3 comprising an amino acid sequence selected from the group consisting of SEQ ID NOs:32-45; and the light chain variable region comprises: an HVR-L1 comprising an amino acid sequence selected from the group consisting of SEQ ID NOs:46-60; an HVR-L2 comprising an amino acid sequence selected from the group consisting of SEQ ID NOs:61-76; and an HVR-L3 comprising an amino acid sequence selected from the group consisting of SEQ ID NOs:77-90.

In some embodiments that may be combined with any of the preceding embodiments, an anti-MS4A6A of the present disclosure is an isolated antibody that binds to human MS4A6A, wherein the antibody comprises a heavy chain variable region, wherein the heavy chain variable region comprises an amino acid sequence selected from the group consisting of SEQ ID NOs:91-108.

In some embodiments that may be combined with any of the preceding embodiments, an anti-MS4A6A of the present disclosure is an isolated antibody that binds to human MS4A6A, wherein the antibody comprises a light chain variable region, wherein the light chain variable region comprises an amino acid sequence selected from the group consisting of SEQ ID NOs:109-126.

In some embodiments that may be combined with any of the preceding embodiments, an anti-MS4A6A of the present disclosure is an isolated antibody that binds to human MS4A6A, wherein the antibody comprises a heavy chain variable region and a light chain variable region, wherein the heavy chain variable region comprises an amino acid sequence selected from the group consisting of SEQ ID NOs:91-108; and wherein the light chain variable region comprises an amino acid sequence selected from the group consisting of SEQ ID NOs:109-126.

In certain embodiments that may be combined with any of the preceding embodiments, the MS4A6A protein is a mammalian protein or a human protein. In certain embodiments that may be combined with any of the preceding embodiments, the MS4A6A protein is a wild-type protein. In certain embodiments that may be combined with any of the preceding embodiments, the MS4A6A protein is a naturally occurring variant. In certain embodiments that may be combined with any of the preceding embodiments, the antibody is an agonist antibody, wherein the antibody induces, increases, or enhances one or more MS4A6A activities. In certain embodiments that may be combined with any of the preceding embodiments, the isolated antibody induces, enhances, or retains MS4A6A clustering on a cell surface.

In some embodiments that may be combined with any of the preceding embodiments, an anti-MS4A6A antibody of the present disclosure increases or enhances the interaction or binding of MS4A6A and at least one MS4A6A ligand or binding partner.

In some embodiments that may be combined with any of the preceding embodiments, an anti-MS4A6A antibody of the present disclosure enhances or increases the formation of signaling complexes. In some embodiments that may be combined with any of the preceding embodiments, an anti-MS4A6A antibody of the present disclosure enhances or increases the formation of signaling complexes associated with ITAM-encoding adaptor proteins. In some embodiments that may be combined with any of the preceding embodiments, an anti-MS4A6A antibody of the present disclosure enhances or increases the formation of inhibitory signaling complexes. In some embodiments that may be combined with any of the preceding embodiments, an anti-MS4A6A antibody of the present disclosure enhances or increases the formation of inhibitory signaling complexes associated with ITIM-encoding adaptor proteins.

In some embodiments that may be combined with any of the preceding embodiments, an anti-MS4A6A antibody of the present disclosure inhibits (e.g., blocks) or reduces the formation of signaling complexes. In some embodiments that may be combined with any of the preceding embodiments, an anti-MS4A6A antibody of the present disclosure inhibits (e.g., blocks) or reduces the formation of signaling complexes associated with ITAM-encoding adaptor proteins. In some embodiments that may be combined with any of the preceding embodiments, an anti-MS4A6A antibody of the present disclosure inhibits (e.g., blocks) or reduces the formation of inhibitory signaling complexes. In some embodiments that may be combined with any of the preceding embodiments, an anti-MS4A6A antibody of the present disclosure inhibits (e.g., blocks) or reduces the formation of inhibitory signaling complexes associated with ITIM-encoding adaptor proteins.

In some embodiments that may be combined with any of the preceding embodiments, an anti-MS4A6A antibody of the present disclosure inhibits (e.g., blocks) or reduces formation of MS4A6A homo-oligomeric cell surface protein complexes by: a) reducing the effective levels of MS4A6A available for MS4A6A homo-oligomeric complex formation; b) blocking one or more of the sites on MS4A6A required for MS4A6A homo-oligomeric complex formation; c) preventing one or more posttranslational events on MS4A6A that are required for MS4A6A homo-oligomeric complex formation and/or for correct processing and/or cellular localization of MS4A6A; d) inducing degradation of MS4A6A; e) changing the conformation of MS4A6A, or any combination thereof.

In some embodiments that may be combined with any of the preceding embodiments, an anti-MS4A6A antibody of the present disclosure increases or enhances formation of MS4A6A homo-oligomeric cell surface protein complexes by: a) increasing the effective levels of MS4A6A available for MS4A6A homo-oligomeric complex formation; b) stabilizing one or more of the sites on MS4A6A required for MS4A6A homo-oligomeric complex formation; c) maintaining cell surface expression of MS4A6A to allow for homo-oligomeric complex formation and/or for correct processing and/or maintaining correct cellular localization of MS4A6A; d) reducing degradation of MS4A6A; e) changing the conformation of MS4A6A, or any combination thereof.

In some embodiments that may be combined with any of the preceding embodiments, an anti-MS4A6A antibody of the present disclosure inhibits (e.g., blocks) or reduces MS4A6A hetero-oligomeric cell surface protein complex formation with one or more signal transduction adaptor proteins by: a) reducing the effective levels of MS4A6A available for MS4A6A hetero-oligomeric complex formation; b); blocking one or more of the sites on MS4A6A required for MS4A6A hetero-oligomeric complex formation; c) preventing one or more posttranslational events on MS4A6A that are required for MS4A6A hetero-oligomeric complex formation and/or for correct processing and/or cellular localization of MS4A6A; d) inducing degradation of MS4A6A; e) changing the conformation of MS4A6A, or any combination thereof.

In some embodiments that may be combined with any of the preceding embodiments, an anti-MS4A6A antibody of the present disclosure increases or enhances MS4A6A hetero-oligomeric cell surface protein complex formation with one or more signal transduction adaptor proteins by: a) increasing the effective levels of MS4A6A available for MS4A6A hetero-oligomeric complex formation; b) stabilizing one or more of the sites on MS4A6A required for MS4A6A hetero-oligomeric complex formation; c) maintaining cell surface expression of MS4A6A to allow for MS4A6A hetero-oligomeric complex formation and/or for correct processing and/or maintaining correct cellular localization of MS4A6A; d) reducing degradation of MS4A6A; e) changing the conformation of MS4A6A, or any combination thereof.

In certain embodiments that may be combined with any of the preceding embodiments, the anti-MS4A6A antibody is a human antibody, a humanized antibody, a bispecific antibody, a monoclonal antibody, a multivalent antibody, a conjugated antibody, or a chimeric antibody.

In certain embodiments that may be combined with any of the preceding embodiments, the anti-MS4A6A antibody is a bispecific antibody recognizing a first antigen and a second antigen. In certain embodiments that may be combined with any of the preceding embodiments, the first antigen is MS4A6A and the second antigen is an antigen facilitating transport across the blood-brain-barrier. In certain embodiments that may be combined with any of the preceding embodiments, the second antigen is selected from the group consisting of MS4A6A, transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopep peptide, basigin, Glut1, and CD98hc, and ANG1005.

In some embodiments that may be combined with any of the preceding embodiments, the antibody is a monoclonal antibody. In some embodiments that may be combined with any of the preceding embodiments, the antibody is a human antibody. In some embodiments that may be combined with any of the preceding embodiments, the antibody is a humanized antibody. In some embodiments that may be combined with any of the preceding embodiments, the antibody is a bispecific antibody. In some embodiments that may be combined with any of the preceding embodiments, the antibody is a multivalent antibody. In some embodiments that may be combined with any of the preceding embodiments, the antibody is a chimeric antibody. In some embodiments that may be combined with any of the preceding embodiments, the antibody is of the IgG class, the IgM class, or the IgA class. In some embodiments, the antibody is of the IgG class and has an IgG1, IgG2, or IgG4 isotype. In certain embodiments that may be combined with any of the preceding embodiments, the anti-MS4A6A antibody is an antibody fragment that binds to an epitope comprising amino acid residues on human MS4A6A or a mammalian MS4A6A protein. In certain embodiments that may be combined with any of the preceding embodiments, the fragment is an Fab, Fab', Fab'-SH, F(ab')2, Fv, or scFv fragment.

Other aspects of the present disclosure relate to an isolated (e.g., monoclonal) anti-MS4A6A antibody, wherein the anti-MS4A6A antibody comprises at least one, two, three, four, five, or six HVRs of an antibody selected from the group consisting of: 6A-1, 6A-2, 6A-3, 6A-4, 6A-5, 6A-6, 6A-7, 6A-8, 6A-9, 6A-10, 6A-11, 6A-12, 6A-13, 6A-14, 6A-15, 6A-16, 6A-17, 6A-18, 6A-20, 6A-21, 6A-22, and 6A-23. In some embodiments, the anti-MS4A6A antibody comprises the six HVRs (e.g., as shown in Table 4A below) of an antibody selected from the group consisting of: 6A-1, 6A-2, 6A-3, 6A-4, 6A-5, 6A-6, 6A-7, 6A-8, 6A-9, 6A-10, 6A-11, 6A-12, 6A-13, 6A-14, 6A-15, 6A-16, 6A-17, 6A-18, 6A-20, 6A-21, 6A-22, and 6A-23. In some embodiments, the anti-MS4A6A antibody comprises the $V_H$ and/or $V_L$ of an antibody selected from the group consisting of: 6A-1, 6A-2, 6A-3, 6A-4, 6A-5, 6A-6, 6A-7, 6A-8, 6A-9, 6A-10, 6A-11, 6A-12, 6A-13, 6A-14, 6A-15, 6A-16, 6A-17, 6A-18, 6A-20, 6A-21, 6A-22, and 6A-23. In some embodiments, the anti-MS4A6A antibody comprises the $V_H$ an $V_L$ (e.g., as shown in Table 4B below) of an antibody selected from the group consisting of: 6A-1, 6A-2, 6A-3, 6A-4, 6A-5, 6A-6, 6A-7, 6A-8, 6A-9, 6A-10, 6A-11, 6A-12, 6A-13, 6A-14, 6A-15, 6A-16, 6A-17, 6A-18, 6A-20, 6A-21, 6A-22, and 6A-23.

Other aspects of the present disclosure relate to an isolated nucleic acid comprising a nucleic acid sequence encoding the anti-MS4A6A antibody of any of the preceding embodiments. Other aspects of the present disclosure relate to a vector comprising the nucleic acid of any of the preceding embodiments. Other aspects of the present disclosure relate to an isolated host cell comprising the vector of any of the preceding embodiments. Other aspects of the present disclosure relate to a method of producing an anti-MS4A6A antibody, comprising culturing the host cell of any of the preceding embodiments so that the anti-MS4A6A antibody is produced. In certain embodiments, the method further comprises recovering the anti-MS4A6A antibody produced by the host cell. Other aspects of the present disclosure relate to an isolated anti-MS4A6A antibody produced by the method of any of the preceding embodiments. Other aspects of the present disclosure relate to a pharmaceutical composition comprising the anti-MS4A6A antibody of any of the preceding embodiments, and a pharmaceutically acceptable carrier.

In certain embodiments that may be combined with any of the preceding embodiments, the anti-MS4A6A antibody binds specifically to human MS4A6A, mouse MS4A6A, cyno MS4A6A, or a combination thereof.

It is to be understood that one, some, or all of the properties of the various embodiments described herein may be combined to form other embodiments of the present disclosure. These and other aspects of the disclosure will become apparent to one of skill in the art. These and other embodiments of the disclosure are further described by the detailed description that follows.

BRIEF DESCRIPTION OF THE DRAWINGS

FIG. 2A and FIG. 2C show two independent FAC analyses of HEK293 cells transfected with human MS4A6A (clear trace in FIGS. 2A and 2C) and non-transfected HEK293 cells (shaded trace in FIGS. 2A and 2C) using hybridoma supernatant containing anti-MS4A6A of the present disclosure. FIG. 2B and FIG. 2D show two independent FAC analyses of HEK293 cells transfected with cyno MS4A6A (clear trace in FIGS. 2B and 2D) and non-transfected HEK293 cells (shaded trace in FIGS. 2B and 2D) using hybridoma supernatant containing anti-MS4A6A of the present disclosure.

DETAILED DESCRIPTION OF THE PRESENT DISCLOSURE

Figure 1:
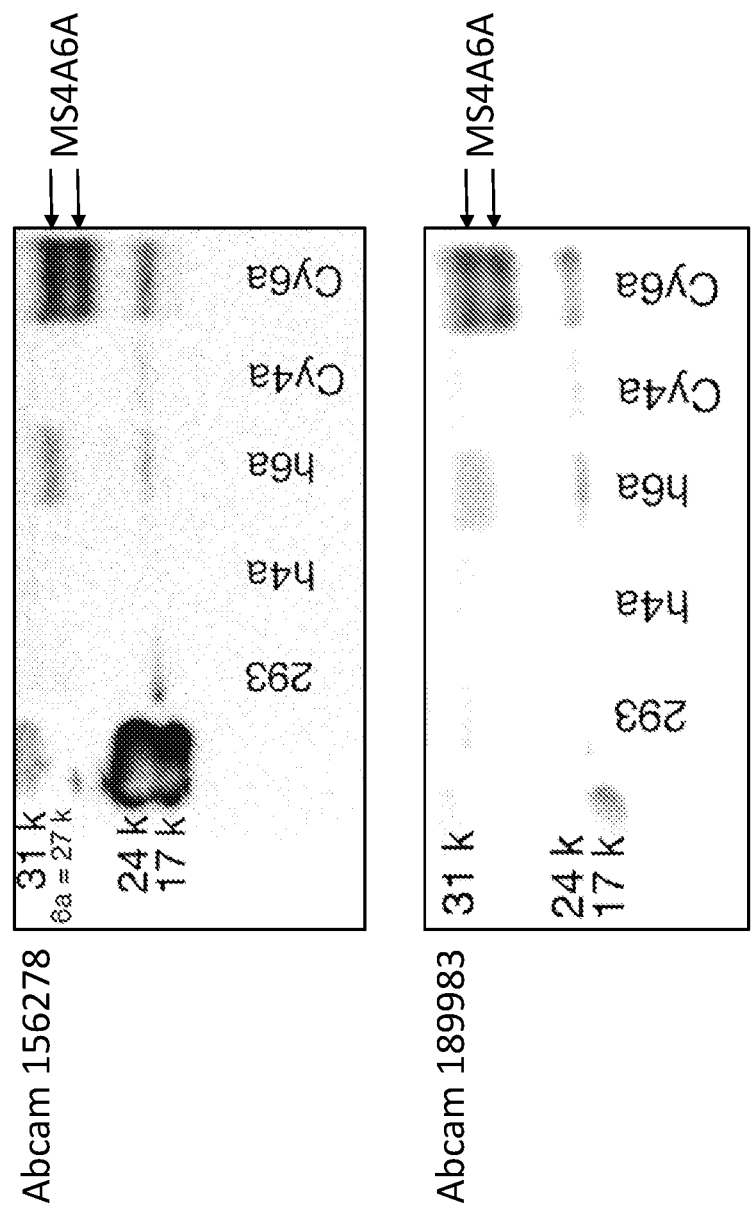
FIG. 1 shows immunoblots from cells transiently-transfected with either human or cyno MS4A6A or MS4A4A and probed using two commercially-available anti-MS4A6A antibodies from Abcam. Both antibodies detect human and cyno MS4A6A-specific bands, demonstrating that the cells expressed MS4A6A protein.

The present disclosure relates to anti-MS4A6A antibodies (e.g., monoclonal antibodies); methods of making and using such antibodies; pharmaceutical compositions comprising such antibodies; nucleic acids encoding such antibodies; and host cells comprising nucleic acids encoding such antibodies.

The techniques and procedures described or referenced herein are generally well understood and commonly employed using conventional methodology by those skilled in the art, such as, for example, the widely utilized methodologies such as those described in Sambrook et al. *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003); *Monoclonal Antibodies: A Practical Approach* (P. Shepherd and C. Dean, eds., Oxford University Press, 2000).

I. Definitions

The terms "MS4A6A" or "MS4A6A polypeptide" are used interchangeably herein refer herein to any native MS4A6A from any vertebrate source, including mammals such as primates (e.g., humans and cynos) and rodents (e.g., mice and rats), unless otherwise indicated. In some embodiments, the term encompasses both wild-type sequences and naturally occurring variant sequences, e.g., splice variants or allelic variants. In some embodiments, the term encompasses "full-length," unprocessed MS4A6A as well as any form of MS4A6A that results from processing in the cell. In some embodiments, the MS4A6A is human MS4A6A. In some embodiments, the amino acid sequence of an exemplary MS4A6A is Uniprot Accession No. Q9H2W1 as of Mar. 1, 2001. In some embodiments, the amino acid sequence of an exemplary human MS4A6A is SEQ ID NO: 1.

The terms "anti-MS4A6A antibody," an "antibody that binds to MS4A6A," and "antibody that specifically binds MS4A6A" refer to an antibody that is capable of binding MS4A6A with sufficient affinity such that the antibody is useful as a diagnostic and/or therapeutic agent in targeting MS4A6A. In one embodiment, the extent of binding of an anti-MS4A6A antibody to an unrelated, non-MS4A6A polypeptide is less than about 10% of the binding of the antibody to MS4A6A as measured, e.g., by a radioimmunoassay (RIA). In certain embodiments, an antibody that binds to MS4A6A has a dissociation constant (KD) of <1 µM, <100 nM, <10 nM, <1 nM, <0.1 nM, <0.01 nM, or <0.001 nM (e.g., $10^{-8}$ M or less, e.g. from $10^{-8}$ M to $10^{-13}$ M, e.g., from $10^{-9}$ M to $10^{-13}$ M). In certain embodiments, an anti-MS4A6A antibody binds to an epitope of MS4A6A that is conserved among MS4A6A from different species.

With regard to the binding of an antibody to a target molecule, the term "specific binding" or "specifically binds" or is "specific for" a particular polypeptide or an epitope on a particular polypeptide target means binding that is measurably different from a non-specific interaction. Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a KD for the target of about any of $10^{-4}$ M or lower, $10^{-5}$ M or lower, $10^{-6}$ M or lower, $10^{-7}$ M or lower, $10^{-8}$ M or lower, $10^{-9}$ M or lower, $10^{-10}$ M or lower, $10^{-11}$ M or lower, $10^{-12}$ M or lower or a KD in the range of $10^{-4}$ M to $10^{-6}$ M or $10^{-6}$ M to $10^{-10}$ M or $10^{-7}$ M to $10^{-9}$ M. As will be appreciated by the skilled artisan, affinity and KD values are inversely related. A high affinity for an antigen is measured by a low KD value. In one embodiment, the term "specific binding" refers to binding where a molecule binds to a particular polypeptide or epitope on a particular polypeptide without substantially binding to any other polypeptide or polypeptide epitope.

The term "immunoglobulin" (Ig) is used interchangeably with "antibody" herein. The term "antibody" herein is used in the broadest sense and specially covers monoclonal antibodies, polyclonal antibodies, multispecific antibodies (e.g., bispecific antibodies) including those formed from at least two intact antibodies, and antibody fragments so long as they exhibit the desired biological activity.

"Native antibodies" are usually heterotetrameric glycoproteins of about 150,000 Daltons, composed of two identical Light ("L") chains and two identical heavy ("H") chains. Each light chain is linked to a heavy chain by one covalent disulfide bond, while the number of disulfide linkages varies among the heavy chains of different immunoglobulin isotypes. Each heavy and light chain also has regularly spaced intra-chain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

For the structure and properties of the different classes of antibodies, see, e.g., *Basic and Clinical Immunology*, 8th Ed., Daniel P. Stites, Abba I. Terr and Tristram G. Parslow (eds.), Appleton & Lange, Norwalk, CT, 1994, page 71 and Chapter 6.

The light chain from any vertebrate species can be assigned to one of two clearly distinct types, called kappa ("κ") and lambda ("λ"), based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated alpha ("α"), delta ("δ"), epsilon ("ε"), gamma ("γ"), and mu ("μ"), respectively. The γ and α classes are further divided into subclasses (isotypes) on the basis of relatively minor differences in the CH sequence and function, e.g., humans express the following subclasses: IgG1, IgG2, IgG3, IgG4, IgA1, and IgA2. The subunit structures and three-dimensional configurations of different classes of immunoglobulins are well known and described generally in, for example, Abbas et al., Cellular and Molecular Immunology, 4$^{th}$ ed. (W.B. Saunders Co., 2000).

The "variable region" or "variable domain" of an antibody, such as an anti-MS4A6A antibody of the present disclosure, refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites.

The term "variable" refers to the fact that certain segments of the variable domains differ extensively in sequence among antibodies, such as anti-MS4A6A antibodies of the present disclosure. The variable domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Immunological Interest*, Fifth Edition, National Institute of Health, Bethesda, MD (1991)). The constant domains are not involved directly in the binding of antibody to an antigen, but exhibit various effector functions, such as participation of the antibody in antibody-dependent-cellular toxicity.

The term "monoclonal antibody" as used herein refers to an antibody, such as a monoclonal anti-MS4A6A antibody of the present disclosure, obtained from a population of substantially homogeneous antibodies, i.e., the individual antibodies comprising the population are identical except for possible naturally occurring mutations and/or post-translation modifications (e.g., isomerizations, amidations, etc.) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by a variety of techniques, including, for example, the hybridoma method, recombinant DNA methods, and technologies for producing human or human-like antibodies in animals that have parts or all of the human immunoglobulin loci or genes encoding human immunoglobulin sequences.

The terms "full-length antibody," "intact antibody" or "whole antibody" are used interchangeably to refer to an antibody, such as an anti-MS4A6A antibody of the present disclosure, in its substantially intact form, as opposed to an antibody fragment. Specifically, whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" refers to a molecule other than an intact antibody that comprises a portion of an intact antibody that binds the antigen to which the intact antibody binds. Examples of antibody fragments include Fab, Fab', F(ab')$_2$ and Fv fragments; diabodies; linear antibodies (see U.S. Pat. No. 5,641,870, Example 2; Zapata et al., *Protein Eng.* 8(10):1057-1062 (1995)); single-chain antibody molecules and multispecific antibodies formed from antibody fragments.

Papain digestion of antibodies, such as anti-MS4A6A antibodies of the present disclosure, produces two identical antigen-binding fragments, called "Fab" fragments, and a residual "Fc" fragment, a designation reflecting the ability to crystallize readily. The Fab fragment consists of an entire light chain along with the variable region domain of the heavy chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both heavy chains held together by disulfides. The effector functions of antibodies are determined by sequences in the Fc region, the region which is also recognized by Fc receptors (FcR) found on certain types of cells.

"Functional fragments" of antibodies, such as anti-MS4A6A antibodies of the present disclosure, comprise a portion of an intact antibody, generally including the antigen binding or variable region of the intact antibody or the Fc region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the variable domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains.

As used herein, a "chimeric antibody" refers to an antibody (immunoglobulin), such as a chimeric anti-MS4A6A antibody of the present disclosure, in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity. Chimeric antibodies of interest herein include PRIMATIZED® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., murine) antibodies, such as humanized forms of anti-MS4A6A antibodies of the present disclosure, are chimeric antibodies comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

A "human antibody" is one that possesses an amino-acid sequence corresponding to that of an antibody, such as an anti-MS4A6A antibody of the present disclosure, produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries and yeast-display libraries. Human antibodies can be prepared by administering the antigen to a transgenic animal that has been modified to produce such antibodies in response to antigenic challenge, but whose endogenous loci have been disabled, e.g., immunized xenomice as well as generated via a human B-cell hybridoma technology.

The term "hypervariable region," "HVR," or "HV," when used herein refers to the regions of an antibody-variable domain, such as that of an anti-MS4A6A antibody of the present disclosure, that are hypervariable in sequence and/or form structurally defined loops. Generally, antibodies comprise six HVRs; three in the $V_H$ (H1, H2, H3), and three in the $V_L$ (L1, L2, L3). In native antibodies, H3 and L3 display the most diversity of the six HVRs, and H3 in particular is believed to play a unique role in conferring fine specificity to antibodies. Naturally occurring camelid antibodies consisting of a heavy chain only are functional and stable in the absence of light chain.

A number of HVR delineations are in use and are encompassed herein. In some embodiments, the HVRs may be Kabat complementarity-determining regions (CDRs) based on sequence variability and are the most commonly used (Kabat et al., supra). In some embodiments, the HVRs may be Chothia CDRs. Chothia refers instead to the location of the structural loops (Chothia and Lesk *J. Mol. Biol.* 196: 901-917 (1987)). In some embodiments, the HVRs may be AbM HVRs. The AbM HVRs represent a compromise between the Kabat CDRs and Chothia structural loops, and are used by Oxford Molecular's AbM antibody-modeling software. In some embodiments, the HVRs may be "contact" HVRs. The "contact" HVRs are based on an analysis of the available complex crystal structures. The residues from each of these HVRs are noted below.

| Loop | Kabat | AbM | Chothia | Contact |
|------|-------|-----|---------|---------|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat numbering) |
| H1 | H31-H35 | H26-H35 | H26-H32 | H30-H35 (Chothia numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2), and 89-97 or 89-96 (L3) in the VL, and 26-35 (H1), 50-65 or 49-65 (a preferred embodiment) (H2), and 93-102, 94-102, or 95-102 (H3) in the VH. The variable-domain residues are numbered according to Kabat et al., supra, for each of these extended-HVR definitions.

"Framework" or "FR" residues are those variable-domain residues other than the HVR residues as herein defined.

An "acceptor human framework" as used herein is a framework comprising the amino acid sequence of a $V_L$ or $V_H$ framework derived from a human immunoglobulin framework or a human consensus framework. An acceptor human framework "derived from" a human immunoglobulin framework or a human consensus framework may comprise the same amino acid sequence thereof, or it may comprise pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less. Where pre-existing amino acid changes are present in a VH, preferable those changes occur at only three, two, or one of positions 71H, 73H and 78H; for instance, the amino acid residues at those positions may by 71A, 73T and/or 78A. In one embodiment, the VL acceptor human framework is identical in sequence to the $V_L$ human immunoglobulin framework sequence or human consensus framework sequence.

A "human consensus framework" is a framework that represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. Generally, the subgroup of sequences is a subgroup as in Kabat et al., *Sequences of Proteins of Immunological Interest*, 5th Ed. Public Health Service, National Institutes of Health, Bethesda, Md. (1991). Examples include for the $V_L$, the subgroup may be subgroup kappa I, kappa II, kappa III or kappa IV as in Kabat et al., supra. Additionally, for the $V_H$, the subgroup may be subgroup I, subgroup II, or subgroup III as in Kabat et al., supra.

An "amino-acid modification" at a specified position, e.g., of an anti-MS4A6A antibody of the present disclosure, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

An "affinity-matured" antibody, such as an affinity matured anti-MS4A6A antibody of the present disclosure, is one with one or more alterations in one or more HVRs thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al. *Bio/Technology* 10:779-783 (1992) describes affinity maturation by $V_H$- and $V_L$-domain shuffling. Random mutagenesis of HVR and/or framework residues is described by, for example: Barbas et al. *Proc Nat. Acad. Sci. USA* 91:3809-3813 (1994); Schier et al. Gene 169:147-155 (1995); Yelton et al. *J. Immunol.* 155: 1994-2004 (1995); Jackson et al. *J. Immunol.* 154(7):3310-9 (1995); and Hawkins et al., *J. Mol. Biol.* 226:889-896 (1992).

"Fv" is the minimum antibody fragment which comprises a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the $V_H$ and $V_L$ domains, which enables the sFv to form the desired structure for antigen binding.

Antibody "effector functions" refer to those biological activities attributable to the Fc region (a native sequence Fc region or amino acid sequence variant Fc region) of an antibody, and vary with the antibody isotype.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the present disclosure include human IgG1, IgG2, IgG3 and IgG4.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, Fc=RII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif ("ITAM") in its cytoplasmic domain. Inhibiting receptor FcγRIIB contains an immunoreceptor tyrosine-based inhibition motif ("ITIM") in its cytoplasmic domain. Other FcRs, including those to be identified in the future, are encompassed by the term "FcR" herein. FcRs can also increase the serum half-life of antibodies.

As used herein, "percent (%) amino acid sequence identity" and "homology" with respect to a peptide, polypeptide or antibody sequence refers to the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms known in the art needed to achieve maximal alignment over the full-length of the sequences being compared.

The term "compete" when used in the context of antibodies (e.g., neutralizing antibodies) that compete for the same epitope means competition between antibody as determined by an assay in which the antibody being tested prevents or inhibits (e.g., reduces) specific binding of a reference molecule (e.g., a ligand, or a reference antibody) to a common antigen (e.g., MS4A6A or a fragment thereof). Numerous types of competitive binding assays can be used to determine if antibody competes with another, for example: solid phase direct or indirect radioimmunoassay (RIA), solid phase direct or indirect enzyme immunoassay (EIA), sandwich competition assay (see, e.g., Stahli et al., 1983, *Methods in Enzymology* 9:242-253); solid phase direct biotin-avidin EIA (see, e.g., Kirkland et al., 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using 1-125 label (see, e.g., Morel et al., 1988, Molec. Immunol. 25:7-15); solid phase direct biotin-avidin EIA (see, e.g., Cheung, et al., 1990, Virology 176:546-552); and direct labeled RIA (Moldenhauer et al., 1990, Scand. J. Immunol. 32:77-82). Typically, such an assay involves the use of purified antigen bound to a solid surface or cells bearing either of these, an unlabelled test antibody and a labeled reference antibody. Competitive inhibition is measured by determining the amount of label bound to the solid surface or cells in the presence of the test antibody. Usually the test antibody is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Additional details regarding methods for determining competitive binding are provided in the examples herein. Usually, when a competing antibody is present in excess, it will inhibit (e.g., reduce) specific binding of a reference antibody to a common antigen by at least 20%, 30%, 40%, 50%, 60%, 70%, 80%, 85%, 90%, 95%, 97.5%, and/or near 100%.

As used herein, an "interaction" between a MS4A6A polypeptide and a second polypeptide encompasses, without limitation, protein-protein interaction, a physical interaction, a chemical interaction, binding, covalent binding, and ionic binding. As used herein, an antibody "inhibits interaction" between two polypeptides when the antibody disrupts, reduces, or completely eliminates an interaction between the two polypeptides. An antibody of the present disclosure, thereof, "inhibits interaction" between two polypeptides when the antibody thereof binds to one of the two polypeptides. In some embodiments, the interaction can be inhibited by at least about any of 20%, 30%, 40%, 50%, 60%, 70%, 80%, 85%, 90%, 95%, 97.5%, and/or near 100%.

The term "epitope" includes any determinant capable of being bound by an antibody. An epitope is a region of an antigen that is bound by an antibody that targets that antigen, and when the antigen is a polypeptide, includes specific amino acids that directly contact the antibody. Most often, epitopes reside on polypeptides, but in some instances, can reside on other kinds of molecules, such as nucleic acids. Epitope determinants can include chemically active surface groupings of molecules such as amino acids, sugar side chains, phosphoryl or sulfonyl groups, and can have specific three dimensional structural characteristics, and/or specific charge characteristics. Generally, antibodies specific for a particular target antigen will preferentially recognize an epitope on the target antigen in a complex mixture of polypeptides and/or macromolecules.

An "agonist" antibody or an "activating" antibody is an antibody that induces (e.g., increases) one or more activities or functions of the antigen after the antibody binds the antigen.

An "antagonist" antibody or a "blocking" antibody or an "inhibitory" antibody is an antibody that reduces, inhibits, and/or eliminates (e.g., decreases) antigen binding to one or more ligand after the antibody binds the antigen, and/or that reduces, inhibits, and/or eliminates (e.g., decreases) one or more activities or functions of the antigen after the antibody binds the antigen. In some embodiments, antagonist antibodies, or blocking antibodies, or inhibitory antibodies substantially or completely inhibit antigen binding to one or more ligand and/or one or more activities or functions of the antigen.

An "isolated" antibody, such as an isolated anti-MS4A6A antibody of the present disclosure, is one that has been identified, separated and/or recovered from a component of its production environment (e.g., naturally or recombinantly). Preferably, the isolated antibody is free of association with all other contaminant components from its production environment. Contaminant components from its production environment, such as those resulting from recombinant transfected cells, are materials that would typically interfere with research, diagnostic or therapeutic uses for the antibody, and may include enzymes, hormones, and other proteinaceous or non-proteinaceous solutes. In preferred embodiments, the antibody will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant T-cells since at least one component of the antibody's natural environment will not be present. Ordinarily, however, an isolated polypeptide or antibody will be prepared by at least one purification step.

An "isolated" nucleic acid molecule encoding an antibody, such as an anti-MS4A6A antibody of the present disclosure, is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this disclosure.

"Carriers" as used herein include pharmaceutically acceptable carriers, excipients, or stabilizers that are non-toxic to the cell or mammal being exposed thereto at the dosages and concentrations employed.

As used herein, the term "preventing" includes providing prophylaxis with respect to occurrence or recurrence of a particular disease, disorder, or condition in an individual. An individual may be predisposed to, susceptible to a particular disease, disorder, or condition, or at risk of developing such a disease, disorder, or condition, but has not yet been diagnosed with the disease, disorder, or condition.

As used herein, an individual "at risk" of developing a particular disease, disorder, or condition may or may not have detectable disease or symptoms of disease, and may or may not have displayed detectable disease or symptoms of disease prior to the treatment methods described herein. "At risk" denotes that an individual has one or more risk factors, which are measurable parameters that correlate with development of a particular disease, disorder, or condition, as known in the art. An individual having one or more of these risk factors has a higher probability of developing a particular disease, disorder, or condition than an individual without one or more of these risk factors.

As used herein, the term "treatment" refers to clinical intervention designed to alter the natural course of the individual being treated during the course of clinical pathology. Desirable effects of treatment include decreasing the rate of progression, ameliorating or palliating the pathological state, and remission or improved prognosis of a particular disease, disorder, or condition. An individual is successfully "treated", for example, if one or more symptoms associated with a particular disease, disorder, or condition are mitigated or eliminated.

An "effective amount" refers to at least an amount effective, at dosages and for periods of time necessary, to achieve the desired therapeutic or prophylactic result. An effective amount can be provided in one or more administrations. An effective amount herein may vary according to factors such as the disease state, age, sex, and weight of the individual, and the ability of the treatment to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. An effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

An "individual" for purposes of treatment, prevention, or reduction of risk refers to any animal classified as a mammal, including humans, domestic and farm animals, and zoo, sport, or pet animals, such as dogs, horses, rabbits, cattle, pigs, hamsters, gerbils, mice, ferrets, rats, cats, and the like. In some embodiments, the individual is human.

As used herein, administration "in conjunction" with another compound or composition includes simultaneous administration and/or administration at different times. Administration in conjunction also encompasses administration as a co-formulation or administration as separate compositions, including at different dosing frequencies or intervals, and using the same route of administration or different routes of administration. In some embodiments, administration in conjunction is administration as a part of the same treatment regimen.

The phrase "substantially similar," as used herein, refers to a sufficiently high degree of similarity between two numeric values (generally one associated with a molecule and the other associated with a reference/comparator molecule) such that one of skill in the art would consider the difference between the two values to not be of statistical significance within the context of the biological characteristic measured by said values (e.g., Kd values, protein expression levels). The difference between said two values may be, for example, less than about 20%, less than about 10%, and/or less than about 5% as a function of the reference/comparator value. The phrase "substantially normal" refers to substantially similar to a reference (e.g., normal reference).

The phrase "substantially different," refers to a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values, protein expression levels). The difference between said two values may be, for example, greater than about 10%, greater than about 20%, greater than about 30%, greater than about 40%, and/or greater than about 50% as a function of the value for the reference/comparator molecule.

The "presence," "amount," or "level" of a biomarker associated with an increased clinical benefit to an individual is a detectable level in a biological sample. These can be measured by methods known to one skilled in the art and also disclosed herein. The expression level or amount of biomarker assessed can be used to determine the response to the treatment.

The terms "level of expression" or "expression level" in general are used interchangeably and generally refer to the amount of a biomarker in a biological sample. "Expression" generally refers to the process by which information (e.g., gene-encoded and/or epigenetic) is converted into the structures present and operating in the cell. Therefore, as used herein, "expression" may refer to transcription into a polynucleotide, translation into a polypeptide, or even polynucleotide and/or polypeptide modifications (e.g., posttranslational modification of a polypeptide). Fragments of the transcribed polynucleotide, the translated polypeptide, or polynucleotide and/or polypeptide modifications (e.g., post-translational modification of a polypeptide) shall also be regarded as expressed whether they originate from a transcript generated by alternative splicing or a degraded transcript, or from a post-translational processing of the polypeptide, e.g., by proteolysis. "Expressed genes" include those that are transcribed into a polynucleotide as mRNA and then translated into a polypeptide, and also those that are transcribed into RNA but not translated into a polypeptide (for example, transfer and ribosomal RNAs).

"Elevated expression," "elevated expression levels," or "elevated levels" refers to an increased expression or increased levels of a biomarker or polypeptide in an individual relative to a control, such as an individual or individuals who are not suffering from the disease or disorder (e.g., Alzheimer's disease) or an internal control (e.g., housekeeping biomarker or polypeptide).

"Reduced expression," "reduced expression levels," or "reduced levels" refers to a decrease expression or decreased levels of a biomarker or polypeptide in an individual relative to a control, such as an individual or individuals who are not suffering from the disease or disorder (e.g., Alzheimer's disease) or an internal control (e.g., housekeeping biomarker or polypeptide).

The term "housekeeping biomarker" refers to a biomarker or group of biomarkers (e.g., polynucleotides and/or polypeptides) which are typically similarly present in all cell types. In some embodiments, the housekeeping biomarker is a "housekeeping gene." A "housekeeping gene" refers herein to a gene or group of genes which encode proteins whose activities are essential for the maintenance of cell function and which are typically similarly present in all cell types.

The term "sample," as used herein, refers to a composition that is obtained or derived from a subject and/or individual of interest that contains a cellular and/or other molecular entity that is to be characterized and/or identified, for example based on physical, biochemical, chemical and/or physiological characteristics. For example, the phrase "disease sample" and variations thereof refers to any sample obtained from a subject of interest that would be expected or is known to contain the cellular and/or molecular entity that is to be characterized. Samples include, but are not limited to, primary or cultured cells or cell lines, cell supernatants, cell lysates, platelets, serum, plasma, vitreous fluid, lymph fluid, synovial fluid, follicular fluid, seminal fluid, amniotic fluid, milk, whole blood, blood-derived cells, urine, cerebrospinal fluid, saliva, sputum, tears, perspiration, mucus, tumor lysates, and tissue culture medium, tissue extracts such as homogenized tissue, tumor tissue, cellular extracts, and combinations thereof.

By "tissue sample" or "cell sample" is meant a collection of similar cells obtained from a tissue of a subject or individual. The source of the tissue or cell sample may be solid tissue as from a fresh, frozen and/or preserved organ, tissue sample, biopsy, and/or aspirate; blood or any blood constituents such as plasma; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds which are not naturally intermixed with the tissue in nature such as preservatives, anticoagulants, buffers, fixatives, nutrients, antibiotics, or the like.

A "reference sample", "reference cell", "reference tissue", "control sample", "control cell", or "control tissue", as used herein, refers to a sample, cell, tissue, standard, or level that is used for comparison purposes. In one embodiment, a reference sample, reference cell, reference tissue, control sample, control cell, or control tissue is obtained from a healthy and/or non-diseased part of the body (e.g., tissue or cells) of the same subject or individual. For example, healthy and/or non-diseased cells or tissue adjacent to the diseased cells or tissue (e.g., cells or tissue adjacent to a tumor). In another embodiment, a reference sample is obtained from an untreated tissue and/or cell of the body of the same subject or individual. In yet another embodiment, a reference sample, reference cell, reference tissue, control sample, control cell, or control tissue is obtained from a healthy and/or non-diseased part of the body (e.g., tissues or cells) of an individual who is not the subject or individual. In even another embodiment, a reference sample, reference cell, reference tissue, control sample, control cell, or control tissue is obtained from an untreated tissue and/or cell of the body of an individual who is not the subject or individual.

By "correlate" or "correlating" is meant comparing, in any way, the performance and/or results of a first analysis or protocol with the performance and/or results of a second analysis or protocol. For example, one may use the results of a first analysis or protocol in carrying out a second protocols and/or one may use the results of a first analysis or protocol to determine whether a second analysis or protocol should be performed. With respect to the embodiment of polynucleotide analysis or protocol, one may use the results of the polynucleotide expression analysis or protocol to determine whether a specific therapeutic regimen should be performed.

The term "about" as used herein refers to the usual error range for the respective value readily known to the skilled person in this technical field. Reference to "about" a value or parameter herein includes (and describes) embodiments that are directed to that value or parameter per se.

As used herein and in the appended claims, the singular forms "a," "an," and "the" include plural reference unless the context clearly indicates otherwise. For example, reference to an "antibody" is a reference to from one to many antibodies, such as molar amounts, and includes equivalents thereof known to those skilled in the art, and so forth.

It is understood that aspect and embodiments of the present disclosure described herein include "comprising," "consisting," and "consisting essentially of" aspects and embodiments.

II. Anti-MS4A6A Antibodies

Provided herein are anti-MS4A6A antibodies. Antibodies provided herein are useful, e.g., for the diagnosis or treatment of MS4A6A-associated disorders.

In one aspect, the present disclosure provides isolated (e.g., monoclonal) antibodies that bind to an epitope within a MS4A6A protein of the present disclosure. MS4A6A proteins of the present disclosure include, without limitation, a mammalian MS4A6A protein, human MS4A6A protein, mouse MS4A6A protein, and cyno MS4A6A protein.

Human MS4A6A is a 248-amino acid protein that encodes a membrane glycoprotein. The amino acid sequence of human MS4A6A is set forth in SEQ ID NO:1:

MTSQPVPNETIIVLPSNVINFSQAEKPEPTNQGQDSLKKHLHAEIKVIGT

IQILCGMMVLSLGIILASASFSPNFTQVTSTLLNSAYPFIGPFFFIISGS

LSIATEKRLTKLLVHSSLVGSILSALSALVGFIILSVKQATLNPASLQCE

LDKNNIPTRSYVSYFYHDSLYTTDCYTAKASLAGTLSLMLICTLLEFCLA

VLTAVLRWKQAYSDFPGSVLFLPHSYIGNSGMSSKMTHDCGYEELLTS.

Additionally, the amino acid sequence of mouse ortholog MS4A6D is set forth in SEQ ID NO:2:

MTKPLVHSSLALSILSVLSALTGIAILSVSLAALEPALQQCKLAFTQLDT

TQDAYHFFSPEPLNSCFVAKAALTGVFSLMLISSVLELGLAVLTATLWWK

QSSSAFSGNVIFLSQNSKNKSSVSSESLCNPTYENILTS

Additionally, the amino acid sequence of cynomolgus (cyno) MS4A6A is set forth in SEQ ID NO:3:

MTSQPVPNETMIVLPSNVINFSQAEKPEPTNQGQDSLKKRLQAEVKVIGT

IQILCGVMVLSLGIMLASASFSPNFTQVTSTLLNSAYPFIGPFFFIISGS

LSIATEKKLTKLLVHSSLVGSILSALSALVGFIILSVELAALNPASLQCE

LDKNNIPTRSYVSYYHDSLYTMDCYTVKASLAGPLSLMLICTLLEFCLA

VLTAVLRWKQTVSDFPGSVLFLPHSYIDNSGMSSKMTHGPGYEELLS

In some embodiments, MS4A6A is expressed in a cell. In some embodiments, MS4A6A is expressed in myeloid cells. In some embodiments, MS4A6A is expressed in brain cells. In some embodiments, MS4A6A is expressed in astrocytes, including without limitation mature astrocytes. In some embodiments, MS4A6A is expressed in oligodendrocytes. In some embodiments, MS4A6A is expressed in microglial cells. In some embodiments, MS4A6A is expressed in immune cells, including without limitation, macrophages, eosinophils, mast cells, dendritic cells, natural killer cells, neutrophils, and T cells. In some embodiment, MS4A6A is expressed in olfactory cells. In some embodiments, MS4A6A is expressed on the cell surface.

MS4A6A proteins of the present disclosure include several domains, including without limitation, a cytoplasmic domain (amino acid residues 1-46 of human MS4A6A; see SEQ ID NO:1); a transmembrane domain (amino acid residues 47-67 of human MS4A6A); an extracellular domain (extracellular domain 1; ECL1), corresponding to amino acid residues 68-84 of human MS4A6A; a transmembrane domain (amino acid residues 85-105 of human MS4A6A); a cytoplasmic domain (amino acid residues 106-116 of human MS4A6A); a transmembrane domain (amino acid residues 117-137 of human MS4A6A); an extracellular domain (extracellular domain 2; ECL2), corresponding to amino acid residues 138-185 of human MS4A6A; a transmembrane domain (amino acid residues 186-206 of human MS4A6A); and a cytoplasmic domain (amino acid residues 207-248 of human MS4A6A). Additionally, MS4A6A proteins of the present disclosure are expressed in a number of tissues and cells, including without limitation, the brain, neurons, glial cells, endothelial cells, perivascular cells, pericytes, etc.

MS4A6A Binding Partners and Adaptor Proteins

Further provided herein are methods of screening for anti-MS4A6A antibodies that bind MS4A6A, and that block the interactions between MS4A6A and one or more MS4A6A ligands or binding partners. In some embodiments, a peptide library can be synthesized in which a MS4A6A protein is dissected into consecutive 15-mer and 25-mer peptides separated by one amino acid residue and subsequently spotted onto filters. Binding of a MS4A6A ligand or binding partner can then then tested for its ability to interact with the MS4A6A peptide or with peptides in the presence or absence of anti-MS4A6A antibodies by SPOT binding analysis (e.g., Frank, R and Overwin, H (1996) Methods. Mol. Biol. 66, 149-169; Reineke, U et al., (2002) J. Immunol. Methods 267, 13-26; and Andersen, O S et al., (2010) J, BIOLOGICAL CHEMISTRY 285, 12210-12222). In some embodiments, a cellulose support can be prepared as an N-modified cellulose-aminohydroxylpropyl ether membrane, and all rounds of synthesis are started with spot definition by 9-fluorenylmethoxycar-bonyalanine-pentafluoophenyl ester that creates an alanine linker between peptide and membrane. For example, an automated linear synthesis of stepwise addition of the different amino acids protected at their N-terminal by 9-fluorenyl-methoxycarbonyl and appropriate side-chain protection for the growing peptide chain. In some embodiments, the pattern of de-protection, activation, and coupling is continued until 16-mer peptides are produced, resulting in an equally distributed array of covalently anchored peptides to the cellulose support at their C-terminal ends with N-terminal free ends (Scharn, D et al., (2000) J. Comb. Chem. 2, 361-369). In some embodiments, removal of the side protection group can be performed in two steps. First, the membrane can be treated with 90% trifluoroacetic acid (in dichlormethane, containing 3% triisobutylsilane and 2% H2O); and secondly with, for example, 60% trifluoroacetic acid (in dichlormethane, containing 3% triisobutylsilane and 2% H2O). To remove trifluoroacetic acid salts, the membrane can be washed several times with $H_2O$, ethanol, Tris-buffered saline, and ethanol, and then dried. Finally, the membrane is blocked in blocking buffer dilated in Tris-buffered saline (pH 8.0) and supplemented with 5% sac-charose for 2 h before the predefined peptide library is ready for ligand binding analysis. In some embodiments, for binding studies of cellulose-bound peptides, membrane-bound libraries can be incubated with combined S-peptide and polyhistidine-tagged In some embodiments, the interaction between MS4A6A and MS4A6A ligands and binding partners may be characterized using cellulose-bound proteins (e.g., Andersen et al., 2010, J Biol Chem, 285,12210-12222). For example, membrane-bound proteins can be incubated with another MS4A6A ligand or binding partner; in blocking buffer overnight at 4° C., followed by a second incubation with 1 µg/ml of HRP-conjugated S-protein also in blocking buffer but for 3 hours at room temperature. Subsequently, the membrane may be washed three times for 10 minutes with Tris-buffered saline before quantitative characterization of bound ligand is carried out using the UptiLight chemiluminescence substrate and a LumiImager instrument, providing the spot signal intensities in Boehringer light units. Alternatively, detection of bound ligand can be performed by an immunochemical assay with an antibody against the histidine tag and a secondary HRP-conjugated anti-mouse antibody. Incubations can be followed by standard Western blotting analysis and spot detection.

In some embodiments, the interaction between MS4A6A and MS4A6A ligands and binding partners may be characterized using a proximity ligation assay (e.g., Gustafsen et al., 2013 The Journal of Neuroscience, 33:64-71). For example, proximity ligation assay (PLA) (DuolinkII) on cells expressing or exposed to MS4A6A and its ligand or binding partner can be performed with the primary antibodies anti-MS4A6A, and antibodies against the binding partner, followed by incubation with secondary antibodies conjugated to oligonucleotides, which hybridize to subsequently added circle-forming oligonucleotides and prime a rolling circle amplification when the antigens are located within proximity of 40 nm. The amplified DNA can be visualized by addition of complementary fluorescent-labeled oligonucleotides.

In some embodiments, the interaction between MS4A6A and MS4A6A ligands and binding partners may be characterized using alkaline phosphatase-tagged ligands in cell binding assays (e.g., Hu et al., 2005, J. Neurosci. 25, 5298-5304; Fournier et al., 2001, Nature 409, 341-346; Lauren et al., 2009, Nature 457, 1128-1132; and Hu et al., 2010, Neuron 68, 654-667). For example, alkaline phosphatase (AP)-tagged ligands can be made to assess binding to MS4A6A on transfected cells or primary neurons. To detect AP tagged ligand binding to cells expressing MS4A6A, cultures can be washed with, for example, Hanks balanced salt solution containing 20 mM sodium HEPES, pH 7.05, and 1 mg/ml bovine serum albumin (BSA) (HBH). Then, the plates can be incubated with AP tagged ligands in the presence or absence of MS4A6A blocking antibodies, for example, in HBH for 2 h at 23° C. AP bound ligand can be detected and quantified according to methods well-known in the art.

In certain embodiments that may be combined with any of the preceding embodiments, the anti-MS4A6A antibody further inhibits interaction between MS4A6A and one or more of its ligands, signaling proteins or binding proteins by: a) reducing the effective levels of MS4A6A available for interacting with the one or more ligands or binding proteins; b); blocking one or more of the sites on MS4A6A required for interaction with the one or more ligands or binding proteins; c) preventing one or more posttranslational events on MS4A6A that are required for interaction with the one or more ligands or binding proteins and/or for correct processing and/or subcellular localization of MS4A6A; d) inducing degradation of MS4A6A; e) changing the conformation of MS4A6A, or any combination thereof.

In certain embodiments that may be combined with any of the preceding embodiments, the anti-MS4A6A antibody further increases or enhances interaction between MS4A6A and one or more of its ligands, signaling proteins or binding proteins by: a) increasing the effective levels of MS4A6A available for interacting with the one or more ligands or binding proteins; b); increasing one or more of the sites on MS4A6A required for interaction with the one or more ligands or binding proteins; c) increasing one or more posttranslational events on MS4A6A that are required for interaction with the one or more ligands or binding proteins and/or for correct processing and/or subcellular localization of MS4A6A; d) preventing degradation of MS4A6A; e) changing the conformation of MS4A6A, or any combination thereof.

In certain embodiments that may be combined with any of the preceding embodiments, the anti-MS4A6A antibody binds specifically to human MS4A6A, mouse MS4A6A, cyno MS4A6A, or a combination thereof. In certain embodiments that may be combined with any of the preceding embodiments, the anti-MS4A6A antibody is a human antibody, a humanized antibody, a bispecific antibody, a monoclonal antibody, a multivalent antibody, a conjugated antibody, or a chimeric antibody. In certain embodiments that may be combined with any of the preceding embodiments, the anti-MS4A6A antibody is a bispecific antibody recognizing a first antigen and a second antigen. In certain embodiments that may be combined with any of the preceding embodiments, the first antigen is MS4A6A and the second antigen is an antigen facilitating transport across the blood-brain-barrier. In certain embodiments that may be combined with any of the preceding embodiments, the second antigen is selected from the group consisting of MS4A6A, transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopep peptide, basigin, Glut1, and CD98hc, and ANG1005.

Signal transduction adaptor proteins are, without limitation, proteins that are accessory to other proteins associated with a signal transduction pathway. Adaptor proteins contain various protein-binding modules or motifs that link or protein-binding partners together and facilitate the creation of larger signaling complexes. Adaptor proteins often contain several domains within their structure that allow specific interactions with one or more other specific proteins. For example, Src homology 2 (SH2) domains recognize specific amino acid residue sequences within proteins containing phosphotyrosine residues. The interaction of adaptor proteins and other signaling proteins allows for a diversity of specific and coordinated protein-protein interactions to occur within a cell during and associated with signal transduction.

An immunoreceptor tyrosine-based activation motif (ITAM) is a conserved sequence of four amino acid residues that is repeated twice in the cytoplasmic tails of certain cell surface proteins of the immune system. The consensus motif is YxxI/Lx$_{(6-12)}$YxxI/L (SEQ ID NO: 128) in the C-terminus of certain proteins. The two repeats are typically separated by between 6 and 12 amino acid residues (YxxL/Ix$_{(6-12)}$ YxxL/I (SEQ ID NO: 128)). ITAMs are important for signal transduction; the tyrosine residues within these motifs are phosphorylated following interaction of receptor molecules with their ligands and form docking sites for other proteins involved in signal transduction (Barrow and Trowsdale, 2006, Eur J Immunol, 36:1646-1653).

An immunoreceptor tyrosine-based inhibition motif (ITIM) is a conserved sequence of amino acids (S/I/V/ LxYxxI/V/L (SEQ ID NO: 127)) that is found in the cytoplasmic tails of certain inhibitory receptors of the immune system. After ITIM-containing inhibitory receptors interact with their ligand, their ITIM motif becomes phosphorylated by enzymes of the Src kinase family, allowing them to recruit other enzymes (such as various phosphotyrosine phosphatases), which decrease the activation of molecules involved in signal transduction. (Barrow and Trowsdale, 2006, Eur J Immunol, 36:1646-1653).

Alternatively, some receptors have no intrinsic ITAM motif, but instead encode positively charged transmembrane amino acids, such as lysine or arginine. These positively charged amino acid residues mediate association with corresponding negatively charged transmembrane amino acid residues of ITAM-encoding adaptor proteins. Upon ligand recognition and receptor clustering, tyrosine amino acid residues are phosphorylated by Src family protein tyrosine kinase (PTK). Dual-phosphorylated ITAM motifs serve as docking sites for the tandem SH2 domains of Syk family PTK, such as ZAP-70 or Syk. Syk family PTK phosphorylate a series of intracellular substrates, leading to the formation of membrane-proximal scaffolds, resulting to recruitment of important effector molecules, such as phospholipase C-c (PLCc), leading to calcium signaling, as well as Ras activation, which results in stimulation of the ERK pathway and cellular activation.

Studies support the importance of MS4A proteins in forming signaling complexes with other cell surface membrane proteins that modulate or propagate downstream biochemical signals. Although binding partners have, in most instances, yet to be clearly determined for MS4A proteins other than MS4A1 and MS4A2, predictive protein analyses show that Src homology 2(SH2) and SH3 domain-binding sites are commonly found on the N- and C-terminal regions of MS4A proteins, which may serve as docking platforms for other signaling molecules (Dinkel et al., 2012, Nucl Acids Res, 40: DD242-D251) SH domains bind preferentially to proline-rich sequences, which are also commonly found in the cytoplasmic tails of MS4A proteins (Liang and Tedder, 2001, Genomics, 72:119-127; Kay et al., 2000, FASEB J, 14:231-241). This feature of MS4A proteins provides a ligands in the presence or absence of anti-MS4A6A antibodies, for example, in blocking buffer overnight at 4° C., followed by a second incubation with 1 mg/ml of HRP-conjugated S-protein also in blocking buffer but for 3 h at room temperature. Subsequently, the membrane can be washed, for example, three times for 10 min with Tris-buffered saline before quantitative characterization of bound ligand may be carried out using the UptiLight chemiluminescence substrate and a LumiImager instrument, providing the spot signal intensities in Boehringer light units. Alternatively, detection of bound ligand can be performed by an immunochemical assay with an antibody against a histidine tag from and a secondary HRP-conjugated anti-mouse antibody. Incubations can be performed utilizing standard Western blotting procedures and spot detection.

Further provided herein are methods of screening for anti-MS4A6A antibodies that block interactions (e.g., binding) MS4A6A and one or more MS4A6A ligands or binding partners.

In some embodiments, the interaction between MS4A6A and MS4A6A ligands or binding partners may be characterized using surface Plasmon resonance analysis (e.g., Skeldal et al., 2012 J Biol Chem., 287:43798; and Andersen et al., 201, J Biol Chem, 285,12210-12222). Determination of direct binding of MS4A6A ligand or binding partner to immobilized MS4A6A in the presence or absence of blocking anti-MS4A6A antibodies can be performed, for example, on a Biacore2000 instrument (Biacore, Sweden) using CaHBS as standard running buffer (10 mM HEPES, pH 7.4, 140 mM NaCl, 2 mM $CaCl_2$, 1 mM EGTA, and 0.005% Tween 20). In some embodiments, a biosensor chip from Biacore (CM5) can be activated using the NHS/EDC method followed by coating with MS4A6A to a protein density of 79 fmol/$mm^2$ and used for affinity measurements of the binding partner. Preparation of a biosensor surface with pro-MS4A6A will follow an equal procedure. Regeneration of the flow cell after each cycle of ligand binding experiment can be done by two 10- µl pulses of regeneration buffer (10 mM glycine-HCl, pH 4.0, 500 mM NaCl, 20 mM EDTA, and 0.005% Tween 20) and a single injection of 0.001% SDS. Fitting of sensorgrams for affinity estimations can be done, for example, by using BIAevaluation version 3.1. Following similar protocols, immobilization of HisS-NGFpro or HisS-BDNFpro may also done on a CM5 biosensor chip using the NHS/EDC coupling kit, giving similar surface densities of immobilized protein (~300 fmol/$mm^2$). A biosensor chip with immobilized with a MS4A6A ligand or binding partner can also be used to examine the binding of MS4A6A in the absence or presence of competing MS4A6A antibodies.

In some embodiments, the interaction between MS4A6A and MS4A6A ligands and binding partners can be characterized using a pulldown assay (e.g., Andersen et al., 2010, J Biol Chem, 285,12210-12222). For example, expressed intracellular or extracellular domains of MS4A6A can be incubated with tagged MS4A6A ligands or binding partners in the absence or presence of MS4A6A blocking antibodies and are precipitated using 100 µl of glutathione (GSH)-Sepharose beads (Amersham Biosciences, catalog no. 17-0756-01). The amount of applied receptor domains can be determined by precipitation using Talon beads as control. Bound proteins can be separated by SDS-PAGE analysis and visualized using anti-histidine antibody by standard Western blotting analysis.

Strong basis for their being intimately involved in protein-protein interactions and may also associated with one another to form signaling complexes.

Accordingly, in some embodiments, an anti-MS4A6A antibody of the present disclosure enhances or increases the formation of signaling complexes. In some embodiments, an anti-MS4A6A antibody of the present disclosure enhances or increases the formation of signaling complexes associated with ITAM-encoding adaptor proteins. In some embodiments, an anti-MS4A6A antibody of the present disclosure enhances or increases the formation of inhibitory signaling complexes. In some embodiments, an anti-MS4A6A antibody of the present disclosure enhances or increases the formation of inhibitory signaling complexes associated with ITIM-encoding adaptor proteins.

In some embodiments, an anti-MS4A6A antibody of the present disclosure inhibits (e.g., blocks) or reduces the formation of signaling complexes. In some embodiments, an anti-MS4A6A antibody of the present disclosure inhibits (e.g., blocks) or reduces the formation of signaling complexes associated with ITAM-encoding adaptor proteins. In some embodiments, an anti-MS4A6A antibody of the present disclosure inhibits (e.g., blocks) or reduces the formation of inhibitory signaling complexes. In some embodiments, an anti-MS4A6A antibody of the present disclosure inhibits (e.g., blocks) or reduces the formation of inhibitory signaling complexes associated with ITIM-encoding adaptor proteins.

In some embodiments that may be combined with any of the preceding embodiments, an anti-MS4A6A antibody of the present disclosure inhibits (e.g., blocks) or reduces formation of MS4A6A homo-oligomeric cell surface protein complexes by: a) reducing the effective levels of MS4A6A available for MS4A6A homo-oligomeric complex formation; b) blocking one or more of the sites on MS4A6A required for MS4A6A homo-oligomeric complex formation; c) preventing one or more posttranslational events on MS4A6A that are required for MS4A6A homo-oligomeric complex formation and/or for correct processing and/or cellular localization of MS4A6A; d) inducing degradation of MS4A6A; e) changing the conformation of MS4A6A, or any combination thereof.

In some embodiments that may be combined with any of the preceding embodiments, an anti-MS4A6A antibody of the present disclosure increases or enhances formation of MS4A6A homo-oligomeric cell surface protein complexes by: a) increasing the effective levels of MS4A6A available for MS4A6A homo-oligomeric complex formation; b) stabilizing one or more of the sites on MS4A6A required for MS4A6A homo-oligomeric complex formation; c) maintaining cell surface expression of MS4A6A to allow for homo-oligomeric complex formation and/or for correct processing and/or maintaining correct cellular localization of MS4A6A; d) reducing degradation of MS4A6A; e) changing the conformation of MS4A6A, or any combination thereof.

In some embodiments that may be combined with any of the preceding embodiments, an anti-MS4A6A antibody of the present disclosure inhibits (e.g., blocks) or reduces MS4A6A hetero-oligomeric cell surface protein complex formation with one or more signal transduction adaptor proteins by: a) reducing the effective levels of MS4A6A available for MS4A6A hetero-oligomeric complex formation; b); blocking one or more of the sites on MS4A6A required for MS4A6A hetero-oligomeric complex formation; c) preventing one or more posttranslational events on MS4A6A that are required for MS4A6A hetero-oligomeric complex formation and/or for correct processing and/or cellular localization of MS4A6A; d) inducing degradation of MS4A6A; e) changing the conformation of MS4A6A, or any combination thereof.

In some embodiments that may be combined with any of the preceding embodiments, an anti-MS4A6A antibody of the present disclosure increases or enhances MS4A6A hetero-oligomeric cell surface protein complex formation with one or more signal transduction adaptor proteins by: a) increasing the effective levels of MS4A6A available for MS4A6A hetero-oligomeric complex formation; b) stabilizing one or more of the sites on MS4A6A required for MS4A6A hetero-oligomeric complex formation; c) maintaining cell surface expression of MS4A6A to allow for MS4A6A hetero-oligomeric complex formation and/or for correct processing and/or maintaining correct cellular localization of MS4A6A; d) reducing degradation of MS4A6A; e) changing the conformation of MS4A6A, or any combination thereof.

In some embodiments that may be combined with any of the preceding embodiments, an anti-MS4A6A antibody of the present disclosure increases or enhances MS4A6A receptor clustering. In some embodiments that may be combined with any of the preceding embodiments, an anti-MS4A6A antibody of the present disclosure inhibits or reduces MS4A6A receptor clustering. In some embodiments, the increase or enhancement of, or the inhibition or reduction of, MS4A6A receptor clustering is in a myeloid cell.

Agonist Antibodies

Anti-MS4A6A antibodies of the present disclosure generally bind to one or more MS4A6A proteins expressed in a cell. One class of antibodies of the present disclosure is agonist antibodies. For example, the MS4A6A receptor may require clustering on the cell surface in order to transduce a signal. Thus agonist antibodies may have unique features to stimulate, for example, the MS4A6A receptor. For example, they may have the correct epitope specificity that is compatible with receptor activation, as well as the ability to induce or retain receptor clustering on the cell surface. An anti-MS4A6A agonist antibody of the present disclosure increases or enhances MS4A6A function or activity, such as, for example, by increasing MS4A6A protein expression, by increasing MS4A6A protein levels, by correcting improper cellular localization, or by increasing or restoring cell surface expression.

In vivo, antibodies may cluster receptors by multiple potential mechanisms. Some isotypes of human antibodies such as IgG2 have, due to their unique structure, an intrinsic ability to cluster receptors, or retain receptors in a clustered configuration, thereby activating receptors such as MS4A6A without binding to an Fc receptor (e.g., White et al., (2015) Cancer Cell 27, 138-148).

Other antibodies cluster receptors (e.g., MS4A6A) by binding to Fcg receptors on adjacent cells. Binding of the constant IgG Fc part of the antibody to Fcg receptors leads to aggregation of the antibodies, and the antibodies in turn aggregate the receptors to which they bind through their variable region (Chu et al. (2008) Mol Immunol, 45:3926-3933; and Wilson et al., (2011) Cancer Cell 19, 101-113). Binding to the inhibitory Fcg receptor FcgR (FcgRIIB) that does not elicit cytokine secretion, oxidative burst, increased phagocytosis, and enhanced antibody-dependent, cell-mediated cytotoxicity (ADCC) is often a preferred way to cluster antibodies in vivo, since binding to FcgRIIB is not associated with immune adverse effects.

Other mechanisms may also be used to cluster receptors (e.g., MS4A6A). For example, antibody fragments (e.g., Fab fragments) that are cross-linked together may be used to cluster receptors (e.g., MS4A6A) in a manner similar to antibodies with Fc regions that bind Fcg receptors, as described above. Without wishing to be bound to theory, it is thought that cross-linked antibody fragments (e.g., Fab fragments) may function as agonist antibodies if they induce receptor clustering on the cell surface and bind an appropriate epitope on the target (e.g., MS4A6A).

Therefore, in some embodiments, antibodies that bind a MS4A6A protein may include agonist antibodies that due to their epitope specificity bind MS4A6A and activate one or more MS4A6A activities. Without wishing to be bound to theory, such antibodies may bind to the ligand-binding site on the target antigen (e.g., MS4A6A) and mimic the action of a natural ligand, or stimulate the target antigen to transduce signal by binding to one or more domains that are not the ligand-binding sites. Such antibodies would not interfere with ligand binding and may act additively or synergistically with the natural ligands.

In some embodiments, an anti-MS4A6A antibody of the present disclosure is an agonist antibody that induces or increases one or more MS4A6A activities. In some embodiments the anti-MS4A6A antibody induces or increases one or more activities of MS4A6A protein expressed in a cell. In some embodiments, an anti-MS4A6A antibody of the present disclosure is an agonist antibody that increases cell surface expression of MS4A6A. In some embodiments, an anti-MS4A6A antibody of the present disclosure is an agonist antibody that corrects improper cellular localization of MS4A6A. In some embodiments, an anti-MS4A6A antibody of the present disclosure is an agonist antibody that increases or restores cell-surface targeting or localization of MS4A6A protein. In some embodiments, an anti-MS4A6A antibody of the present disclosure is an agonist antibody that increases or restores cell surface expression of MS4A6A protein.

Inert antibodies

Another class of antibodies of the present disclosure includes inert antibodies. As used herein, "inert" antibodies refer to antibodies that specifically bind their target antigen but do not modulate (e.g., decrease/inhibit or activate/induce) antigen function. For example, in the case of MS4A6A, inert antibodies do not modulate ligand binding and/or MS4A6A activities. Without wishing to be bound to theory, it is thought that antibodies that do not have the ability to cluster MS4A6A on the cell surface may be inert antibodies even if they have an epitope specificity that is compatible with receptor activation.

In some embodiments, antibodies that bind a MS4A6A protein may include antibodies that bind MS4A6A but, due to their epitope specificity, do not modulate protein function. Such functionally inert antibodies can be used as cargo to transport toxins as described for the CD33 antibody Gemtuzumab zogamicin, (marketed as Mylotarg) which is conjugated to the cytotoxic agent from the class of calicheamicins and is used to target and kill acute myelogenous leukemia tumors (Naito et al., (2000), Leukemia, 14, 1436-1443; Ricart (2011) Clin Cancer Res 17; 6417-6436; Hamann et al., (2002) Journal: Bioconjugate Chemistry, 13, 47-58; and Beitz et al., (2001) Clin Cancer Res 7; 1490-6.). Therefore, in some embodiments, antibodies of the present disclosure are inert antibodies that bind MS4A6A but are incapable of inducing one or more MS4A6A activities (e.g., a MS4A6A activity described herein).

Calcium Influx

Cell lines transfected with MS4A1 showed an increased calcium conductance across the plasma membrane, suggesting that MS4A1 functions as an important channel for regulating calcium homeostasis. (Parolini et al., 2012, Int J Biochem Cell Biol, 44:2095-2105; Li et al., 2003, J Biol Chem, 278:42427-42434) MS4A proteins are thus involved in the control of intracellular free calcium concentration by regulating (e.g., increasing) calcium influx and/or by mobilizing calcium from intracellular stores (Ishibashi et al., 2001, Gene, 264:87-93). Due to the conservation in protein structure within the MS4A family, other MS4A proteins (e.g., MS4A4A and MS4A6A) may share overlapping calcium regulatory functions (Ma et al., 2015, Mol Neurobiol, 51:1240-1248). Accordingly, in some embodiments, an anti-MS4A6A antibody of the present disclosure modulates calcium levels in a cell, calcium influx, and/or calcium mobilization from intracellular stores. In some embodiments, an anti-MS4A6A antibody of the present disclosure increases calcium influx in a cell and/or increases calcium mobilization in a cell from intracellular stores. In some embodiments, an anti-MS4A6A antibody of the present disclosure reduces calcium influx in a cell and/or reduces calcium mobilization in a cell from intracellular stores.

Additionally, members of the MS4A protein family are chemoreceptors expressed within necklace olfactory sensory neurons. Results support a model in which MS4A receptors bind inhaled odorants and induce calcium influx into necklace olfactory sensory neurons, supporting a role of MS4A family members in regulating calcium influx in various cells (Greer et al., 2016, Cell, 165:1734-1748).

A. Exemplary Antibodies and Certain Other Antibody Embodiments

In some embodiments, provided herein are anti-MS4A6A antibodies comprising at least one, two, three, four, five, or six HVRs selected from: (a) HVR-H1 comprising an amino acid sequence selected from the group consisting of SEQ ID NOs:4, 5, 6, 7, 8, 9, 10, 11, 12, 13, 14, 15, and 16; (b) HVR-H2 comprising an amino acid sequence selected from the group consisting of SEQ ID NOs:17, 18, 19, 20, 21, 22, 23, 24, 25, 26, 27, 28, 29, 30, and 31; (c) HVR-H3 comprising an amino acid sequence selected from the group consisting of SEQ ID NOs:32, 33, 34, 35, 36, 37, 38, 39, 40, 41, 42, 43, 44, and 45; (d) HVR-L1 comprising an amino acid sequence selected from the group consisting of SEQ ID NOs:46, 47, 48, 49, 50, 51, 52, 53, 54, 55, 56, 57, 58, 59, and 60; (e) HVR-L2 comprising an amino acid sequence selected from the group consisting of SEQ ID NOs:61, 62, 63, 64, 65, 66, 67, 68, 69, 70, 71, 72, 73, 74, 75, and 76; and (f) HVR-L3 comprising an amino acid sequence selected from the group consisting of SEQ ID NOs:77, 78, 79, 80, 81, 82, 83, 84, 85, 86, 87, 88, 89, and 90.

In some embodiments, provided herein are anti-MS4A6A antibodies comprising at least one, two, three, four, five, or six HVRs selected from: (a) HVR-H1 comprising the amino acid sequence of SEQ ID NO:4; (b) HVR-H2 comprising the amino acid sequence of SEQ ID NO:17; (c) HVR-H3 comprising the amino acid sequence of SEQ ID NO:32; (d) HVR-L1 comprising the amino acid sequence of SEQ ID NO:46; (e) HVR-L2 comprising the amino acid sequence of SEQ ID NO:61; and (f) HVR-L3 comprising the amino acid sequence of SEQ ID NO:77; (a) HVR-H1 comprising the amino acid sequence of SEQ ID NO:5; (b) HVR-H2 comprising the amino acid sequence of SEQ ID NO:18; (c) HVR-H3 comprising the amino acid sequence of SEQ ID NO:33; (d) HVR-L1 comprising the amino acid sequence of SEQ ID NO:47; (e) HVR-L2 comprising the amino acid sequence of SEQ ID NO:62; and (f) HVR-L3 comprising the amino acid sequence of SEQ ID NO:78; (a) HVR-H1 comprising the amino acid sequence of SEQ ID NO:6; (b) HVR-H2 comprising the amino acid sequence of SEQ ID NO:19; (c) HVR-H3 comprising the amino acid sequence of SEQ ID NO:34; (d) HVR-L1 comprising the amino acid sequence of SEQ ID NO:48; (e) HVR-L2 comprising the amino acid sequence of SEQ ID NO:63; and (f) HVR-L3 comprising the amino acid sequence of SEQ ID NO:79; (a) HVR-H1 comprising the amino acid sequence of SEQ ID NO:7; (b) HVR-H2 comprising the amino acid sequence of SEQ ID NO:20; (c) HVR-H3 comprising the amino acid sequence of SEQ ID NO:35; (d) HVR-L1 comprising the amino acid sequence of SEQ ID NO:49; (e) HVR-L2 comprising the amino acid sequence of SEQ ID NO:64; and (f) HVR-L3 comprising the amino acid sequence of SEQ ID NO:80; (a) HVR-H1 comprising the amino acid sequence of SEQ ID NO:8; (b) HVR-H2 comprising the amino acid sequence of SEQ ID NO:21; (c) HVR-H3 comprising the amino acid sequence of SEQ ID NO:36; (d) HVR-L1 comprising the amino acid sequence of SEQ ID NO:50; (e) HVR-L2 comprising the amino acid sequence of SEQ ID NO:65; and (f) HVR-L3 comprising the amino acid sequence of SEQ ID NO:81; (a) HVR-H1 comprising the amino acid sequence of SEQ ID NO:9; (b) HVR-H2 comprising the amino acid sequence of SEQ ID NO:22; (c) HVR-H3 comprising the amino acid sequence of SEQ ID NO:37; (d) HVR-L1 comprising the amino acid sequence of SEQ ID NO:51; (e) HVR-L2 comprising the amino acid sequence of SEQ ID NO:66; and (f) HVR-L3 comprising the amino acid sequence of SEQ ID NO:82; (a) HVR-H1 comprising the amino acid sequence of SEQ ID NO:10; (b) HVR-H2 comprising the amino acid sequence of SEQ ID NO:23; (c) HVR-H3 comprising the amino acid sequence of SEQ ID NO:38; (d) HVR-L1 comprising the amino acid sequence of SEQ ID NO:52; (e) HVR-L2 comprising the amino acid sequence of SEQ ID NO:67; and (f) HVR-L3 comprising the amino acid sequence of SEQ ID NO:83; (a) HVR-H1 comprising the amino acid sequence of SEQ ID NO:11; (b) HVR-H2 comprising the amino acid sequence of SEQ ID NO:24; (c) HVR-H3 comprising the amino acid sequence of SEQ ID NO:39; (d) HVR-L1 comprising the amino acid sequence of SEQ ID NO:53; (e) HVR-L2 comprising the amino acid sequence of SEQ ID NO:68; and (f) HVR-L3 comprising the amino acid sequence of SEQ ID NO:84; (a) HVR-H1 comprising the amino acid sequence of SEQ ID NO:8; (b) HVR-H2 comprising the amino acid sequence of SEQ ID NO:25; (c) HVR-H3 comprising the amino acid sequence of SEQ ID NO:40; (d) HVR-L1 comprising the amino acid sequence of SEQ ID NO:54; (e) HVR-L2 comprising the amino acid sequence of SEQ ID NO:69; and (f) HVR-L3 comprising the amino acid sequence of SEQ ID NO:85; (a) HVR-H1 comprising the amino acid sequence of SEQ ID NO:11; (b) HVR-H2 comprising the amino acid sequence of SEQ ID NO:26; (c) HVR-H3 comprising the amino acid sequence of SEQ ID NO:39; (d) HVR-L1 comprising the amino acid sequence of SEQ ID NO:53; (e) HVR-L2 comprising the amino acid sequence of SEQ ID NO:70; and (f) HVR-L3 comprising the amino acid sequence of SEQ ID NO:84; (a) HVR-H1 comprising the amino acid sequence of SEQ ID NO:4; (b) HVR-H2 comprising the amino acid sequence of SEQ ID NO:17; (c) HVR-H3 comprising the amino acid sequence of SEQ ID NO:32; (d) HVR-L1 comprising the amino acid sequence of SEQ ID NO:46; (e) HVR-L2 comprising the amino acid sequence of SEQ ID NO:61; and (f) HVR-L3 comprising the amino acid sequence of SEQ ID NO:77; (a) HVR-H1 comprising the amino acid sequence of SEQ ID NO:12; (b) HVR-H2 comprising the amino acid sequence of SEQ ID NO:27; (c) HVR-H3 comprising the amino acid sequence of SEQ ID NO:41; (d) HVR-L1 comprising the amino acid sequence of SEQ ID NO:55; (e) HVR-L2 comprising the amino acid sequence of SEQ ID NO:71; and (f) HVR-L3 comprising the amino acid sequence of SEQ ID NO:86; (a) HVR-H1 comprising the amino acid sequence of SEQ ID NO:13; (b) HVR-H2 comprising the amino acid sequence of SEQ ID NO:28; (c) HVR-H3 comprising the amino acid sequence of SEQ ID NO:42; (d) HVR-L1 comprising the amino acid sequence of SEQ ID NO:56; (e) HVR-L2 comprising the amino acid sequence of SEQ ID NO:72; and (f) HVR-L3 comprising the amino acid sequence of SEQ ID NO:87; (a) HVR-H1 comprising the amino acid sequence of SEQ ID NO:14; (b) HVR-H2 comprising the amino acid sequence of SEQ ID NO:29; (c) HVR-H3 comprising the amino acid sequence of SEQ ID NO:43; (d) HVR-L1 comprising the amino acid sequence of SEQ ID NO:57; (e) HVR-L2 comprising the amino acid sequence of SEQ ID NO:73; and (f) HVR-L3 comprising the amino acid sequence of SEQ ID NO:84; (a) HVR-H1 comprising the amino acid sequence of SEQ ID NO:11; (b) HVR-H2 comprising the amino acid sequence of SEQ ID NO:24; (c) HVR-H3 comprising the amino acid sequence of SEQ ID NO:39; (d) HVR-L1 comprising the amino acid sequence of SEQ ID NO:53; (e) HVR-L2 comprising the amino acid sequence of SEQ ID NO:68; and (f) HVR-L3 comprising the amino acid sequence of SEQ ID NO:84; (a) HVR-H1 comprising the amino acid sequence of SEQ ID NO:15; (b) HVR-H2 comprising the amino acid sequence of SEQ ID NO:30; (c) HVR-H3 comprising the amino acid sequence of SEQ ID NO:44; (d) HVR-L1 comprising the amino acid sequence of SEQ ID NO:58; (e) HVR-L2 comprising the amino acid sequence of SEQ ID NO:74; and (f) HVR-L3 comprising the amino acid sequence of SEQ ID NO:88; (a) HVR-H1 comprising the amino acid sequence of SEQ ID NO:6; (b) HVR-H2 comprising the amino acid sequence of SEQ ID NO:19; (c) HVR-H3 comprising the amino acid sequence of SEQ ID NO:34; (d) HVR-L1 comprising the amino acid sequence of SEQ ID NO:59; (e) HVR-L2 comprising the amino acid sequence of SEQ ID NO:75; and (f) HVR-L3 comprising the amino acid sequence of SEQ ID NO:89; (a) HVR-H1 comprising the amino acid sequence of SEQ ID NO:6; (b) HVR-H2 comprising the amino acid sequence of SEQ ID NO:19; (c) HVR-H3 comprising the amino acid sequence of SEQ ID NO:34; (d) HVR-L1 comprising the amino acid sequence of SEQ ID NO:48; (e) HVR-L2 comprising the amino acid sequence of SEQ ID NO:63; and (f) HVR-L3 comprising the amino acid sequence of SEQ ID NO:79; (a) HVR-H1 comprising the amino acid sequence of SEQ ID NO:16; (b) HVR-H2 comprising the amino acid sequence of SEQ ID NO:31; (c) HVR-H3 comprising the amino acid sequence of SEQ ID NO:45; (d) HVR-L1 comprising the amino acid sequence of SEQ ID NO:60; (e) HVR-L2 comprising the amino acid sequence of SEQ ID NO:76; and (f) HVR-L3 comprising the amino acid sequence of SEQ ID NO:90; and (a) HVR-H1 comprising the amino acid sequence of SEQ ID NO:16; (b) HVR-H2 comprising the amino acid sequence of SEQ ID NO:31; (c) HVR-H3 comprising the amino acid sequence of SEQ ID NO:45; (d) HVR-L1 comprising the amino acid sequence of SEQ ID NO:60; (e) HVR-L2 comprising the amino acid sequence of SEQ ID NO:76; and (f) HVR-L3 comprising the amino acid sequence of SEQ ID NO:90.

In some embodiments, provided herein are anti-MS4A6A antibodies comprising at least one, at least two, or all three $V_H$ HVR sequences selected from (a) HVR-H1 comprising an amino acid sequence selected from the group consisting of SEQ ID NO: 4, 5, 6, 7, 8, 9, 10, 11, 12, 13, 14, 15, and 16; (b) HVR-H2 comprising an amino acid sequence selected from the group consisting of SEQ ID NO: 17, 18, 19, 20, 21, 22, 23, 24, 25, 26, 27, 28, 29, 30, and 31; and (c) HVR-H3 comprising an amino acid sequence selected from the group consisting of SEQ ID NO: 32, 33, 34, 35, 36, 37, 38, 39, 40, 41, 42, 43, 44, and 45.

In some embodiments, provided herein are anti-MS4A6A antibodies comprising at least one, at least two, or all three $V_L$ HVR sequences selected from (a) HVR-L1 comprising an amino acid sequence selected from the group consisting of SEQ ID NO: 46, 47, 48, 49, 50, 51, 52, 53, 54, 55, 56, 57, 58, 59, and 60; (e) HVR-L2 comprising an amino acid sequence selected from the group consisting of SEQ ID NOs: 61, 62, 63, 64, 65, 66, 67, 68, 69, 70, 71, 72, 73, 74, 75, and 76; and (f)

HVR-L3 comprising an amino acid sequence selected from the group consisting of SEQ ID NOs: 77, 78, 79, 80, 81, 82, 83, 84, 85, 86, 87, 88, 89, and 90.

In some embodiments, provided herein are anti-MS4A6A antibodies comprising (a) a $V_H$ domain comprising at least one, at least two, or all three $V_H$ HVR sequences selected from (i) HVR-H1 comprising an amino acid sequence selected from the group consisting of SEQ ID NO: 4, 5, 6, 7, 8, 9, 10, 11, 12, 13, 14, 15, and 16, (ii) HVR-H2 comprising an amino acid sequence selected from the group consisting of SEQ ID NO: 17, 18, 19, 20, 21, 22, 23, 24, 25, 26, 27, 28, 29, 30, and 31, and (iii) HVR-H3 comprising an amino acid sequence selected from the group consisting of SEQ ID NO: 32, 33, 34, 35, 36, 37, 38, 39, 40, 41, 42, 43, 44, and 45, and (b) a $V_L$ domain comprising at least one, at least two, or all three $V_L$ HVR sequences selected from (i) HVR-L1 comprising an amino acid sequence selected from the group consisting of SEQ ID NO: 46, 47, 48, 49, 50, 51, 52, 53, 54, 55, 56, 57, 58, 59, and 60, (ii) HVR-L2 comprising an amino acid sequence selected from the group consisting of SEQ ID NO: 61, 62, 63, 64, 65, 66, 67, 68, 69, 70, 71, 72, 73, 74, 75, and 76, and (iii) HVR-L3 comprising an amino acid sequence selected from the group consisting of SEQ ID NO: 77, 78, 79, 80, 81, 82, 83, 84, 85, 86, 87, 88, 89, and 90.

In some embodiments, provided herein are anti-MS4A6A antibodies comprising (a) a $V_H$ domain comprising (i) HVR-H1 comprising an amino acid sequence selected from the group consisting of SEQ ID NO: 4, 5, 6, 7, 8, 9, 10, 11, 12, 13, 14, 15, and 16, (ii) HVR-H2 comprising an amino acid sequence selected from the group consisting of SEQ ID NO: 17, 18, 19, 20, 21, 22, 23, 24, 25, 26, 27, 28, 29, 30, and 31, and (iii) HVR-H3 comprising an amino acid sequence selected from the group consisting of SEQ ID NO: 32, 33, 34, 35, 36, 37, 38, 39, 40, 41, 42, 43, 44, and 45, and (b) a $V_L$ domain comprising (i) HVR-L1 comprising an amino acid sequence selected from the group consisting of SEQ ID NO: 46, 47, 48, 49, 50, 51, 52, 53, 54, 55, 56, 57, 58, 59, and 60, (ii) HVR-L2 comprising an amino acid sequence selected from the group consisting of SEQ ID NO: 61, 62, 63, 64, 65, 66, 67, 68, 69, 70, 71, 72, 73, 74, 75, and 76, and (iii) HVR-L3 comprising an amino acid sequence selected from the group consisting of SEQ ID NO: 77, 78, 79, 80, 81, 82, 83, 84, 85, 86, 87, 88, 89, and 90.

In another aspect, an anti-MS4A6A antibody comprises a heavy chain variable domain ($V_H$) sequence having at least 90%, 91%, 92%, 93%, 94%, 95%, 96%, 97%, 98%, 99%, or 100% sequence identity to an amino acid sequence selected from the group consisting of SEQ ID NOs:91, 92, 93, 94, 95, 96, 97, 98, 99, 100, 101, 102, 103, 104, 105, 106, 107, and 108. In certain embodiments, a $V_H$ sequence having at least 90%, 91%, 92%, 93%, 94%, 95%, 96%, 97%, 98%, or 99% identity to an amino acid sequence selected from the group consisting of SEQ ID NOs: 91, 92, 93, 94, 95, 96, 97, 98, 99, 100, 101, 102, 103, 104, 105, 106, 107, and 108 contains substitutions (e.g., conservative substitutions), insertions, or deletions relative to the reference sequence, but an anti-MS4A6A antibody comprising that sequence retains the ability to bind to MS4A6A. In certain embodiments, a total of 1 to 10 amino acids have been substituted, inserted, and/or deleted in SEQ ID NO: 91, 92, 93, 94, 95, 96, 97, 98, 99, 100, 101, 102, 103, 104, 105, 106, 107, and 108. In certain embodiments, a total of 1 to 5 amino acids have been substituted, inserted and/or deleted in SEQ ID NO: 91, 92, 93, 94, 95, 96, 97, 98, 99, 100, 101, 102, 103, 104, 105, 106, 107, and 108. In certain embodiments, substitutions, insertions, or deletions occur in regions outside the HVRs (i.e., in the FRs). Optionally, the anti-MS4A6A antibody comprises the $V_H$ sequence of SEQ ID NO: 91, 92, 93, 94, 95, 96, 97, 98, 99, 100, 101, 102, 103, 104, 105, 106, 107, and 108, including post-translational modifications of that sequence. In a particular embodiment, the $V_H$ comprises one, two or three HVRs selected from: (a) HVR-H1 comprising an amino acid sequence selected from the group consisting of SEQ ID NOs: 4, 5, 6, 7, 8, 9, 10, 11, 12, 13, 14, 15, and 16, (b) HVR-H2 comprising an amino acid sequence selected from the group consisting of SEQ ID NOs: 17, 18, 19, 20, 21, 22, 23, 24, 25, 26, 27, 28, 29, 30, and 31, and (c) HVR-H3 comprising an amino acid sequence selected from the group consisting of SEQ ID NOs: 32, 33, 34, 35, 36, 37, 38, 39, 40, 41, 42, 43, 44, and 45.

In another aspect, an anti-MS4A6A antibody is provided, wherein the antibody comprises a light chain variable domain ($V_L$) having at least 90%, 91%, 92%, 93%, 94%, 95%, 96%, 97%, 98%, 99%, or 100% sequence identity to an amino acid sequence selected from the group consisting of SEQ ID NOs:109, 110, 111, 112, 113, 114, 115, 116, 117, 118, 119, 120, 121, 122, 123, 124, 125, and 126. In certain embodiments, a $V_L$ sequence having at least 90%, 91%, 92%, 93%, 94%, 95%, 96%, 97%, 98%, or 99% identity to an amino acid sequence selected from the group consisting of SEQ ID NOs: 109, 110, 111, 112, 113, 114, 115, 116, 117, 118, 119, 120, 121, 122, 123, 124, 125, and 126, and contains substitutions (e.g., conservative substitutions), insertions, or deletions relative to the reference sequence, but an anti-MS4A6A antibody comprising that sequence retains the ability to bind to MS4A6A. In some embodiments, a total of 1 to 10 amino acids have been substituted, inserted and/or deleted in SEQ ID NO: 109, 110, 111, 112, 113, 114, 115, 116, 117, 118, 119, 120, 121, 122, 123, 124, 125, and 126. In certain embodiments, a total of 1 to 5 amino acids have been substituted, inserted and/or deleted in SEQ ID NO: 109, 110, 111, 112, 113, 114, 115, 116, 117, 118, 119, 120, 121, 122, 123, 124, 125, and 126. In certain embodiments, the substitutions, insertions, or deletions occur in regions outside the HVRs (i.e., in the FRs). Optionally, the anti-MS4A6A antibody comprises the $V_L$ sequence of SEQ ID NO: 109, 110, 111, 112, 113, 114, 115, 116, 117, 118, 119, 120, 121, 122, 123, 124, 125, and 126, including post-translational modifications of that sequence. In a particular embodiment, the $V_L$ comprises one, two or three HVRs selected from (a) HVR-L1 comprising an amino acid sequence selected from the group consisting of SEQ ID NOs: 46, 47, 48, 49, 50, 51, 52, 53, 54, 55, 56, 57, 58, 59, and 60, (b) HVR-L2 comprising an amino acid sequence selected from the group consisting of SEQ ID NOs: 61, 62, 63, 64, 65, 66, 67, 68, 69, 70, 71, 72, 73, 74, 75, and 76, and (c) HVR-L3 comprising an amino acid sequence selected from the group consisting of SEQ ID NOs: 77, 78, 79, 80, 81, 82, 83, 84, 85, 86, 87, 88, 89, and 90.

In some embodiments, an anti-MS4A6A antibody is provided, wherein the antibody comprises a $V_H$ as in any of the embodiments provided above, and a $V_L$ as in any of the embodiments provided above. In some embodiments, provided herein are anti-MS4A6A antibodies, wherein the antibody comprises a $V_H$ as in any of the embodiments provided above, and a $V_L$ as in any of the embodiments provided above. In one embodiment, the antibody comprises the $V_H$ and $V_L$ sequences in SEQ ID NOs:91-108 and SEQ ID NOs:109-126, respectively, including post-translational modifications of those sequences.

In some embodiments, provided herein are anti-MS4A6A antibodies comprising a heavy chain variable domain ($V_H$) and a light chain variable domain ($V_L$), wherein the $V_H$ and $V_L$ are selected from the group consisting of: $V_H$ comprising the amino acid sequence of SEQ ID NO:91 and $V_L$ comprising the amino acid sequence of SEQ ID NO:109; $V_H$ comprising the amino acid sequence of SEQ ID NO:92 and $V_L$ comprising the amino acid sequence of SEQ ID NO:110; $V_H$ comprising the amino acid sequence of SEQ ID NO:93 and $V_L$ comprising the amino acid sequence of SEQ ID NO:111; $V_H$ comprising the amino acid sequence of SEQ ID NO:94 and V$_L$ comprising the amino acid sequence of SEQ ID NO:112; V$_H$ comprising the amino acid sequence of SEQ ID NO:95 and V$_L$ comprising the amino acid sequence of SEQ ID NO:113; V$_H$ comprising the amino acid sequence of SEQ ID NO:96 and V$_L$ comprising the amino acid sequence of SEQ ID NO:114; V$_H$ comprising the amino acid sequence of SEQ ID NO:97 and V$_L$ comprising the amino acid sequence of SEQ ID NO:115; V$_H$ comprising the amino acid sequence of SEQ ID NO:98 and V$_L$ comprising the amino acid sequence of SEQ ID NO:116; V$_H$ comprising the amino acid sequence of SEQ ID NO:99 and V$_L$ comprising the amino acid sequence of SEQ ID NO:117; V$_H$ comprising the amino acid sequence of SEQ ID NO:100 and V$_L$ comprising the amino acid sequence of SEQ ID NO:118; V$_H$ comprising the amino acid sequence of SEQ ID NO:101 and V$_L$ comprising the amino acid sequence of SEQ ID NO:109; V$_H$ comprising the amino acid sequence of SEQ ID NO:102 and V$_L$ comprising the amino acid sequence of SEQ ID NO:119; V$_H$ comprising the amino acid sequence of SEQ ID NO:103 and V$_L$ comprising the amino acid sequence of SEQ ID NO:120; V$_H$ comprising the amino acid sequence of SEQ ID NO:104 and V$_L$ comprising the amino acid sequence of SEQ ID NO:121; V$_H$ comprising the amino acid sequence of SEQ ID NO:105 and V$_L$ comprising the amino acid sequence of SEQ ID NO:116; V$_H$ comprising the amino acid sequence of SEQ ID NO:106 and V$_L$ comprising the amino acid sequence of SEQ ID NO:122; V$_H$ comprising the amino acid sequence of SEQ ID NO:93 and V$_L$ comprising the amino acid sequence of SEQ ID NO:123; V$_H$ comprising the amino acid sequence of SEQ ID NO:93 and V$_L$ comprising the amino acid sequence of SEQ ID NO:124; V$_H$ comprising the amino acid sequence of SEQ ID NO:107 and V$_L$ comprising the amino acid sequence of SEQ ID NO:125; and V$_H$ comprising the amino acid sequence of SEQ ID NO:108 and V$_L$ comprising the amino acid sequence of SEQ ID NO:126.

In some embodiments, an anti-MS4A6A antibody of the present disclosure competitively inhibits binding of at least one reference antibody selected from 6A-1, 6A-2, 6A-3, 6A-4, 6A-5, 6A-6, 6A-7, 6A-8, 6A-9, 6A-10, 6A-11, 6A-12, 6A-13, 6A-14, 6A-15, 6A-16, 6A-17, 6A-18, 6A-20, 6A-21, 6A-22, 6A-23.

In some embodiments, an anti-MS4A6A antibody of the present disclosure competes with one or more reference antibodies selected from 6A-1, 6A-2, 6A-3, 6A-4, 6A-5, 6A-6, 6A-7, 6A-8, 6A-9, 6A-10, 6A-11, 6A-12, 6A-13, 6A-14, 6A-15, 6A-16, 6A-17, 6A-18, 6A-20, 6A-21, 6A-22, and 6A-23, and any combination thereof, for binding to MS4A6A when the anti-MS4A6A antibody reduces the binding of one or more reference antibodies selected from 6A-1, 6A-2, 6A-3, 6A-4, 6A-5, 6A-6, 6A-7, 6A-8, 6A-9, 6A-10, 6A-11, 6A-12, 6A-13, 6A-14, 6A-15, 6A-16, 6A-17, 6A-18, 6A-20, 6A-21, 6A-22, and 6A-23, and any combination thereof to MS4A6A by an amount the ranges from about 50% to 100%, as compared to binding to MS4A6A in the absence of the anti-MS4A6A antibody.

In some embodiments, an anti-MS4A6A antibody of the present disclosure competes with one or more reference antibodies selected from 6A-1, 6A-2, 6A-3, 6A-4, 6A-5, 6A-6, 6A-7, 6A-8, 6A-9, 6A-10, 6A-11, 6A-12, 6A-13, 6A-14, 6A-15, 6A-16, 6A-17, 6A-18, 6A-20, 6A-21, 6A-22, and 6A-23, and any combination thereof for binding to MS4A6A when the anti-MS4A6A antibody reduces the binding of one or more reference antibodies selected from 6A-1, 6A-2, 6A-3, 6A-4, 6A-5, 6A-6, 6A-7, 6A-8, 6A-9, 6A-10, 6A-11, 6A-12, 6A-13, 6A-14, 6A-15, 6A-16, 6A-17, 6A-18, 6A-20, 6A-21, 6A-22, and 6A-23, and any combination thereof to MS4A6A by at least 50%, at least 55%, by at least 60%, at least 65%, at least 70%, at least 75%, at least 80%, at least 85%, at least 90%, at least 95%, or 100%, as compared to binding to MS4A6A in the absence of the anti-MS4A6A antibody. In some embodiments, an anti-MS4A6A antibody of the present disclosure that reduces the binding of one or more reference antibodies selected from 6A-1, 6A-2, 6A-3, 6A-4, 6A-5, 6A-6, 6A-7, 6A-8, 6A-9, 6A-10, 6A-11, 6A-12, 6A-13, 6A-14, 6A-15, 6A-16, 6A-17, 6A-18, 6A-20, 6A-21, 6A-22, and 6A-23, and any combination thereof to MS4A6A by 100% indicates that the anti-MS4A6A antibody essentially completely blocks the binding of one or more reference antibodies selected from 6A-1, 6A-2, 6A-3, 6A-4, 6A-5, 6A-6, 6A-7, 6A-8, 6A-9, 6A-10, 6A-11, 6A-12, 6A-13, 6A-14, 6A-15, 6A-16, 6A-17, 6A-18, 6A-20, 6A-21, 6A-22, and 6A-23, and any combination thereof to MS4A6A. In some embodiments, the anti-MS4A6A antibody and the one or more antibodies selected from 6A-1, 6A-2, 6A-3, 6A-4, 6A-5, 6A-6, 6A-7, 6A-8, 6A-9, 6A-10, 6A-11, 6A-12, 6A-13, 6A-14, 6A-15, 6A-16, 6A-17, 6A-18, 6A-20, 6A-21, 6A-22, and 6A-23, and any combination thereof are present in an amount that corresponds to a 10:1 ratio, 9:1 ratio, 8:1 ratio, 7:1 ratio, 6:1 ratio, 5:1 ratio, 4:1 ratio, 3:1 ratio, 2:1 ratio, 1:1 ratio, 0.75:1 ratio, 0.5:1 ratio, 0.25:1 ratio, 0.1:1 ratio, 0.075:1 ratio, 0.050:1 ratio, 0.025:1 ratio, 0.01:1 ratio, 0.0075: ratio, 0.0050:1 ratio, 0.0025:1 ratio, 0.001: ratio, 0.00075:1 ratio, 0.00050:1 ratio, 0.00025:1 ratio, 0.0001: ratio, 1:10 ratio, 1:9 ratio, 1:8 ratio, 1:7 ratio, 1:6 ratio, 1:5 ratio, 1:4 ratio, 1:3 ratio, 1:2 ratio, 1:0.75 ratio, 1:0.5 ratio, 1:0.25 ratio, 1:0.1 ratio, 1:0.075 ratio, 1:0.050 ratio, 1:0.025 ratio, 1:0.01 ratio, 1:0.0075 ratio, 1:0.0050 ratio, 1:0.0025 ratio, 1:0.001 ratio, 1:0.00075 ratio, 1:0.00050 ratio, 1:0.00025 ratio, or 1:0.0001ratio of anti-MS4A6A antibody to one or more reference antibodies selected from 6A-1, 6A-2, 6A-3, 6A-4, 6A-5, 6A-6, 6A-7, 6A-8, 6A-9, 6A-10, 6A-11, 6A-12, 6A-13, 6A-14, 6A-15, 6A-16, 6A-17, 6A-18, 6A-20, 6A-21, 6A-22, and 6A-23, and any combination thereof. In some embodiments, the anti-MS4A6A antibody is present in excess by an amount that ranges from about 1.5-fold to 100-fold, or greater than 100-fold compared to the amount of the one or more antibodies selected from 6A-1, 6A-2, 6A-3, 6A-4, 6A-5, 6A-6, 6A-7, 6A-8, 6A-9, 6A-10, 6A-11, 6A-12, 6A-13, 6A-14, 6A-15, 6A-16, 6A-17, 6A-18, 6A-20, 6A-21, 6A-22, and 6A-23, and any combination thereof. In some embodiments, the anti-MS4A6A antibody is present in an amount that is about a 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, or 100-fold excess compared to the amount of the one or more reference antibodies selected from 6A-1, 6A-2, 6A-3, 6A-4, 6A-5, 6A-6, 6A-7, 6A-8, 6A-9, 6A-10, 6A-11, 6A-12, 6A-13, 6A-14, 6A-15, 6A-16, 6A-17, 6A-18, 6A-20, 6A-21, 6A-22, and 6A-23, and any combination thereof.

In some embodiments, an anti-MS4A6A antibody of the present disclosure binds to an epitope of human MS4A6A that is the same as or overlaps with the MS4A6A epitope bound by at least one reference antibody selected from 6A-1, 6A-2, 6A-3, 6A-4, 6A-5, 6A-6, 6A-7, 6A-8, 6A-9, 6A-10, 6A-11, 6A-12, 6A-13, 6A-14, 6A-15, 6A-16, 6A-17, 6A-18, 6A-20, 6A-21, 6A-22, and 6A-23

In some embodiments, an anti-MS4A6A antibody of the present disclosure binds essentially the same MS4A6A epitope bound by at least one reference antibody selected from 6A-1, 6A-2, 6A-3, 6A-4, 6A-5, 6A-6, 6A-7, 6A-8, 6A-9, 6A-10, 6A-11, 6A-12, 6A-13, 6A-14, 6A-15, 6A-16, 6A-17, 6A-18, 6A-20, 6A-21, 6A-22, and 6A-23. Detailed exemplary methods for mapping an epitope to which an antibody binds are provided in Morris (1996) "Epitope Mapping Protocols," in *Methods in Molecular Biology* vol. 66 (Humana Press, Totowa, NJ).

In some embodiments, an anti-MS4A6A antibody of the present disclosure competes with one or more reference antibodies selected from 6A-2, 6A-3, 6A-6, 6A-8, 6A-9, 6A-10, 6A-11, 6A-12, 6A-13, 6A-14, 6A-15, 6A-16, 6A-18, 6A-19, 6A-21, 6A-22, and 6A-23, and any combination thereof, for binding to MS4A6A. In some embodiments, an anti-MS4A6A antibody of the present disclosure competes with one or more reference antibodies selected from 6A-1, 6A-4, 6A-5, 6A-7, 6A-17, and 6A-20, and any combination thereof for binding to MS4A6A.

In some embodiments, an anti-MS4A6A antibody of the present disclosure competitively inhibits binding of at least one reference antibody selected from 6A-2, 6A-3, 6A-6, 6A-8, 6A-9, 6A-10, 6A-11, 6A-12, 6A-13, 6A-14, 6A-15, 6A-16, 6A-18, 6A-19, 6A-21, 6A-22, and 6A-23, and any combination thereof, for binding to MS4A6A. In some embodiments, an anti-MS4A6A antibody of the present disclosure competitively inhibits binding of at least one reference antibody selected from 6A-1, 6A-4, 6A-5, 6A-7, 6A-17, and 6A-20, and any combination thereof, for binding to MS4A6A.

In some embodiments, an anti-MS4A6A antibody of the present disclosure has the same or overlapping epitope on MS4A6A as at least one reference antibody selected from 6A-2, 6A-3, 6A-6, 6A-8, 6A-9, 6A-10, 6A-11, 6A-12, 6A-13, 6A-14, 6A-15, 6A-16, 6A-18, 6A-19, 6A-21, 6A-22, and 6A-23, and any combination thereof, for binding to MS4A6A. In some embodiments, an anti-MS4A6A antibody of the present disclosure has the same or overlapping epitope on MS4A6A as at least one reference antibody selected from 6A-1, 6A-4, 6A-5, 6A-7, 6A-17, and 6A-20, and any combination thereof, for binding to MS4A6A.

In some embodiments, an anti-MS4A6A antibody of the present disclosure binds to one or more amino acids within amino acid residues 1-46 of human MS4A6A (SEQ ID NO:1). In some embodiments, an anti-MS4A6A antibody of the present disclosure binds to one or more amino acids within amino acid residues 47-67 of human MS4A6A (SEQ ID NO:1). In some embodiments, an anti-MS4A6A antibody of the present disclosure bind to one or more amino acids within amino acid residues 68-84 of human MS4A6A (SEQ ID NO:1). In some embodiments, an anti-MS4A6A antibody of the present disclosure binds to one or more amino acids within amino acid residues 85-105 of human MS4A6A. In some embodiments, an anti-MS4A6A of the present disclosure binds to one or more amino acids within amino acid residues 106-116 of human MS4A6A. In some embodiments, an anti-MS4A6A of the present disclosure binds to one or more amino acids within amino acid residues 117-137 of human MS4A6A. In some embodiments, an anti-MS4A6A of the present disclosure binds to one or more amino acids within amino acid residues 138-185 of human MS4A6A. In some embodiments, an anti-MS4A6A of the present disclosure binds to one or more amino acids within amino acid residues 186-206 of human MS4A6A. In some embodiments, an anti-MS4A6A of the present disclosure binds to one or more amino acids within amino acid residues 207-248 of human MS4A6A. In some embodiments, an anti-MS4A6A antibody of the present disclosure binds to extracellular domain 1 (ECL1) of MS4A6A. In some embodiments, an anti-MS4A6A antibody of the present disclosure binds to extracellular domain 2 (ECL2) of MS4A6A. In some embodiments, an anti-MS4A6A antibody of the present disclosure binds to one or more amino acids within amino acid residues 180-190 of human MS4A6A. In some embodiments, an anti-MS4A6A antibody of the present disclosure binds to one or more amino acids within amino acid residues 181-189 of human MS4A6A, within amino acid residues 182-188 of human MS4A6A, within amino acid residues 183-187 of human MS4A6A, or within amino acid residues 184-186 of human MS4A6A. In some embodiments, an anti-MS4A6A antibody of the present disclosure binds to amino acid residue 185 of human MS4A6A. In some embodiments, an anti-MS4A6A antibody of the present disclosure binds to amino acid residue 185 of human MS4A6A, wherein amino acid residue 185 of human MS4A6A is threonine. In some embodiments, an anti-MS4A6A antibody of the present disclosure binds to amino acid residue 185 of human MS4A6A, wherein amino acid residue 185 of human MS4A6A is serine. In some embodiments, an anti-MS4A6A antibody of the present disclosure binds to amino acid residue 185 of MS4A6A, wherein amino acid residue 185 of MS4A6A is proline.

Any suitable competition assay or MS4A6A binding assay known in the art, such as BIAcore analysis, ELISA assays, or flow cytometry, may be utilized to determine whether an anti-MS4A6A antibody competes with (or competitively inhibits the binding of) one or more reference antibodies selected from 6A-1, 6A-2, 6A-3, 6A-4, 6A-5, 6A-6, 6A-7, 6A-8, 6A-9, 6A-10, 6A-11, 6A-12, 6A-13, 6A-14, 6A-15, 6A-16, 6A-17, 6A-18, 6A-20, 6A-21, 6A-22, and 6A-23, and any combination thereof for binding to MS4A6A. In an exemplary competition assay, immobilized MS4A6A or cells expressing MS4A6A on the cell surface are incubated in a solution comprising a first labeled antibody that binds to MS4A6A (e.g., human or non-human primate) and a second unlabeled antibody that is being tested for its ability to compete with the first antibody for binding to MS4A6A. The second antibody may be present in a hybridoma supernatant. As a control, immobilized MS4A6A or cells expressing MS4A6A is incubated in a solution comprising the first labeled antibody but not the second unlabeled antibody. After incubation under conditions permissive for binding of the first antibody to MS4A6A, excess unbound antibody is removed, and the amount of label associated with immobilized MS4A6A or cells expressing MS4A6A is measured. If the amount of label associated with immobilized MS4A6A or cells expressing MS4A6A is substantially reduced in the test sample relative to the control sample, then that indicates that the second antibody is competing with the first antibody for binding to MS4A6A. See, Harlow and Lane (1988) *Antibodies: A Laboratory Manual* ch. 14 (Cold Spring Harbor Laboratory, Cold Spring Harbor, NY).

Further provided herein are anti-MS4A6A antibodies which competitively inhibit binding of and/or competes for binding with an anti-MS4A6A antibody comprising (a) a $V_H$ domain comprising at least one, at least two, or all three $V_H$HVR sequences selected from (i) HVR-H1 comprising an amino acid sequence selected from the group consisting of SEQ ID NO: 4, 5, 6, 7, 8, 9, 10, 11, 12, 13, 14, 15, and 16, (ii) HVR-H2 comprising an amino acid sequence selected from the group consisting of SEQ ID NO: 17, 18, 19, 20, 21, 22, 23, 24, 25, 26, 27, 28, 29, 30, and 31, and (iii) HVR-H3 comprising an amino acid sequence selected from the group consisting of SEQ ID NO: 32, 33, 34, 35, 36, 37, 38, 39, 40, 41, 42, 43, 44, and 45, and (b) a $V_L$ domain comprising at least one, at least two, or all three $V_L$HVR sequences selected from (i) HVR-L1 comprising an amino acid sequence selected from the group consisting of SEQ ID NO: 46, 47, 48, 49, 50, 51, 52, 53, 54, 55, 56, 57, 58, 59, and 60, (ii) HVR-L2 comprising an amino acid sequence selected from the group consisting of SEQ ID NO: 61, 62, 63, 64, 65, 66, 67, 68, 69, 70, 71, 72, 73, 74, 75, and 76, and (iii) HVR-L3 comprising an amino acid sequence selected from the group consisting of SEQ ID NO: 77, 78, 79, 80, 81, 82, 83, 84, 85, 86, 87, 88, 89, and 90. In some embodiments, the antibody comprises the $V_H$ and $V_L$ sequences in SEQ ID NOs:91-108 and SEQ ID NOs:109-126, respectively.

Provided herein are anti-MS4A6A antibodies which bind to an epitope of human MS4A6A that is the same as or overlaps with the epitope bound by an anti-MS4A6A antibody comprising (a) a $V_H$ domain comprising at least one, at least two, or all three $V_H$ HVR sequences selected from (i) HVR-H1 comprising an amino acid sequence selected from the group consisting of SEQ ID NO: 4, 5, 6, 7, 8, 9, 10, 11, 12, 13, 14, 15, and 16, (ii) HVR-H2 comprising an amino acid sequence selected from the group consisting of SEQ ID NO: 17, 18, 19, 20, 21, 22, 23, 24, 25, 26, 27, 28, 29, 30, and 31, and (iii) HVR-H3 comprising an amino acid sequence selected from the group consisting of SEQ ID NO: 32, 33, 34, 35, 36, 37, 38, 39, 40, 41, 42, 43, 44, and 45, and (b) a $V_L$ domain comprising at least one, at least two, or all three $V_L$ HVR sequences selected from (i) HVR-L1 comprising an amino acid sequence selected from the group consisting of SEQ ID NO: 46, 47, 48, 49, 50, 51, 52, 53, 54, 55, 56, 57, 58, 59, and 60, (ii) HVR-L2 comprising an amino acid sequence selected from the group consisting of SEQ ID NO: 61, 62, 63, 64, 65, 66, 67, 68, 69, 70, 71, 72, 73, 74, 75, and 76, and (iii) HVR-L3 comprising an amino acid sequence selected from the group consisting of SEQ ID NO: 77, 78, 79, 80, 81, 82, 83, 84, 85, 86, 87, 88, 89, and 90. In some embodiments, the antibody comprises the $V_H$ and $V_L$ sequences in SEQ ID NOs:91-108 and SEQ ID NOs:109-126, respectively. In some embodiments, the epitope of human MS4A6A is the same epitope as bound by an anti-MS4A6A antibody.

In some embodiments, the anti-MS4A6A antibody according to any of the above embodiments is a monoclonal antibody, including a humanized and/or human antibody. In some embodiments, the anti-MS4A6A antibody is an antibody fragment, e.g., a Fv, Fab, Fab', scFv, diabody, or F(ab')2 fragment. In some embodiments, the anti-MS4A6A antibody is a substantially full-length antibody, e.g., an IgG1 antibody, IgG2a antibody or other antibody class or isotype as defined herein.

In some embodiments, an anti-MS4A6A antibody according to any of the above embodiments may incorporate any of the features, singly or in combination, as described in Sections 1-7 below:

(1) Anti-MS4A6A Antibody Binding Affinity

In some embodiments of any of the antibodies provided herein, the antibody has a dissociation constant (Kd) of <1 µM, <100 nM, <10 nM, <1 nM, <0.1 nM, <0.01 nM, or <0.001 nM (e.g., $10^{-8}$ M or less, e.g., from $10^{-8}$ M to $10^{-13}$ M, e.g., from $10^{-9}$ M to $10^{-13}$ M). Dissociation constants may be determined through any analytical technique, including any biochemical or biophysical technique such as ELISA, surface plasmon resonance (SPR), bio-layer interferometry (see, e.g., Octet System by ForteBio), isothermal titration calorimetry (ITC), differential scanning calorimetry (DSC), circular dichroism (CD), stopped-flow analysis, and colorimetric or fluorescent protein melting analyses. In one embodiment, Kd is measured by a radiolabeled antigen binding assay (RIA). In some embodiment, an RIA is performed with the Fab version of an antibody of interest and its antigen, for example as described in Chen et al. *J. Mol. Biol.* 293:865-881(1999)). In some embodiments, Kd is measured using a BIACORE surface plasmon resonance assay, for example, an assay using a BIACORE-2000 or a BIACORE-3000 (BIAcore, Inc., Piscataway, NJ) is performed at 25° C. with immobilized antigen CMS chips at ~10 response units (RU). In some embodiments, the KD is determined using a monovalent antibody (e.g., a Fab) or a full-length antibody. In some embodiments, the KD is determined using a full-length antibody in a monovalent form.

(2) Antibody Fragments

In some embodiments of any of the antibodies provided herein, the antibody antibodies is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP404097; WO 1993/01161; Hudson et al. *Nat. Med.* 9:129-134 (2003). Triabodies and tetrabodies are also described in Hudson et al. Nat. Med. 9:129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (see, e.g., U.S. Pat. No. 6,248,516).

Antibody fragments can be made by various techniques, including but not limited to proteolytic digestion of an intact antibody as well as production by recombinant host cells (e.g., *E. coli* or phage), as described herein.

(3) Chimeric and Humanized Antibodies

In some embodiments of any of the antibodies provided herein, the antibody is a chimeric antibody. Certain chimeric antibodies are described, e.g., in U.S. Pat. No. 4,816,567. In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In some embodiments of any of the antibodies provided herein, the antibody is a humanized antibody. Typically, a non-human antibody is humanized to reduce immunogenicity to humans, while retaining the specificity and affinity of the parental non-human antibody. In certain embodiments, a humanized antibody is substantially non-immunogenic in humans. In certain embodiments, a humanized antibody has substantially the same affinity for a target as an antibody from another species from which the humanized antibody is derived. See, e.g., U.S. Pat. Nos. 5,530,101, 5,693,761; 5,693,762; and 5,585,089. In certain embodiments, amino acids of an antibody variable domain that can be modified without diminishing the native affinity of the antigen binding domain while reducing its immunogenicity are identified. See, e.g., U.S. Pat. Nos. 5,766,886 and 5,869,619. Generally, a humanized antibody comprises one or more variable domains in which HVRs (or portions thereof) are derived from a non-human antibody, and FRs (or portions thereof)

are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), for example, to restore or improve antibody specificity or affinity.

Humanized antibodies and methods of making them are reviewed, for example, in Almagro et al. *Front. Biosci.* 13:161 9-1633 (2008), and are further described, e.g., in U.S. Pat. Nos. 5,821,337, 7,527,791, 6,982,321, and 7,087, 409. Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA* 89:4285 (1992); and Presta et al., *J. Immunol.* 151:2623 (1993)); human mature (somatically mutated) framework regions or human germline framework regions (see, e.g., Almagro and Fransson *Front. Biosci.* 13:1619-1633 (2008)); and framework regions derived from screening FR libraries (see, e.g., Baca et al. *J. Biol. Chem.* 272:10678-10684 (1997) and Rosok et al. *J. Biol. Chem.* 271:22611-22618 (1996)).

(4) Human Antibodies

In some embodiments of any of the antibodies provided herein, the antibody is a human antibody. Human antibodies can be produced using various techniques known in the art. Human antibodies are described generally in van Dijk et al. *Curr. Opin. Pharmacol.* 5:368-74 (2001) and Lonberg *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. One can engineer mouse strains deficient in mouse antibody production with large fragments of the human Ig loci in anticipation that such mice would produce human antibodies in the absence of mouse antibodies. Large human Ig fragments can preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains can yield high affinity fully human antibodies against any antigen of interest, including human antigens. Using the hybridoma technology, antigen-specific human MAbs with the desired specificity can be produced and selected. Certain exemplary methods are described in U.S. Pat. No. 5,545,807, EP 546073, and EP 546073. See also, for example, U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology. Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. *Immunol.* 133:3001 (1984) and Boerner et al. *J. Immunol.* 147:86 (1991)). Human antibodies generated via human B-cell hybridoma technology are also described in Li et al. *Proc. Natl. Acad. Sci. USA,* 1 03:3557-3562 (2006). Additional methods include those described, for example, in U.S. Pat. No. 7,189,826 (describing production of monoclonal human IgM antibodies from hybridoma cell lines). Human hybridoma technology (Trioma technology) is also described in Vollmers et al. *Histology and Histopathology* 20(3):927-937 (2005) and Vollmers et al. *Methods and Findings in Experimental and Clinical Pharmacology* 27(3): 185-91 (2005). Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

In some embodiments of any of the antibodies provided herein, the antibody is a human antibody isolated by in vitro methods and/or screening combinatorial libraries for antibodies with the desired activity or activities. Suitable examples include but are not limited to phage display (CAT, Morphosys, Dyax, Biosite/Medarex, Xoma, Symphogen, Alexion (formerly Proliferon), Affimed) ribosome display (CAT), yeast display (Adimab), and the like. In certain phage display methods, repertoires of VH and VL genes are separately cloned by polymerase chain reaction (PCR) and recombined randomly in phage libraries, which can then be screened for antigen-binding phage as described in Winter et al. *Ann. Rev. Immunol.* 12: 433-455 (1994). For example, a variety of methods are known in the art for generating phage display libraries and screening such libraries for antibodies possessing the desired binding characteristics. See also Sidhu et al. *J. Mol. Biol.* 338(2): 299-310, 2004; Lee et al. *J. Mol. Biol.* 340(5): 1073-1093, 2004; Fellouse *Proc. Natl. Acad. Sci. USA* 101(34):12467-12472 (2004); and Lee et al. *J. Immunol. Methods* 284(-2):1 19-132 (2004). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al. EMBO J. 12: 725-734 (1993). Finally, naive libraries can also be made synthetically by cloning unrearranged V-gene segments from stem cells, and using PCR primers comprising random sequence to encode the highly variable HVR3 regions and to accomplish rearrangement in vitro, as described by Hoogenboom et al. *J. Mol. Biol.,* 227: 381-388, 1992. Patent publications describing human antibody phage libraries include, for example: U.S. Pat. No. 5,750,373, and US Pat. Publication Nos. 2007/0292936 and 2009/0002360. Antibodies isolated from human antibody libraries are considered human antibodies or human antibody fragments herein.

(5) Constant Regions Including Fc Regions

In some embodiments of any of the antibodies provided herein, the antibody comprises an Fc. In some embodiments, the Fc is a human IgG1, IgG2, IgG3, and/or IgG4 isotype. In some embodiments, the antibody is of the IgG class, the IgM class, or the IgA class.

In certain embodiments of any of the antibodies provided herein, the antibody has an IgG2 isotype. In some embodiments, the antibody contains a human IgG2 constant region. In some embodiments, the human IgG2 constant region includes an Fc region. In some embodiments, the antibody induces the one or more MS4A6A activities or independently of binding to an Fc receptor. In some embodiments, the antibody binds an inhibitory Fc receptor. In certain embodiments, the inhibitory Fc receptor is inhibitory Fc-gamma receptor IIB (FcγIIB).

In certain embodiments of any of the antibodies provided herein, the antibody has an IgG1 isotype. In some embodiments, the antibody contains a mouse IgG1 constant region. In some embodiments, the antibody contains a human IgG1 constant region. In some embodiments, the human IgG1 constant region includes an Fc region. In some embodiments, the antibody binds an inhibitory Fc receptor. In certain embodiments, the inhibitory Fc receptor is inhibitory Fc-gamma receptor IIB (FcγIIB).

In certain embodiments of any of the antibodies provided herein, the antibody has an IgG4 isotype. In some embodiments, the antibody contains a human IgG4 constant region. In some embodiments, the human IgG4 constant region includes an Fc region. In some embodiments, the antibody binds an inhibitory Fc receptor. In certain embodiments, the inhibitory Fc receptor is inhibitory Fc-gamma receptor IIB (FcγIIB).

In certain embodiments of any of the antibodies provided herein, the antibody has a hybrid IgG2/4 isotype. In some embodiments, the antibody includes an amino acid sequence comprising amino acids 118 to 260 according to EU numbering of human IgG2 and amino acids 261-447 according to EU numbering of human IgG4 (WO 1997/11971; WO 2007/106585).

In some embodiments, the Fc region increases clustering without activating complement as compared to a corresponding antibody comprising an Fc region that does not comprise the amino acid substitutions. In some embodiments, the antibody induces one or more activities of a target specifically bound by the antibody. In some embodiments, the antibody binds to MS4A6A.

It may also be desirable to modify an anti-MS4A6A antibody of the present disclosure to modify effector function and/or to increase serum half-life of the antibody. For example, the Fc receptor binding site on the constant region may be modified or mutated to remove or reduce binding affinity to certain Fc receptors, such as Fc=RI, FcγRII, and/or FcγRIII to reduce Antibody-dependent cell-mediated cytotoxicity. In some embodiments, the effector function is impaired by removing N-glycosylation of the Fc region (e.g., in the CH2 domain of IgG) of the antibody. In some embodiments, the effector function is impaired by modifying regions such as 233-236, 297, and/or 327-331 of human IgG as described in WO 99/58572 and Armour et al. *Molecular Immunology* 40: 585-593 (2003); Reddy et al. *J. Immunology* 164:1925-1933 (2000). In other embodiments, it may also be desirable to modify an anti-MS4A6A antibody of the present disclosure to modify effector function to increase finding selectivity toward the ITIM-containing FcgRIIb (CD32b) to increase clustering of MS4A6A antibodies on adjacent cells without activating humoral responses including Antibody-dependent cell-mediated cytotoxicity and antibody-dependent cellular phagocytosis.

To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule. Other amino acid sequence modifications.

(6) Multispecific Antibodies

Multispecific are antibodies that have binding specificities for at least two different epitopes, including those on the same or another polypeptide (e.g., one or more MS4A6A polypeptides of the present disclosure). In some embodiments, the multispecific antibody can be a bispecific antibody. In some embodiments, the multispecific antibody can be a trispecific antibody. In some embodiments, the multispecific antibody can be a tetraspecific antibody. Such antibodies can be derived from full-length antibodies or antibody fragments (e.g., F(ab')$_2$bispecific antibodies). In some embodiments, the multispecific antibody comprises a first antigen binding region which binds to first site on MS4A6A and comprises a second antigen binding region which binds to a second site on MS4A6A. In some embodiment, the multispecific antibodies comprises a first antigen binding region which binds to MS4A6A and a second antigen binding region that binds to a second polypeptide.

Provided herein are multispecific antibodies comprises a first antigen binding region, wherein the first antigen binding region comprises the six HVRs of an antibody described herein, which binds to MS4A6A and a second antigen binding region that binds to a second polypeptide. In some embodiments, the first antigen binding region comprises the $V_H$ or $V_L$ of an antibody described herein.

In some embodiments of any of the multispecific antibodies, the second polypeptide is a) an antigen facilitating transport across the blood-brain-barrier; (b) an antigen facilitating transport across the blood-brain-barrier selected from transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopep peptide, and ANG1005; (c) a disease-causing protein selected from amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides; (d) ligands and/or proteins expressed on immune cells, wherein the ligands and/or proteins selected from CD40, OX40, ICOS, CD28, CD137/4-1BB, CD27, GITR, PD-L1, CTLA-4, PD-L2, PD-1, B7-H3, B7-H4, HVEM, BTLA, KIR, GAL9, TIM3, A2AR, LAG-3, and phosphatidylserine; and/or (e) a protein, lipid, polysaccharide, or glycolipid expressed on one or more tumor cells and any combination thereof.

Numerous antigens are known in the art that facilitate transport across the blood-brain barrier (see, e.g., Gabathuler R. *Neurobiol. Dis.* 37:48-57 (2010)). Such second antigens include, without limitation, transferrin receptor (TR), insulin receptor (HIR), Insulin-like growth factor receptor (IGFR), low-density lipoprotein receptor related proteins 1 and 2 (LPR-1 and 2), diphtheria toxin receptor, including CRM197 (a non-toxic mutant of diphtheria toxin), llama single domain antibodies such as TMEM 30(A) (Flippase), protein transduction domains such as TAT, Syn-B, or penetratin, poly-arginine or generally positively charged peptides, Angiopep peptides such as ANG1005 (see, e.g., Gabathuler, 2010), and other cell surface proteins that are enriched on blood-brain barrier endothelial cells (see, e.g., Daneman et al. *PLoS One* 5(10):e13741 (2010)).

The multivalent antibodies may recognize the MS4A6A antigen as well as without limitation additional antigens Aβ peptide, antigen or an α-synuclein protein antigen or, Tau protein antigen or, TDP-43 protein antigen or, prion protein antigen or, huntingtin protein antigen, or RAN, translation Products antigen, including the DiPeptide Repeats,(DPRs peptides) composed of glycine-alanine (GA), glycine-proline (GP), glycine-arginine (GR), proline-alanine (PA), or proline-arginine (PR), Insulin receptor, insulin like growth factor receptor. Transferrin receptor or any other antigen that facilitate antibody transfer across the blood brain barrier. In some embodiments, the second polypeptide is transferrin. In some embodiments, the second polypeptide is Tau. In some embodiments, the second polypeptide is Aβ. In some embodiments, the second polypeptide is TREM2. In some embodiments, the second polypeptide is α-synuclein.

The multivalent antibody contains at least one polypeptide chain (and preferably two polypeptide chains), wherein the polypeptide chain or chains comprise two or more variable domains. For instance, the polypeptide chain or chains may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. Similarly, the polypeptide chain or chains may comprise $V_H$-$C_H$1-flexible linker-$V_H$-$C_H$1-Fc region chain; or $V_H$-$C_H$1-$V_H$-$C_H$1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Techniques for making multispecific antibodies include, but are not limited to, recombinant co-expression of two immunoglobulin heavy chain- light chain pairs having different specificities (see Milstein and Cuello *Nature* 305: 537 (1983), WO 93/08829, and Traunecker et al. *EMBO J.* 10:3655 (1991)), and "knob-in-hole" engineering (see, e.g., U.S. Pat. No. 5,731,168). See also WO 2013/026833 (CrossMab). Multi-specific antibodies may also be made by engineering electrostatic steering effects for making antibody Fc- heterodimeric molecules (WO 2009/089004A1); cross-linking two or more antibodies (see, e.g., U.S. Pat. No. 4,676,980); using leucine; using "diabody" technology for making bispecific antibody fragments (see, e.g., Hollinger et al. *Proc. Natl. Acad. Sci. USA* 90:6444-6448 (1993)); and using single-chain Fv (scFv) dimers (see, e.g., Gruber et al. *J. Immunol.* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g., US 2006/0025576). The antibody herein also includes a "Dual Acting FAb" or "DAF" comprising an antigen binding site that binds to multiple MS4A6A (see, US 2008/0069820, for example).

(7) Antibody Variants

In some embodiments of any of the antibodies provided herein, amino acid sequence variants of the antibodies are contemplated. For example, it may be desirable to improve the binding affinity and/or other biological properties of the antibody.

(i) Substitution, Insertion, and Deletion Variants

In some embodiments of any of the antibodies provided herein, antibody variants having one or more amino acid substitutions are provided. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody.

TABLE 1

Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Tyr |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro; and
(6) aromatic: Trp, Tyr, Phe.

For example, non-conservative substitutions can involve the exchange of a member of one of these classes for a member from another class. Such substituted residues can be introduced, for example, into regions of a human antibody that are homologous with non-human antibodies, or into the non-homologous regions of the molecule.

In making changes to the polypeptide or antibody described herein, according to certain embodiments, the hydropathic index of amino acids can be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al. *J. Mol. Biol.*, 157:105-131 (1982). It is known that certain amino acids can be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those which are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0±1); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those which are within ±1 are included, and in certain embodiments, those within ±0.5 are included. One can also identify epitopes from primary amino acid sequences on the basis of hydrophilicity. These regions are also referred to as "epitopic core regions".

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

Amino acid sequence insertions include amino- and/or carboxyl-terminal fusions ranging in length from one residue to polypeptides comprising a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment, such as an Fv fragment).

(ii) Glycosylation Variants

In some embodiments of any of the antibodies provided herein, the antibody is altered to increase or decrease the extent to which the antibody is glycosylated. Addition or deletion of glycosylation sites to an antibody may be conveniently accomplished by altering the amino acid sequence such that one or more glycosylation sites is created or removed.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered. Native antibodies produced by mammalian cells typically comprise a branched, biantennary oligosaccharide that is generally attached by an N-linkage to Asn297 according to Kabat numbering of the CH2 domain of the Fc region. The oligosaccharide may include various carbohydrates, for example, mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the disclosure may be made in order to create antibody variants with certain improved properties.

In one embodiment, antibody variants are provided having a carbohydrate structure that lacks fucose attached (directly or indirectly) to an Fc region. See, e.g., US Patent Publication Nos. 2003/0157108 and 2004/0093621. Examples of publications related to "defucosylated" or "fucose-deficient" antibody variants include: US 2003/0157108; US 2003/0115614; US 2002/0164328; US 2004/0093621; US 2004/0132140; US 2004/0110704; US 2004/0110282; US 2004/0109865; Okazaki et al. *J. Mol. Biol.* 336:1239-1249 (2004); Yamane-Ohnuki et al. *Biotech. Bioeng.* 87:614 (2004). Examples of cell lines capable of producing defucosylated antibodies include Led 3 CHO cells deficient in protein fucosylation (Ripka et al. *Arch. Biochem. Biophys.* 249:533-545 (1986); US 2003/0157108), and knockout cell lines, such as alpha-1,6-fucosyltransferase gene, FUT8, knockout CHO cells (see, e.g., Yamane-Ohnuki et al. *Biotech. Bioeng.* 87: 614 (2004) and Kanda et al. *Biotechnol. Bioeng.* 94(4):680-688 (2006)).

(iii) Modified Constant Regions

In some embodiments of any of the antibodies provided herein, the antibody Fc is an antibody Fc isotypes and/or modifications. In some embodiments, the antibody Fc isotype and/or modification is capable of binding to Fc gamma receptor.

In some embodiments of any of the antibodies provided herein, the modified antibody Fc is an IgG1 modified Fc. In some embodiments, the IgG1 modified Fc comprises one or more modifications. For example, in some embodiments, the IgG1 modified Fc comprises one or more amino acid substitutions (e.g., relative to a wild-type Fc region of the same isotype). In some embodiments, the one or more amino acid substitutions are selected from N297A (Bolt S et al. (1993) *Eur J Immunol* 23:403-411), D265A (Shields et al. (2001) R. *J Biol. Chem.* 276, 6591-6604), L234A, L235A (Hutchins et al. (1995) *Proc Natl Acad Sci USA,* 92:11980-11984; Alegre et al., (1994) *Transplantation* 57:1537-1543. 31; Xu et al., (2000) *Cell Immunol,* 200:16-26), G237A (Alegre et al. (1994) *Transplantation* 57:1537-1543. 31; Xu et al. (2000) *Cell Immunol,* 200:16-26), C226S, C229S, E233P, L234V, L234F, L235E (McEarchern et al., (2007) *Blood,* 109:1185-1192), P331S (Sazinsky et al., (2008) *Proc Natl Acad Sci USA* 2008, 105:20167-20172), S267E, L328F, A330L, M252Y, S254T, and/or T256E, where the amino acid position is according to the EU numbering convention.

In some embodiments of any of the IgG1 modified Fc, the Fc comprises N297A mutation according to EU numbering. In some embodiments of any of the IgG1 modified Fc, the Fc comprises D265A and N297A mutations according to EU numbering. In some embodiments of any of the IgG1 modified Fc, the Fc comprises D270A mutations according to EU numbering. In some embodiments, the IgG1 modified Fc comprises L234A and L235A mutations according to EU numbering. In some embodiments of any of the IgG1 modified Fc, the Fc comprises L234A and G237A mutations according to EU numbering. In some embodiments of any of the IgG1 modified Fc, the Fc comprises L234A, L235A and G237A mutations according to EU numbering. In some embodiments of any of the IgG1 modified Fc, the Fc comprises one or more (including all) of P238D, L328E, E233, G237D, H268D, P271G and A330R mutations according to EU numbering. In some embodiments of any of the IgG1 modified Fc, the Fc comprises one or more of S267E/L328F mutations according to EU numbering. In some embodiments of any of the IgG1 modified Fc, the Fc comprises P238D, L328E, E233D, G237D, H268D, P271G and A330R mutations according to EU numbering. In some embodiments of any of the IgG1 modified Fc, the Fc comprises P238D, L328E, G237D, H268D, P271G and A330R mutations according to EU numbering. In some embodiments of any of the IgG1 modified Fc, the Fc comprises P238D, S267E, L328E, E233D, G237D, H268D, P271G and A330R mutations according to EU numbering. In some embodiments of any of the IgG1 modified Fc, the Fc comprises P238D, S267E, L328E, G237D, H268D, P271G and A330R mutations according to EU numbering. In some embodiments of any of the IgG1 modified Fc, the Fc comprises C226S, C229S, E233P, L234V, and L235A mutations according to EU numbering. In some embodiments of any of the IgG1 modified Fc, the Fc comprises L234F, L235E, and P331S mutations according to EU numbering. In some embodiments of any of the IgG1 modified Fc, the Fc comprises S267E and L328F mutations according to EU numbering. In some embodiments of any of the IgG1 modified Fc, the Fc comprises S267E mutations according to EU numbering. In some embodiments of any of the IgG1 modified Fc, the Fc comprises a substitute of the constant heavy 1 (CH1) and hinge region of IgG1 with CH1 and hinge region of IgG2 (amino acids 118-230 of IgG2 according to EU numbering) with a Kappa light chain.

In some embodiments of any of the IgG1 modified Fc, the Fc includes two or more amino acid substitutions that increase antibody clustering without activating complement as compared to a corresponding antibody having an Fc region that does not include the two or more amino acid substitutions. Accordingly, in some embodiments of any of the IgG1 modified Fc, the IgG1 modified Fc is an antibody comprising an Fc region, where the antibody comprises an amino acid substitution at position E430G and one or more amino acid substitutions in the Fc region at a residue position selected from: L234F, L235A, L235E, S267E, K322A, L328F, A330S, P331S, and any combination thereof according to EU numbering. In some embodiments, the IgG1 modified Fc comprises an amino acid substitution at positions E430G, L243A, L235A, and P331S according to EU numbering. In some embodiments, the IgG1 modified Fc comprises an amino acid substitution at positions E430G and P331S according to EU numbering. In some embodiments, the IgG1 modified Fc comprises an amino acid substitution at positions E430G and K322A according to EU numbering. In some embodiments, the IgG1 modified Fc comprises an amino acid substitution at positions E430G, A330S, and P331S according to EU numbering. In some embodiments, the IgG1 modified Fc comprises an amino acid substitution at positions E430G, K322A, A330S, and P331S according to EU numbering. In some embodiments, the IgG1 modified Fc comprises an amino acid substitution at positions E430G, K322A, and A330S according to EU numbering. In some embodiments, the IgG1 modified Fc comprises an amino acid substitution at positions E430G, K322A, and P331S according to EU numbering.

In some embodiments of any of the IgG1 modified Fc, the IgG1 modified Fc may further comprise herein may be combined with an A330L mutation (Lazar et al. *Proc Natl Acad Sci USA,* 103:4005-4010 (2006)), or one or more of L234F, L235E, and/or P331S mutations (Sazinsky et al. *Proc Natl Acad Sci USA,* 105:20167-20172 (2008)), according to the EU numbering convention, to eliminate complement activation. In some embodiments of any of the IgG1 modified Fc, the IgG1 modified Fc may further comprise one or more of A330L, A330S, L234F, L235E, and/or P331S according to EU numbering. In some embodiments of any of the IgG1 modified Fc, the IgG1 modified Fc may further comprise one or more mutations to enhance the antibody half-life in human serum (e.g., one or more (including all) of M252Y, S254T, and T256E mutations according to the EU numbering convention). In some embodiments of any of the IgG1 modified Fc, the IgG1 modified Fc may further comprise one or more of E430G, E430S, E430F, E430T, E345K, E345Q, E345R, E345Y, S440Y, and/or S440W according to EU numbering.

Other aspects of the present disclosure relate to antibodies having modified constant regions (i.e., Fc regions). An antibody dependent on binding to FcgR receptor to activate targeted receptors may lose its agonist activity if engineered to eliminate FcgR binding (see, e.g., Wilson et al. *Cancer Cell* 19:101-113 (2011); Armour at al. *Immunology* 40:585-593 (2003); and White et al. *Cancer Cell* 27:138-148 (2015)). As such, it is thought that an anti-MS4A6A antibody of the present disclosure with the correct epitope specificity can activate the target antigen, with minimal adverse effects, when the antibody has an Fc domain from a human IgG2 isotype (CH1 and hinge region) or another type of Fc domain that is capable of preferentially binding the inhibitory FcgRIIB r receptors, or a variation thereof.

In some embodiments of any of the antibodies provided herein, the modified antibody Fc is an IgG2 modified Fc. In some embodiments, the IgG2 modified Fc comprises one or more modifications. For example, in some embodiments, the IgG2 modified Fc comprises one or more amino acid substitutions (e.g., relative to a wild-type Fc region of the same isotype). In some embodiments of any of the IgG2 modified Fc, the one or more amino acid substitutions are selected from V234A (Alegre et al. *Transplantation* 57:1537-1543 (1994); Xu et al. *Cell Immunol*, 200:16-26 (2000)); G237A (Cole et al. *Transplantation*, 68:563-571 (1999)); H268Q, V309L, A330S, P331S (US 2007/0148167; Armour et al. *Eur J. Immunol* 29: 2613-2624 (1999); Armour et al. *The Haematology Journal* 1(Suppl. 1):27 (2000); Armour et al. *The Haematology Journal* 1(Suppl. 1):27 (2000)), C219S, and/or C220S (White et al. *Cancer Cell* 27, 138-148 (2015)); S267E, L328F (Chu et al. *Mol Immunol*, 45:3926-3933 (2008)); and M252Y, S254T, and/or T256E according to the EU numbering convention. In some embodiments of any of the IgG2 modified Fc, the Fc comprises an amino acid substitution at positions V234A and G237A according to EU numbering. In some embodiments of any of the IgG2 modified Fc, the Fc comprises an amino acid substitution at positions C219S or C220S according to EU numbering. In some embodiments of any of the IgG2 modified Fc, the Fc comprises an amino acid substitution at positions A330S and P331S according to EU numbering. In some embodiments of any of the IgG2 modified Fc, the Fc comprises an amino acid substitution at positions S267E and L328F according to EU numbering.

In some embodiments of any of the IgG2 modified Fc, the Fc comprises a C127S amino acid substitution according to the EU numbering convention (White et al., (2015) *Cancer Cell* 27, 138-148; Lightle et al. *Protein Sci.* 19:753-762 (2010); and WO 2008/079246). In some embodiments of any of the IgG2 modified Fc, the antibody has an IgG2 isotype with a Kappa light chain constant domain that comprises a C214S amino acid substitution according to the EU numbering convention (White et al. *Cancer Cell* 27:138-148 (2015); Lightle et al. *Protein Sci.* 19:753-762 (2010); and WO 2008/079246).

In some embodiments of any of the IgG2 modified Fc, the Fc comprises a C220S amino acid substitution according to the EU numbering convention. In some embodiments of any of the IgG2 modified Fc, the antibody has an IgG2 isotype with a Kappa light chain constant domain that comprises a C214S amino acid substitution according to the EU numbering convention.

In some embodiments of any of the IgG2 modified Fc, the Fc comprises a C219S amino acid substitution according to the EU numbering convention. In some embodiments of any of the IgG2 modified Fc, the antibody has an IgG2 isotype with a Kappa light chain constant domain that comprises a C214S amino acid substitution according to the EU numbering convention.

In some embodiments of any of the IgG2 modified Fc, the Fc includes an IgG2 isotype heavy chain constant domain 1(CH1) and hinge region (White et al. *Cancer Cell* 27:138-148 (2015)). In certain embodiments of any of the IgG2 modified Fc, the IgG2 isotype CH1 and hinge region comprise the amino acid sequence of 118-230 according to EU numbering. In some embodiments of any of the IgG2 modified Fc, the antibody Fc region comprises a S267E amino acid substitution, a L328F amino acid substitution, or both, and/or a N297A or N297Q amino acid substitution according to the EU numbering convention.

In some embodiments of any of the IgG2 modified Fc, the Fc further comprises one or more amino acid substitution at positions E430G, E430S, E430F, E430T, E345K, E345Q, E345R, E345Y, S440Y, and S440W according to EU numbering. In some embodiments of any of the IgG2 modified Fc, the Fc may further comprise one or more mutations to enhance the antibody half-life in human serum (e.g., one or more (including all) of M252Y, S254T, and T256E mutations according to the EU numbering convention). In some embodiments of any of the IgG2 modified Fc, the Fc may further comprise A330S and P331S.

In some embodiments of any of the IgG2 modified Fc, the Fc is an IgG2/4 hybrid Fc. In some embodiments, the IgG2/4 hybrid Fc comprises IgG2 aa 118 to 260 and IgG4 aa 261 to 447. In some embodiments of any IgG2 modified Fc, the Fc comprises one or more amino acid substitutions at positions H268Q, V309L, A330S, and P331S according to EU numbering.

In some embodiments of any of the IgG1 and/or IgG2 modified Fc, the Fc comprises one or more additional amino acid substitutions selected from A330L, L234F; L235E, or P331S according to EU numbering; and any combination thereof.

In certain embodiments of any of the IgG1 and/or IgG2 modified Fc, the Fc comprises one or more amino acid substitutions at a residue position selected from C127S, L234A, L234F, L235A, L235E, S267E, K322A, L328F, A330S, P331S, E345R, E430G, S440Y, and any combination thereof according to EU numbering. In some embodiments of any of the IgG1 and/or IgG2 modified Fc, the Fc comprises an amino acid substitution at positions E430G, L243A, L235A, and P331S according to EU numbering. In some embodiments of any of the IgG1 and/or IgG2 modified Fc, the Fc comprises an amino acid substitution at positions E430G and P331S according to EU numbering. In some embodiments of any of the IgG1 and/or IgG2 modified Fc, the Fc comprises an amino acid substitution at positions E430G and K322A according to EU numbering. In some embodiments of any of the IgG1 and/or IgG2 modified Fc, the Fc comprises an amino acid substitution at positions E430G, A330S, and P331S according to EU numbering. In some embodiments of any of the IgG1 and/or IgG2 modified Fc, the Fc comprises an amino acid substitution at positions E430G, K322A, A330S, and P331S according to EU numbering. In some embodiments of any of the IgG1 and/or IgG2 modified Fc, the Fc comprises an amino acid substitution at positions E430G, K322A, and A330S according to EU numbering. In some embodiments of any of the IgG1 and/or IgG2 modified Fc, the Fc comprises an amino acid substitution at positions E430G, K322A, and P331S according to EU numbering. In some embodiments of any of the IgG1 and/or IgG2 modified Fc, the Fc comprises an amino acid substitution at positions S267E and L328F according to EU numbering. In some embodiments of any of the IgG1 and/or IgG2 modified Fc, the Fc comprises an amino acid substitution at position C127S according to EU numbering. In some embodiments of any of the IgG1 and/or IgG2 modified Fc, the Fc comprises an amino acid substitution at positions E345R, E430G and S440Y according to EU numbering.

In some embodiments of any of the antibodies provided herein, the modified antibody Fc is an IgG4 modified Fc. In some embodiments, the IgG4 modified Fc comprises one or more modifications. For example, in some embodiments, the IgG4 modified Fc comprises one or more amino acid substitutions (e.g., relative to a wild-type Fc region of the same isotype). In some embodiments of any of the IgG4 modified Fc, the one or more amino acid substitutions are selected from L235A, G237A, S229P, L236E (Reddy et al. *J Immunol* 164:1925-1933(2000)), S267E, E318A, L328F, M252Y, S254T, and/or T256E according to the EU numbering convention. In some embodiments of any of the IgG4 modified Fc, the Fc may further comprise L235A, G237A, and E318A according to the EU numbering convention. In some embodiments of any of the IgG4 modified Fc, the Fc may further comprise S228P and L235E according to the EU numbering convention. In some embodiments of any of the IgG4 modified Fc, the IgG4 modified Fc may further comprise S267E and L328F according to the EU numbering convention.

In some embodiments of any of the IgG4 modified Fc, the IgG4 modified Fc comprises may be combined with an S228P mutation according to the EU numbering convention (Angal et al. *Mol Immunol.* 30:105-108 (1993)) and/or with one or more mutations described in (Peters et al. *J Biol Chem.* 287(29):24525-33 (2012)) to enhance antibody stabilization.

In some embodiments of any of the IgG4 modified Fc, the IgG4 modified Fc may further comprise one or more mutations to enhance the antibody half-life in human serum (e.g., one or more (including all) of M252Y, S254T, and T256E mutations according to the EU numbering convention).

In some embodiments of any of the IgG4 modified Fc, the Fc comprises L235E according to EU numbering. In certain embodiments of any of the IgG4 modified Fc, the Fc comprises one or more amino acid substitutions at a residue position selected from C127S, F234A, L235A, L235E, S267E, K322A, L328F, E345R, E430G, S440Y, and any combination thereof, according to EU numbering. In some embodiments of any of the IgG4 modified Fc, the Fc comprises an amino acid substitution at positions E430G, L243A, L235A, and P331S according to EU numbering. In some embodiments of any of the IgG4 modified Fc, the Fc comprises an amino acid substitution at positions E430G and P331S according to EU numbering. In some embodiments of any of the IgG4 modified Fc, the Fc comprises an amino acid substitution at positions E430G and K322A according to EU numbering. In some embodiments of any of the IgG4 modified Fc, the Fc comprises an amino acid substitution at position E430 according to EU numbering. In some embodiments of any of the IgG4 modified Fc, the Fc region comprises an amino acid substitution at positions E430G and K322A according to EU numbering. In some embodiments of any of the IgG4 modified Fc, the Fc comprises an amino acid substitution at positions S267E and L328F according to EU numbering. In some embodiments of any of the IgG4 modified Fc, the Fc comprises an amino acid substitution at position C127S according to EU numbering. In some embodiments of any of the IgG4 modified Fc, the Fc comprises an amino acid substitution at positions E345R, E430G and S440Y according to EU numbering.

(8) Other Antibody Modifications

In some embodiments of any of the antibodies, the antibody is a derivative. The term "derivative" refers to a molecule that includes a chemical modification other than an insertion, deletion, or substitution of amino acids (or nucleic acids). In certain embodiments, derivatives comprise covalent modifications, including, but not limited to, chemical bonding with polymers, lipids, or other organic or inorganic moieties. In certain embodiments, a chemically modified antigen binding protein can have a greater circulating half-life than an antigen binding protein that is not chemically modified. In certain embodiments, a chemically modified antigen binding protein can have improved targeting capacity for desired cells, tissues, and/or organs. In some embodiments, a derivative antigen binding protein is covalently modified to include one or more water soluble polymer attachments, including, but not limited to, polyethylene glycol, polyoxyethylene glycol, or polypropylene glycol. See, e.g., U.S. Pat. Nos. 4,640,835, 4,496,689, 4,301,144, 4,670,417, 4,791,192 and 4,179,337. In certain embodiments, a derivative antigen binding protein comprises one or more polymer, including, but not limited to, monomethoxypolyethylene glycol, dextran, cellulose, copolymers of ethylene glycol/propylene glycol, carboxymethylcellulose, polyvinyl pyrrolidone, poly-1, 3-dioxolane, poly-1,3,6-trioxane, ethylene/maleic anhydride copolymer, polyaminoacids (either homopolymers or random copolymers), poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers.

In certain embodiments, a derivative is covalently modified with polyethylene glycol (PEG) subunits. In certain embodiments, one or more water-soluble polymer is bonded at one or more specific position, for example at the amino terminus, of a derivative. In certain embodiments, one or more water-soluble polymer is randomly attached to one or more side chains of a derivative. In certain embodiments, PEG is used to improve the therapeutic capacity for an antigen binding protein. In certain embodiments, PEG is used to improve the therapeutic capacity for a humanized antibody. Certain such methods are discussed, for example, in U.S. Pat. No. 6,133,426, which is hereby incorporated by reference for any purpose.

Peptide analogs are commonly used in the pharmaceutical industry as non-peptide drugs with properties analogous to those of the template peptide. These types of non-peptide compound are termed "peptide mimetics" or "peptidomimetics." Fauchere, *J. Adv. Drug Res.*, 15:29 (1986); and Evans et al. *J. Med. Chem.*, 30:1229 (1987), which are incorporated herein by reference for any purpose. Such compounds are often developed with the aid of computerized molecular modeling. Peptide mimetics that are structurally similar to therapeutically useful peptides can be used to produce a similar therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from: —CH$_2$NH—, —CH$_2$S—, —CH$_2$—CH$_2$—, —CH=CH- (cis and trans), —COCH$_2$—, —CH(OH)CH$_2$—, and —CH$_2$SO—, by methods well known in the art. Systematic substitution of one or more amino acids of a consensus sequence with a D-amino acid of the same type (e.g., D-lysine in place of L-lysine) can be used in certain embodiments to generate more stable peptides. In addition, constrained peptides comprising a consensus sequence or a substantially identical consensus sequence variation can be generated by methods known in the art (Rizo and Gierasch *Ann. Rev. Biochem.*, 61:387 (1992), incorporated herein by reference for any purpose); for example, by adding internal cysteine residues capable of forming intramolecular disulfide bridges which cyclize the peptide.

Drug conjugation involves coupling of a biological active cytotoxic (anticancer) payload or drug to an antibody that specifically targets a certain tumor marker (e.g. a polypeptide that, ideally, is only to be found in or on tumor cells). Antibodies track these proteins down in the body and attach themselves to the surface of cancer cells. The biochemical reaction between the antibody and the target protein (antigen) triggers a signal in the tumor cell, which then absorbs or internalizes the antibody together with the cytotoxin. After the ADC is internalized, the cytotoxic drug is released and kills the cancer. Due to this targeting, ideally the drug has lower side effects and gives a wider therapeutic window than other chemotherapeutic agents. Technics to conjugate antibodies are disclosed are known in the art (see, e.g., Jane de Lartigue OncLive Jul. 5, 2012; ADC Review on antibody-drug conjugates; and Ducry et al. *Bioconjugate Chemistry* 21 (1):5-13 (2010).

III. Nucleic Acids, Vectors, and Host Cells

Anti-MS4A6A antibodies of the present disclosure may be produced using recombinant methods and compositions, e.g., as described in U.S. Pat. No. 4,816,567. In some embodiments, isolated nucleic acids having a nucleotide sequence encoding any of the anti-MS4A6A antibodies of the present disclosure are provided. Such nucleic acids may encode an amino acid sequence comprising the $V_L$ and/or an amino acid sequence comprising the $V_H$ of the anti-MS4A6A antibody (e.g., the light and/or heavy chains of the antibody). In some embodiments, one or more vectors (e.g., expression vectors) comprising such nucleic acids are provided. In some embodiments, a host cell comprising such nucleic acid is also provided. In some embodiments, the host cell comprises (e.g., has been transduced with): (1) a vector comprising a nucleic acid that encodes an amino acid sequence comprising the $V_L$ of the antibody and an amino acid sequence comprising the $V_H$ of the antibody, or (2) a first vector comprising a nucleic acid that encodes an amino acid sequence comprising the $V_L$ of the antibody and a second vector comprising a nucleic acid that encodes an amino acid sequence comprising the $V_H$ of the antibody. In some embodiments, the host cell is eukaryotic, e.g., a Chinese Hamster Ovary (CHO) cell or lymphoid cell (e.g., Y0, NS0, Sp20 cell). Host cells of the present disclosure also include, without limitation, isolated cells, in vitro cultured cells, and ex vivo cultured cells.

Methods of making an anti-MS4A6A antibody of the present disclosure are provided. In some embodiments, the method includes culturing a host cell of the present disclosure comprising a nucleic acid encoding the anti-MS4A6A antibody, under conditions suitable for expression of the antibody. In some embodiments, the antibody is subsequently recovered from the host cell (or host cell culture medium).

For recombinant production of an anti-MS4A6A antibody of the present disclosure, a nucleic acid encoding the anti-MS4A6A antibody is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable vectors comprising a nucleic acid sequence encoding any of the anti-MS4A6A antibodies of the present disclosure, or cell-surface expressed fragments or polypeptides thereof polypeptides (including antibodies) described herein include, without limitation, cloning vectors and expression vectors. Suitable cloning vectors can be constructed according to standard techniques, or may be selected from a large number of cloning vectors available in the art. While the cloning vector selected may vary according to the host cell intended to be used, useful cloning vectors generally have the ability to self-replicate, may possess a single target for a particular restriction endonuclease, and/or may carry genes for a marker that can be used in selecting clones comprising the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Suitable host cells for cloning or expression of antibody-encoding vectors include prokaryotic or eukaryotic cells. For example, anti-MS4A6A antibodies of the present disclosure may be produced in bacteria, in particular when glycosylation and Fc effector function are not needed. For expression of antibody fragments and polypeptides in bacteria (e.g., U.S. Pat. Nos. 5,648,237, 5,789,199, and 5,840,523. After expression, the antibody may be isolated from the bacterial cell paste in a soluble fraction and can be further purified.

In addition to prokaryotes, eukaryotic microorganisms, such as filamentous fungi or yeast, are also suitable cloning or expression hosts for antibody-encoding vectors, including fungi and yeast strains whose glycosylation pathways have been "humanized," resulting in the production of an antibody with a partially or fully human glycosylation pattern (e.g., Gerngross *Nat. Biotech.* 22:1409-1414 (2004); and Li et al. *Nat. Biotech.* 24:210-215 (2006)).

Suitable host cells for the expression of glycosylated antibody can also be derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells. Plant cell cultures can also be utilized as hosts (e.g., U.S. Pat. Nos. 5,959,177, 6,040,498, 6,420,548, 7,125,978, and 6,417,429, describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al. *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al. *Annals N.Y. Acad. Sci.* 383:44-68 (1982); MRC 5 cells; and FS4 cells. Other useful mammalian host cell lines include Chinese hamster ovary (CHO) cells, including DHFR- CHO cells (Urlaub et al. *Proc. Natl. Acad. Sci. USA* 77:4216 (1980)); and myeloma cell lines such as Y0, NS0and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, NJ), pp. 255-268 (2003).

IV. Pharmaceutical Compositions/Formulations

Provided herein are pharmaceutical compositions and/or pharmaceutical formulations comprising the anti-MS4A6A antibodies of the present disclosure and a pharmaceutically acceptable carrier.

In some embodiments, pharmaceutically acceptable carrier preferably are nontoxic to recipients at the dosages and concentrations employed. The antibodies described herein may be formulated into preparations in solid, semi-solid, liquid or gaseous forms. Examples of such formulations include, without limitation, tablets, capsules, powders, granules, ointments, solutions, suppositories, injections, inhalants, gels, microspheres, and aerosols. Pharmaceutically acceptable carriers can include, depending on the formulation desired, pharmaceutically-acceptable, non-toxic carriers of diluents, which are vehicles commonly used to formulate pharmaceutical compositions for animal or human administration. In certain embodiments, the pharmaceutical composition can comprise formulation materials for modifying, maintaining or preserving, for example, the pH, osmolarity, viscosity, clarity, color, isotonicity, odor, sterility, stability, rate of dissolution or release, adsorption or penetration of the composition.

In certain embodiments, pharmaceutically acceptable carriers include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. Further examples of formulations that are suitable for various types of administration can be found in Remington: The Science and Practice of Pharmacy, Pharmaceutical Press 22nd ed. (2013). For a brief review of methods for drug delivery, see, Langer, Science 249:1527-1533 (1990).

Formulations suitable for parenteral administration include aqueous and non-aqueous, isotonic sterile injection solutions, which can comprise antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Formulations may be optimized for retention and stabilization in the brain or central nervous system. When the agent is administered into the cranial compartment, it is desirable for the agent to be retained in the compartment, and not to diffuse or otherwise cross the blood brain barrier. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of the antibody, such as an anti-MS4A6A antibody of the present disclosure, in a biodegradable or bioerodible implant. The rate of release of the therapeutically active agent is controlled by the rate of transport through the polymeric matrix, and the biodegradation of the implant. Implants may be particles, sheets, patches, plaques, fibers, microcapsules and the like and may be of any size or shape compatible with the selected site of insertion. Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the subject disclosure. Hydrogels are typically a copolymer material, characterized by the ability to imbibe a liquid.

V. Therapeutic Uses

As disclosed herein, anti-MS4A6A antibodies of the present disclosure may be used for preventing, reducing risk, or treating diseases and disorders. In some embodiments, an anti-MS4A6A antibody of the present disclosure is effective at preventing, reducing risk, or treating Alzheimer's disease, late onset Alzheimer's disease, and cognitive impairment.

MS4A6A as a Disease Target

Genome wide association studies have identified various members of the MS4A family are associated with Alzheimer's disease. These are MS4A2, MS4A3, MS4A4A, MS4A4E, MS4A6A, and MS4A6E. Certain SNPs associated with Alzheimer's disease risk are located in non-coding regions, including rs610932, rs583791, and rs667897; the intergenic region between MS4A4E and MS4A6A (rs670139); and rs7232, located in the coding region of MS4A6A. Three SNPs in the MS4A gene cluster have been associated with an increased risk of late-onset Alzheimer's disease, including rs4938933 in MS4A4A, rs670139 in MS4A4E, and rs610932 in MS4A6A (Hollingworth et al., 2011, Nat Genetics, 43:429-435; Naj et al., 2011, Nature Genetics, 43:436-441; Antunez et al., 2011, Genome Medicine, 3, article 33; Ma et al, 2015 Mol Neurobiol 51:1240-1248). Additionally, MS4A4A locus SNPs (rs2304933 and rs2304935) associated with higher levels of MS4A4A and increased Alzheimer's disease risk, including late-onset Alzheimer's disease (LOAD) (Allen et al., 2012, Neurology, 79:221-228). SNPs can serve as valuable genetic biomarkers. For example, a SNP can be associated with disease risk or susceptibility, wherein a specific allele or more than one specific allele of the SNP is associated with increased disease risk or susceptibility (e.g., a susceptibility allele). Alternatively, a SNP can be associated with reduced risk of disease (e.g., a protective allele).

Three SNPs associated with Alzheimer's disease are in strong linkage disequilibrium: rs583791(T) allele, rs7232(T) allele, and rs610932(G) allele are correlated and are major (most frequent) alleles associated with increased Alzheimer's disease risk or susceptibility; rs583791(C) allele, rs7232(A) allele, and rs610932(T) allele are correlated and are minor (less frequent) alleles associated with decreased Alzheimer's disease risk. In some embodiments that may be combined with any of the preceding embodiments, the present disclosure provides a method for preventing, reducing the risk, or treating a neurodegenerative disease, disorder, or condition in an individual having at least one genetic allele associated with Alzheimer's disease risk or susceptibility, the method comprising administering to the individual in need thereof a therapeutically effective amount of an anti-MS4A6A antibody. In some embodiments that may be combined with any of the preceding embodiments, the genetic allele associated with increased Alzheimer's disease risk or susceptibility is rs583791(C) allele. In some embodiments that may be combined with any of the preceding embodiments, the genetic allele associated with increased Alzheimer's disease risk or susceptibility is rs7232(T) allele. In some embodiments that may be combined with any of the preceding embodiments, the genetic allele associated with increased Alzheimer's disease risk or susceptibility is rs610932(G) allele. In some embodiments that may be combined with any of the preceding embodiments, the genetic allele associated with increased Alzheimer's disease risk or susceptibility is associated with decreased or reduced expression or activity of MS4A6A. In some embodiments that may be combined with any of the preceding embodiments, the genetic allele associated with increased Alzheimer's disease risk or susceptibility is associated with decreased or reduced cell surface expression or activity of MS4A6A. In some embodiments that may be combined with any of the preceding embodiments, the genetic allele associated with increased Alzheimer's disease risk or susceptibility is associated with loss of function or reduced function of MS4A6A. In some embodiments that may be combined with any of the preceding embodiments, the individual having at least one genetic allele associated with a neurodegenerative disease, disorder, or condition is homozygous for the at least one genetic allele. In some embodiments that may be combined with any of the preceding embodiments, the individual having at least one genetic allele associated with a neurodegenerative disease, disorder, or condition is heterozygous for the at least one genetic allele.

In certain aspects of the present disclosure, the methods provided herein of administering to an individual in need thereof an anti-MS4A6A antibody increase the expression or activity of MS4A6A, increase or restore proper cell surface expression or localization of MS4A6A, or otherwise correct the biochemical or physiological defect associated with the individual having a neurodegenerative risk allele, such as rs583791(T) allele, rs7232(T) allele, or rs610932(G) allele. In some embodiments that may be combined with any of the preceding embodiments, the present disclosure provides a method for increasing MS4A6A expression or activity in an individual in need thereof, wherein the individual has at least one Alzheimer's disease risk or susceptibility allele selected from the group consisting of rs583791(T), rs7232(T), or rs610932(G), the method comprising administering to the individual an anti-MS4A6A antibody, thereby increasing MS4A6A expression or activity. In some embodiments that may be combined with any of the preceding embodiments, the present disclosure provides a method for increasing or restoring cell surface expression or localization of MS4A6A in an individual in need thereof, wherein the individual has at least one Alzheimer's disease risk or susceptibility allele selected from the group consisting of rs583791(T), rs7232(T), and rs610932(G), the method comprising administering to the individual an anti-MS4A6A antibody, thereby increasing or restoring cell surface expression or localization of MS4A6A.

In some embodiments, the present disclosure provides a method of selecting an individual for treatment with an anti-MS4A6A antibody, the method comprising: a) obtaining a sample (e.g., blood sample) from the individual; b) determining which genetic allele associated with increased risk of a neurodegenerative disease, disorder, or condition is present in the individual; and c) selecting the individual for treatment with an anti-MS4A6A antibody, wherein the individual has one or more genetic alleles associated with increased risk of a neurodegenerative disease, disorder, or condition. In some embodiments, the genetic allele associated with increased risk of a neurodegenerative disease, disorder, or condition is rs583791(C) allele. In some embodiments that may be combined with any of the preceding embodiments, the genetic allele associated with increased risk of a neurodegenerative disease, disorder, or condition is rs7232(T) allele. In some embodiments that may be combined with any of the preceding embodiments, the genetic allele associated with increased risk of a neurodegenerative disease, disorder, or condition is rs610932(G) allele. Any suitable method known to one of skill in the art for obtaining a sample from an individual, such as a blood sample, may be used. Further, it will be appreciated that any method known to one of skill in the art for determining which genetic risk or susceptibility allele the individual has, for example, by SNP analysis, may be used.

The methods provided herein find use in preventing, reducing risk, or treating an individual having a neurodegenerative disease, disorder, or condition. In some embodiments, the present disclosure provides a method for preventing, reducing risk, or treating an individual having a neurodegenerative disorder, the method comprising administering to the individual in need thereof a therapeutically effective amount of an anti-MS4A6A antibody.

In some embodiments, the present disclosure provides a method for preventing, reducing the risk, or treating an individual having Alzheimer's disease, the method comprising administering to the individual in need thereof a therapeutically effective amount of an anti-MS4A6A antibody.

In some embodiments, the present disclosure provides a method for preventing, reducing the risk, or treating an individual having late onset Alzheimer's disease, the method comprising administering to the individual in need thereof a therapeutically effective amount of an anti-MS4A6A antibody.

In some embodiments, the present disclosure provides a method for preventing, reducing the risk, or treating an individual having mild cognitive impairment, the method comprising administering to the individual in need thereof a therapeutically effective amount of an anti-MS4A6A antibody.

In some embodiments, the present disclosure provides a method for preventing, reducing risk, or treating an individual having a disease, disorder, or condition associated with decreased or reduced expression or activity of MS4A6A, the method comprising administering to an individual in need thereof a therapeutically effective amount of an anti-MS4A6A antibody. In some embodiments, the present disclosure provides a method for preventing, reducing risk, or treating an individual having a disease, disorder, or condition associated with decreased or reduced cell surface expression or activity of MS4A6A, the method comprising administering to an individual in need thereof a therapeutically effective amount of an anti-MS4A6A antibody. In some embodiments, the disease, disorder, or condition associated with decreased or reduced expression or activity of MS4A6A is a neurodegenerative disease, disorder, or condition, such as, for example, Alzheimer's disease.

In certain embodiments, loss of function of MS4A6A, reduced function of MS4A6A, decreased or reduced expression or activity of MS4A6A, or decreased or reduced cell surface expression of MS4A6A is associated with increased risk of having or developing a neurodegenerative disease, disorder, or condition, such as Alzheimer's disease.

In some embodiments, the present disclosure provides a method for preventing, reducing risk, or treating a disease, disorder, or condition associated with decreased or reduced activity of MS4A6A, the method comprising administering to an individual having decreased or reduced activity of MS4A6A a therapeutically effective amount of an anti-MS4A6A antibody. In some embodiments, the present disclosure provides a method for preventing, reducing risk, or treating a disease, disorder, or condition associated with loss of function of MS4A6A, the method comprising administering to an individual having decreased or reduced activity of MS4A6A a therapeutically effective amount of an anti-MS4A6A antibody. In some embodiments, the present disclosure provides a method for preventing, reducing risk, or treating a disease, disorder, or condition associated with decreased or reduced expression of MS4A6A, the method comprising administering to an individual having decreased or reduced expression of MS4A6A a therapeutically effective amount of an anti-MS4A6A antibody. In some embodiments, the present disclosure provides a method for preventing, reducing risk, or treating a disease, disorder, or condition associated with improper or incorrect cellular localization of MS4A6A, the method comprising administering to an individual having improper or incorrect localization of MS4A6A a therapeutically effective amount of an anti-MS4A6A antibody. In certain aspects of the present disclosure, administering to an individual in need thereof a therapeutically effective amount of an anti-MS4A6A leads to increased expression of MS4A6AJ, leads to increased activity of MS4A6A, leads to proper or correct cellular localization of MS4A6A, leads to increased cell surface expression of MS4A6A, and/or leads to gain of function of MS4A6A in the individual.

In some aspects, a disease, disorder, or condition associated with decreased or reduced activity of MS4A6A, associated with loss of function of MS4A6A, associated with decreased or reduced expression of MS4A6A, or associated with improper or incorrect cellular localization of MS4A6A is, at least in part, a result of a genetic defect or deficit associated with or linked to the MS4A6A gene.

In some aspects, a disease, disorder, or condition associated with decreased or reduced activity of MS4A6A, associated with loss of function of MS4A6A, associated with decreased or reduced expression of MS4A6A, or associated with improper or incorrect cellular localization of MS4A6A is, at least in part, a result of normal aging.

Other aspects of the present disclosure relate to a method of preventing, reducing risk, or treating an individual having a disease, disorder, or injury selected from the group consisting of frontotemporal dementia, Alzheimer's disease, mild cognitive impairment, vascular dementia, vascular dementia, seizures, retinal dystrophy, a traumatic brain injury, a spinal cord injury, long-term depression, atherosclerotic vascular diseases, undesirable symptoms of normal aging, dementia, mixed dementia, Creutzfeldt-Jakob disease, normal pressure hydrocephalus, amyotrophic lateral sclerosis, Huntington's disease, taupathy disease, stroke, acute trauma, chronic trauma, lupus, acute and chronic colitis, Crohn's disease, inflammatory bowel disease, ulcerative colitis, malaria, essential tremor, central nervous system lupus, Behcet's disease, Parkinson's disease, dementia with Lewy bodies, multiple system atrophy, degenerative disc disease, Shy-Drager syndrome, progressive supranuclear palsy, cortical basal ganglionic degeneration, acute disseminated encephalomyelitis, granulomatous disorders, Sarcoidosis, diseases of aging, age related macular degeneration, glaucoma, retinitis pigmentosa, retinal degeneration, respiratory tract infection, sepsis, eye infection, systemic infection, inflammatory disorders, arthritis, multiple sclerosis, metabolic disorder, obesity, insulin resistance, type 2 diabetes, tissue or vascular damage, an injury, inflammatory cell debris or protein aggregates, abnormal circulating myeloid cells, unhealthy aging, age-related cognitive impairment, age-related brain atrophy, age-associated traits, including without limitation inflammation, neuronal loss, and cognitive deficits, such as cognitive deficits in the absence of known brain disease, including cognitive deficits of the frontal cerebral cortex of an older individual and, one or more undesirable symptoms of normal aging, comprising administering to the individual a therapeutically effective amount of the anti-MS4A6A antibody of any of the preceding embodiments. Other aspects of the present disclosure relate to an anti-MS4A6A antibody of any of the preceding embodiments for use in preventing, reducing risk, or treating an individual having a disease, disorder, or injury selected from the group consisting of frontotemporal dementia, Alzheimer's disease, vascular dementia, seizures, retinal dystrophy, a traumatic brain injury, a spinal cord injury, long-term depression, atherosclerotic vascular diseases, undesirable symptoms of normal aging, dementia, mixed dementia, Creutzfeldt-Jakob disease, normal pressure hydrocephalus, amyotrophic lateral sclerosis, Huntington's disease, taupathy disease, stroke, acute trauma, chronic trauma, lupus, acute and chronic colitis, Crohn's disease, inflammatory bowel disease, ulcerative colitis, malaria, essential tremor, central nervous system lupus, Behcet's disease, Parkinson's disease, dementia with Lewy bodies, multiple system atrophy, degenerative disc disease, Shy-Drager syndrome, progressive supranuclear palsy, cortical basal ganglionic degeneration, acute disseminated encephalomyelitis, granulomartous disorders, Sarcoidosis, diseases of aging, age related macular degeneration, glaucoma, retinitis pigmentosa, retinal degeneration, respiratory tract infection, sepsis, eye infection, systemic infection, inflammatory disorders, arthritis, multiple sclerosis, metabolic disorder, obesity, insulin resistance, type 2 diabetes, tissue or vascular damage, an injury, inflammatory cell debris or protein aggregates, abnormal circulating myeloid cells, unhealthy aging, age-related cognitive impairment, age-related brain atrophy, age-associated traits, including without limitation inflammation, neuronal loss, and cognitive deficits, such as cognitive deficits in the absence of known brain disease, including cognitive deficits of the frontal cerebral cortex of older individual, and one or more undesirable symptoms of normal aging. Other aspects of the present disclosure relate to an anti-MS4A6A antibody of any of the preceding embodiments for use in preventing or reducing metastasis. Other aspects of the present disclosure relate to an anti-MS4A6A antibody of any of the preceding embodiments for use in preventing, reducing risk, or treating an individual having cancer.

Other aspects of the present disclosure relate to use of an anti-MS4A6A antibody of any of the preceding embodiments in the manufacture of a medicament for preventing, reducing risk, or treating an individual having a disease, disorder, or injury selected from the group consisting of frontotemporal dementia, Alzheimer's disease, late-onset Alzheimer's disease, mild cognitive impairment, vascular dementia, seizures, retinal dystrophy, a traumatic brain injury, a spinal cord injury, long-term depression, atherosclerotic vascular diseases, undesirable symptoms of normal aging, dementia, mixed dementia, Creutzfeldt-Jakob disease, normal pressure hydrocephalus, amyotrophic lateral sclerosis, Huntington's disease, taupathy disease, stroke, acute trauma, chronic trauma, lupus, acute and chronic colitis, Crohn's disease, inflammatory bowel disease, ulcerative colitis, malaria, essential tremor, central nervous system lupus, Behcet's disease, Parkinson's disease, dementia with Lewy bodies, multiple system atrophy, degenerative disc disease, Shy-Drager syndrome, progressive supranuclear palsy, cortical basal ganglionic degeneration, acute disseminated encephalomyelitis, granulomartous disorders, Sarcoidosis, diseases of aging, age related macular degeneration, glaucoma, retinitis pigmentosa, retinal degeneration, respiratory tract infection, sepsis, eye infection, systemic infection, inflammatory disorders, arthritis, multiple sclerosis, metabolic disorder, obesity, insulin resistance, type 2 diabetes, tissue or vascular damage, an injury, inflammatory cell debris or protein aggregates, abnormal circulating myeloid cells, unhealthy aging, age-related cognitive impairment, age-related brain atrophy, age-associated traits, including without limitations inflammation, neuronal loss, and cognitive deficits, such as cognitive deficits in the absence of known brain disease, including cognitive deficits of the frontal cerebral cortex of older individual and one or more undesirable symptoms of normal aging. Other aspects of the present disclosure relate to a method of preventing, reducing risk, or treating an individual having a disease, disorder, or injury selected from the group consisting of frontotemporal dementia, progressive supranuclear palsy, Alzheimer's disease, late-onset Alzheimer's disease, mild cognitive impairment, vascular dementia, seizures, retinal dystrophy, amyotrophic lateral sclerosis, traumatic brain injury, a spinal cord injury, dementia, stroke, Parkinson's disease, acute disseminated encephalomyelitis, retinal degeneration, age related macular degeneration, glaucoma, multiple sclerosis, septic shock, bacterial infection, arthritis, and osteoarthritis, comprising administering to the individual a therapeutically effective amount of the anti-MS4A6A antibody of any of the preceding embodiments. Other aspects of the present disclosure relate to an anti-MS4A6A antibody of any of the preceding embodiments for use in preventing, reducing risk, or treating an individual having a disease, disorder, or injury selected from the group consisting of frontotemporal dementia, progressive suprariuclear palsy, Alzheimer's disease, late-onset Alzheimer's disease, mild cognitive impairment, vascular dementia, seizures, retinal dystrophy, amyotrophic lateral sclerosis, traumatic brain injury, a spinal cord injury, dementia, stroke, Parkinson's disease, acute disseminated encephalomyelitis, retinal degeneration, age related macular degeneration, glaucoma, multiple sclerosis, septic shock, bacterial infection, arthritis, and osteoarthritis. Other aspects of the present disclosure relate to use of an anti-MS4A6A antibody of any of the preceding embodiments in the manufacture of a medicament for preventing, reducing risk, or treating an individual having a disease, disorder, or injury selected from the group consisting of frontotemporal dementia, progressive supranuclear palsy, Alzheimer's disease, vascular dementia, seizures, retinal dystrophy, amyotrophic lateral sclerosis, traumatic brain injury, a spinal cord injury, dementia, stroke, Parkinson's disease, acute disseminated encephalomyelitis, retinal degeneration, age related macular degeneration, glaucoma, multiple sclerosis, septic shock, bacterial infection, arthritis, and osteoarthritis.

Several genes in the MS4A locus have been associated with the inflammatory response, including MS4A6A. (Karch and Goate, 2015, Biol Psychiatry, 77:43-51). Additionally, overexpression of MS4A family genes increased activation of T cells and promoted trafficking of T cells across the blood brain barrier. Activated T cells interact with microglia, causing microglia to activate, resulting in the release of pro-inflammatory cytokines, leading to damage of neurons. Overexpression of MS4A4B reduced T cell apoptosis, whereas knockdown of MS4A4B promoted T cells to undergo apoptosis. (Ma et al., 2015, Mol Neurobiol, 51:1240-1248.)

Autoinflammatory diseases are a group of clinical conditions, different from autoimmune syndromes. Autoinflammatory diseases are characterized by episodes of unprovoked inflammation, due to dysregulation of the innate immune system, without autoreactive T lymphocytes and autoantibodies and are therefore different from classical autoimmune diseases. Two groups of autoinflammatory diseases have been classified: monogenic autoinflammatory diseases and multifactorial autoinflammatory diseases. In some embodiments, an autoinflammatory disorder to be prevented or treated by the methods of the present disclosure includes, but is not limited to, monogenic autoinflammatory diseases such as familial Mediterranean fever (FMF), periodic fever associated with mevalonate kinase deficiency (hyperimmunoglobulin D syndrome), TNF receptor-associated periodic syndrome (TRAPS), cryopyrin-associated periodic syndrome (CAPS), NLRP12-associated autoinflammatory disorders (e.g., NALP12-associated periodic fever), deficiency of interleukin-1 receptor antagonist (DIRA), pyogenic arthritis-pyoderma gangrenosum and acne (PAPA) syndrome, Majeed syndrome, Blau's syndrome, hyperimmuno globulinemia W with periodic fever syndrome (HIDS), familial cold autoinflammatory syndrome (FCAS), Muckle-Wells syndrome (MWS), and neonatal onset of multisystemic inflammatory disorder (NOMID). In some embodiments, an autoinflammatory disorder to be prevented or treated by the methods of the present disclosure includes, but is not limited to, multifactorial autoinflammatory diseases such as include periodic fever, aphthous stomatitis, pharyngitis, and adenopathy syndrome (PFAPA), Behcet's disease, systemic juvenile idiopathic arthritis (sJIA), Still's disease, adult-onset Still's disease (AOSD), Crohn's disease, Schnitzler's syndrome, Sweet's syndrome, Chronic recurrent multifocal osteomyelitis (CRMO), synovitis acne pustulosis hyperostosis osteitis syndrome (SAPHO), and adult-onset Still disease. (See Ciccarelli et al., 2013, Curr Med Chem, 21:261-269.)

Although MS4A genes are poorly characterized, an important role in immunity has been shown for several members of this cluster, including MS4A1, MS4A2, and MS4A4B (Zuccolo et al., 2010, PLoS One; Zuccolo et al., 2013, Front Immmunol, 4:195).

Autoimmune diseases arise from an abnormal immune response to normal body tissue. In some embodiments, an autoimmune disease or disorder to be prevented or treated by the method of the present disclosure includes, but is not limited to, Addison's disease, agammaglobulinemia, alopecia areata, amyloidosis, ankylosing spondylitis, Anti-GBM/Anti-TBM nephritis, antiphospholipid syndrome, autoimmune angioedema, autoimmune dysautonomia, autoimmune encephalomyelitis, autoimmune hepatitis, autoimmune inner ear disease (AIED), autoimmune myocarditis, autoimmune pancreatitis, autoimmune retinopathy, autoimmune urticaria, axonal & neuronal neuropathy (AMAN), Balódisease, Behcet's disease, benign mucosal pemphigoid, bullous pemphigoid, Castleman disease (CD), celiac disease, Chagas disease, chronic inflammatory demyelinating polyneuropathy (CIDP), chronic recurrent multifocal osteomyelitis (CRMO), Churg-Strauss, cicatricial pemphigoid, Cogan's syndrome, cold agglutinin disease, congenital heart block, coxsackie myocarditis, CREST syndrome, Crohn's disease, dermatitis herpetiformis, dermatomyositis, Devic's disease (neuromyelitis optica), discoid lupus, Dressler's syndrome, endometriosis, eosinophilic esophagitis (EoE), eosinophilic fasciitis, erythema nodosum, essential mixed cryoglobulinemia, Evans syndrome, fibromyalgia, fibrosing alveolitis, giant cell arteritis (temporal arteritis), giant cell myocarditis, glomerulonephritis, Goodpasture's syndrome, granulomatosis with Polyangiitis, Graves' disease, Guillain-Barre syndrome, Hashimoto's thyroiditis, hemolytic anemia, Henoch-Schonlein purpura (HSP), herpes gestationis or pemphigoid gestationis (PG), hypogammalglobulinemia, IgA Nephropathy, IgG4-related sclerosing disease, immune thrombocytopenic purpura (ITP), inclusion body myositis (IBM), interstitial cystitis (IC), juvenile arthritis, juvenile diabetes (Type 1 diabetes), juvenile myositis (JM), Kawasaki disease, Lambert-Eaton syndrome, leukocytoclastic vasculitis, lichen planus, lichen sclerosis, ligneous conjunctivitis, linear IgA disease (LAD), lupus, lyme disease chronic, Meniere's disease, microscopic polyangiitis (MPA), mixed connective tissue disease (MCTD), Mooren's ulcer, Mucha-Habermann disease, multiple sclerosis, myasthenia gravis, myositis, narcolepsy, neuromyelitis optica, neutropenia, ocular cicatricial pemphigoid, optic neuritis, palindromic rheumatism (PR), PANDAS, paraneoplastic cerebellar degeneration (PCD), paroxysmal nocturnal hemoglobinuria (PNH), Parry Romberg syndrome, pars planitis (peripheral uveitis), Parsonnage-Turner syndrome, pemphigus, peripheral neuropathy, perivenous encephalomyelitis, pernicious anemia (PA), POEMS syndrome, polyarteritis nodosa, polyglandular syndromes type I, II, and III, polymyalgia rheumatica, polymyositis, postmyocardial infarction syndrome, postpericardiotomy syndrome, primary biliary cirrhosis, primary sclerosing cholangitis, progesterone dermatitis, psoriasis, psoriatic arthritis, pure red cell aplasia (PRCA), pyoderma gangrenosum, Raynaud's phenomenon, reactive arthritis, reflex sympathetic dystrophy, relapsing polychondritis, restless legs syndrome (RLS), retroperitoneal fibrosis, rheumatic fever, rheumatoid arthritis, sarcoidosis, Schmidt syndrome, scleritis, scleroderma, Sjogren's syndrome, sperm & testicular autoimmunity, stiff person syndrome (SPS), subacute bacterial endocarditis (SBE), Susac's syndrome, sympathetic ophthalmia (SO), Takayasu's arteritis, temporal arteritis/giant cell arteritis, thrombocytopenic purpura (TTP), Tolosa-Hunt syndrome (THS), transverse myelitis, type 1 diabetes, ulcerative colitis (UC), undifferentiated connective tissue disease (UCTD), uveitis, vasculitis, vitiligo, and Wegener's granulomatosis (or Granulomatosis with Polyangiitis (GPA)).

In some embodiments, a subject or individual is a mammal. Mammals include, without limitation, domesticated animals (e.g., cows, sheep, cats, dogs, and horses), primates (e.g., humans and non-human primates such as monkeys), rabbits, and rodents (e.g., mice and rats). In some embodiments, the subject or individual is a human.

An antibody provided herein (and any additional therapeutic agent) can be administered by any suitable means, including parenteral, intrapulmonary, intranasal, intralesional administration, intracerobrospinal, intracranial, intraspinal, intrasynovial, intrathecal, oral, topical, or inhalation routes. Parenteral infusions include intramuscular, intravenous administration as a bolus or by continuous infusion over a period of time, intraarterial, intra-articular, intraperitoneal, or subcutaneous administration. In some embodiments, the administration is intravenous administration. In some embodiments, the administration is subcutaneous. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies provided herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the disclosure (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 1 μg/kg to 15 mg/kg (e.g., 0.1 mg/kg-10 mg/kg) of antibody can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g., every week or every three weeks (e.g., such that the patient receives from about two to about twenty, or e.g., about six doses of the antibody). In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. An initial higher loading dose, followed by one or more lower doses may be administered. However, other dosage regimens may be useful. The progress of this therapy is easily monitored by conventional techniques and assays.

VI. Diagnostic Uses

In some embodiments of any of the antibodies, any of the anti-MS4A6A antibodies provided herein is useful for detecting the presence of MS4A6A in a sample or an individual. The term "detecting" as used herein encompasses quantitative or qualitative detection. Provided herein are methods of using the antibodies of this disclosure for diagnostic purposes, such as the detection of MS4A6A in an individual or in tissue samples derived from an individual. In some embodiments, the individual is a human.

The detection method may involve quantification of the antigen-bound antibody. Antibody detection in biological samples may occur with any method known in the art, including immunofluorescence microscopy, immunocytochemistry, immunohistochemistry, ELISA, FACS analysis, immunoprecipitation, or micro-positron emission tomography. In certain embodiments, the antibody is radiolabeled, for example with $^{18}F$ and subsequently detected utilizing micro-positron emission tomography analysis. Antibody-binding may also be quantified in a patient by non-invasive techniques such as positron emission tomography (PET), X-ray computed tomography, single-photon emission computed tomography (SPECT), computed tomography (CT), and computed axial tomography (CAT).

VII. Articles of Manufacture

Provided herein are articles of manufacture (e.g., kit) comprising an anti-MS4A6A antibody described herein. Article of manufacture may include one or more containers comprising an antibody described herein. Containers may be any suitable packaging including, but is not limited to, vials, bottles, jars, flexible packaging (e.g., sealed Mylar or plastic bags), and the like. The containers may be unit doses, bulk packages (e.g., multi-dose packages) or sub-unit doses.

In some embodiments, the kits may further include a second agent. In some embodiments, the second agent is a pharmaceutically-acceptable buffer or diluting agent including, but not limited to, such as bacteriostatic water for injection (BWFI), phosphate-buffered saline, Ringer's solution and dextrose solution. In some embodiments, the second agent is a pharmaceutically active agent.

In some embodiments of any of the articles of manufacture, the article of manufactures further include instructions for use in accordance with the methods of this disclosure. The instructions generally include information as to dosage, dosing schedule, and route of administration for the intended treatment. In some embodiments, these instructions comprise a description of administration of the isolated antibody of the present disclosure (e.g., an anti-MS4A6A antibody described herein) to prevent, reduce risk, or treat an individual having a disease, disorder, or injury selected from of frontotemporal dementia, Alzheimer's disease, late onset Alzheimer's disease, cognitive decline or impairment, mild cognitive impairment, vascular dementia, vascular dementia, seizures, retinal dystrophy, a traumatic brain injury, a spinal cord injury, long-term depression, atherosclerotic vascular diseases, undesirable symptoms of normal aging, dementia, mixed dementia, Creutzfeldt-Jakob disease, normal pressure hydrocephalus, amyotrophic lateral sclerosis, Huntington's disease, taupathy disease, stroke, acute trauma, chronic trauma, lupus, acute and chronic colitis, Crohn's disease, inflammatory bowel disease, ulcerative colitis, malaria, essential tremor, central nervous system lupus, Behcet's disease, Parkinson's disease, dementia with Lewy bodies, multiple system atrophy, degenerative disc disease, Shy-Drager syndrome, progressive supranuclear palsy, cortical basal ganglionic degeneration, acute disseminated encephalomyelitis, granulomatous disorders, Sarcoidosis, diseases of aging, age related macular degeneration, glaucoma, retinitis pigmentosa, retinal degeneration, respiratory tract infection, sepsis, eye infection, systemic infection, inflammatory disorders, arthritis, multiple sclerosis, metabolic disorder, obesity, insulin resistance, type 2 diabetes, tissue or vascular damage, an injury, inflammatory cell debris or protein aggregates, abnormal circulating myeloid cells, unhealthy aging, age-related cognitive impairment, age-related brain atrophy, age-associated traits, including without limitation inflammation, neuronal loss, and cognitive deficits, such as cognitive deficits in the absence of known brain disease, including cognitive deficits of the frontal cerebral cortex of an older individual and, one or more undesirable symptoms of normal aging, comprising administering to the individual a therapeutically effective amount of the anti-MS4A6A antibody of any of the preceding embodiments.

In some embodiments, the instructions include instructions for use of the anti-MS4A6A antibody and the second agent (e.g., second pharmaceutically active agent).

The present disclosure will be more fully understood by reference to the following Examples. They should not, however, be construed as limiting the scope of the present disclosure. All citations throughout the disclosure are hereby expressly incorporated by reference.

EXAMPLES

Example 1: Construction of MS4A6A Expression Plasmids for DNA Immunization

A DNA immunization approach was used for developing antibodies directed against MS4A6A. cDNA sequences encoding human and cynomolgus (cyno) MS4A6A (SEQ ID NOs:1 and 3, respectively) were cloned into the pCAGGS expression vector (KeraFAST EH1017) for DNA immunization. Expression of MS4A6A protein was confirmed via transient transfection of the expression constructs into HEK293T cells, followed by western blotting using commercially-available anti-MS4A6A antibodies (rabbit polyclonals from Abcam, Cat #156278 and Cat #189983). To do this, cells transfected for 24 hours were lysed in lysis buffer (RIPA lysis buffer (ThermoFischerScientific Cat #89900)+ 1:100 HALT protease inhibitor cocktail (ThermoFischerScientific Cat #87786)), and cleared of insoluble debris by centrifugation at 14,000×g for 15 minutes. The soluble fraction was assayed with bicinchoninic acid (BCA) reagent for protein quantification. Equal amounts of protein from each sample were loaded on a 4-12% Bis-Tris Plus polyacrylamide gel (ThermoFisher Scientific NW04120) and subjected to electrophoresis separation, after which proteins in the gel were transferred onto a polyvinylidene difluoride (PVDF) membrane using iBlot2 (ThermoFisher Scientific IM21001) and Transfer Stacks (ThermoFisher Scientific IB24002). The membrane was blocked with either 1% bovine serum albumin or 5% non-fat milk to prevent non-specific binding. The membrane was then incubated with the polyclonal anti-MS4A6A antibodies (Abcam, CAT #156278 and CAT #189983), washed, and then incubated with HRP-conjugated secondary antibody (rabbit, Abcam #205718; mouse, Abcam #205719). Binding was visualized by developing the membrane with SuperSignal West Pico Plus chemiluminescent substrate (ThermoFisher Scientific CAT #34577), and recorded digitally with iBright FL1000 (ThermoFisher A32752) or other compatible systems.

As shown in FIG. 1, cells transfected with expression constructs of either human MS4A6A or cyno MS4A6A displayed reactive bands at approximately 27 kDa as probed by polyclonal anti-MS4A6A antibodies (Top: Abcam #156278, Bottom: Abcam #189983). Untransfected HEK293 cells or HEK293 cells transfected with irrelevant MS4A4A expression construct showed very low levels of MS4A6A reactivity, possibly due to some endogenous expression.

Example 2: Generation of Anti-MS4A6A Hybridoma Antibodies

In order to obtain antibodies against MS4A6A, the following procedures were used to generate hybridomas. Balb/c or SJL mice (Jackson Laboratory, Bar Harbor, ME) were co-immunized weekly with 50 μm each of plasmid DNA encoding full-length human or cyno MS4A6A with or without mFlt3 ligand (DNA) and mGM-CSF (DNA) (Invitrogen, San Diego, CA) diluted in lactated Ringer's solution. A total of 8 injections of the MS4A6A expression plasmids for DNA immunization were performed per mouse. Spleens were harvested from the mice three days following the final DNA immunization. Sera from the mice were analyzed for reactivity to MS4A6A by FACS analyses using HEK293 cells overexpressing human and/or cyno MS4A6A. Splenocytes from mice whose sera demonstrated strong binding to HEK293 cells overexpressing human and/or cyno MS4A6A by FACS were fused with P3X63Ag8.653 mouse myeloma cells (CRL-1580, American Type Culture Collection, Rockville, MD) via electrofusion (ECM 2001, BTX, Holliston, MA) and incubated at 37° C., 5% $CO_2$, overnight in Clonacell-HY Medium C (StemCell Technologies, Vancouver, BC, Canada).

The following day, the fused cells were centrifuged and resuspended in 10mls of ClonaCell-HY Medium C with anti-mouse IgG Fc-FITC (Jackson Immunoresearch, West Grove, PA) and then gently mixed with 90mls of methylcellulose-based ClonaCell-HY Medium D (Stemcell Technologies) containing HAT components. The cells were plated into Nunc OmniTrays (Thermo Fisher Scientific, Rochester, NY) and allowed to grow at 37° C., 5% $CO_2$ for eight days. Fluorescent colonies were selected and transferred into 96-well plates containing Clonacell-HY Medium E (StemCell Technologies) using a Clonepix 2 (Molecular Devices, Sunnyvale, CA). After five days, tissue culture supernatants from the hybridomas were screened by FACS against HEK293 cells overexpressing full length cyno MS4A6A as described below. In total, 960 hybridoma clones were generated from two independent rounds of fusion.

Example 3: Transfection of HEK293 Cells with MS4A6A Gene Variants

HEK293 cells (ATCC CRL-1573) were cultured in Dulbecco's Modified Eagle's Medium (DMEM, Sigma)+10% FBS (Gibco) until >80% confluent. The cells were then dissociated with a non-enzymatic cell dissociation buffer (CellStripper, Corning) and plated at 40-50% confluency in T150 flasks (ThermoFischerScientific CAT #08-772-48) 24 hours prior to transfection. Transfection was carried out with Lipofectamine 3000 (ThermoFischerScientific), according to the manufacturer's protocol. Cells were harvested 24 hours after transfection in order to precede any toxic effects of MS4A6A over-expression in HEK293 cells. Harvested cells were either immediately used for FACS analyses or frozen in 10% DMSO for subsequent use.

Transiently-transfected HEK293 cells expressing either human or cyno MS4A6A were generated. MS4A6A protein expression in the cells was confirmed by western blotting as follows. HEK293 cells transfected for 24 hours were lysed in lysis buffer (RIPA lysis buffer (ThermoFischerScientific CAT #89900)+1:100 HALT protease inhibitor cocktail (ThermoFischerScientific CAT #87786)), and cleared of insoluble debris by centrifugation at 14,000×g for 15 minutes. The soluble fraction was assayed with bicinchoninic acid (BCA) reagent for protein quantification. Equal amounts of proteins from each sample were loaded on a 4-12% Bis-Tris Plus polyacrylamide gel (ThermoFisher Scientific NW04120) and subjected to electrophoresis separation, after which proteins in the gel were transferred onto a polyvinylidene difluoride (PVDF) membrane using iBlot2 (ThermoFisher Scientific IM21001) and Transfer Stacks (ThermoFisher Scientific IB24002). The membrane was blocked with either 1% bovine serum albumin or 5% non-fat milk to prevent non-specific binding. It was then incubated with polyclonal antibodies (Abcam, Cat #156278 and 189983), washed, and then incubated with HRP-conjugated secondary antibody (rabbit, Abcam #205718; mouse, Abcam #205719). Binding was visualized by developing with SuperSignal West Pico Plus chemiluminescent substrate (ThermoFisher Scientific #34577), and recorded digitally with iBright FL1000 (ThermoFisher Scientific #A32752) or other compatible systems.

As no commercially-available reagents are available for MS4A6A for use in flow cytometry, sera from the immunized mice were used to detect surface expression of MS4A6A on the cells. Briefly transiently-transfected cells were labeled with LIVE/DEAD Fixable Aqua Dead Cell Stain Kit (ThermoFisher Scientific L34957) on ice for 30 minutes. After a wash with PBS, $2\times10^5$ cells were aliquoted per well in 96-well U-bottom plates and incubated with 50 μl of diluted sera on ice for 30 minutes. After primary incubation, the supernatant was removed via centrifugation, the cells were washed twice with 175 μl of ice-cold FACS buffer (PBS+1% FBS+2 mM EDTA), and then incubated on ice for 20 minutes with anti-mouse IgG Fc-APC (Jackson ImmunoResearch Labs, West Grove, PA, CAT #115-136-071) diluted 1:200. Following this secondary incubation, the cells were again washed twice with ice-cold FACS buffer and resuspended in a final volume of 200 μl of FACS buffer. Analysis was performed on a FACS Canto system (BD Biosciences), with gates drawn to exclude dead (Aqua-positive) cells.

The results showed that cells transiently-transfected with cyno MS4A6A were positive for cell surface expression of MS4A6A. Cells transiently-transfected with human MS4A6A did not display cell surface expression of MS4A6A using this method, despite the detection of MS4A6A protein in these cells using western blot analysis (See FIG. 1). FIGS. 2A and 2C show the results of two independent hybridoma supernatants on binding to HEK293 cells transfected with human MS4A6A (clear trace) and to non-transfected HEK293 cells (shaded trace), respectively. FIGS. 2B and 2D show the results of two independent hybridoma supernatants on binding to HEK293 cells transfected with cyno MS4A6A (clear trace) and to non-transfected HEK293 cells (shaded trace), respectively. As shown in FIGS. 2B and 2D, cells transfected with cyno-MS4A6A displayed strong anti-MS4A6A antibody binding.

As cyno MS4A6A amino acid sequence is approximately 89% identical to human MS4A6A amino acid sequence, most clones would thus be expected to be cross-reactive between human and cyno MS4A6A. This was confirmed with peptide binding studies described below. Accordingly, subsequent screening of the hybridoma supernatants was performed using cells transfected with cyno MS4A6A.

Example 4: Transfection of Other Cell Lines with MS4A6A Expression Plasmids

Given the difficulty for generating stably-transfected HEK293 cell lines expressing human MS4A6A or cyno MS4A6A, other DNA vectors and cell lines were tested to determine if they would be more compatible for MS4A6A expression. For stable transfection, MS4A6A coding sequence was introduced into expression vectors pD2533-G418 or pD3539-puro (Atum, Newark, CA, USA).

MS4A6A is expressed natively in myeloid cells in vivo. Therefore, to overcome the observed toxicity issues using cells described above, several myeloid-derived cell lines were used for transient expression of recombinant MS4A6A. The panel of cell lines included THP-1 cells (ATCC TIB202), U937 cells (ATCC CRL-1593.2), K562 cells (ATCC CCL243), HL60 cells (ATCC CCL240), and Kasumi-1 cells (ATCC CRL-2724). 300.19 cells (Tufts University T000710), a mouse pre-B cell line, were also tested as they are commonly used for recombinant protein expression purposes. Each of these cell lines was screened for antibiotic susceptibility in order to determine a suitable dose of G418 or puromycin for selection and transfection efficiency. Transfectants from U937 cells, K562 cells, and 300.19 cells were found to be viable after MS4A6A expression plasmid transfection and antibiotic-selection. After cloning by limiting-dilution, individual clones were generated and screened for human MS4A6A protein expression by western blotting as described above.

Figure 3A:
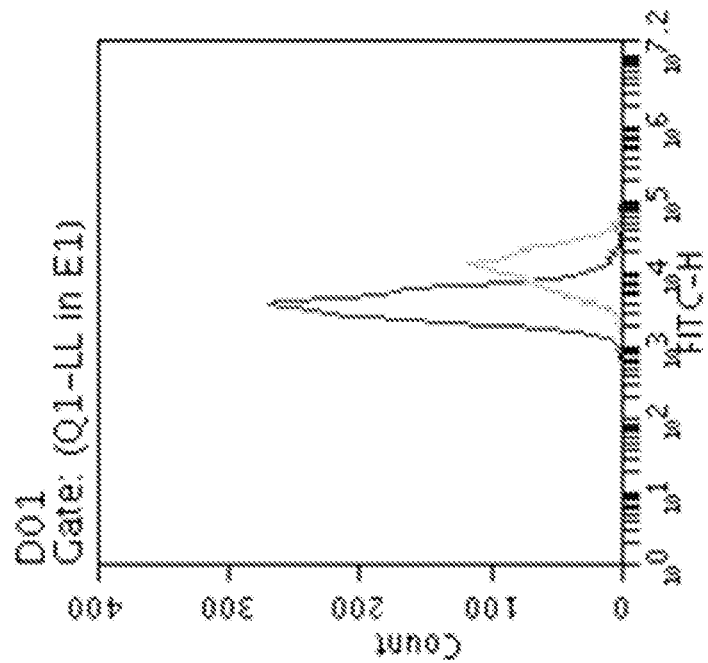
FIGS. 3A and 3B show cell surface expression of cyno MS4A6A in U937 cells (right trace in FIG. 3A) or K562 cells (right trace in FIG. 3B) transfected with cyno MS4A6A compared to non-transfected U937 cells (left trace in FIG. 3A) and non-transfected K562 cells (left trace in FIG. 3B) using hybridoma supernatant containing anti-MS4A6A of the present disclosure.
Figure 3B:
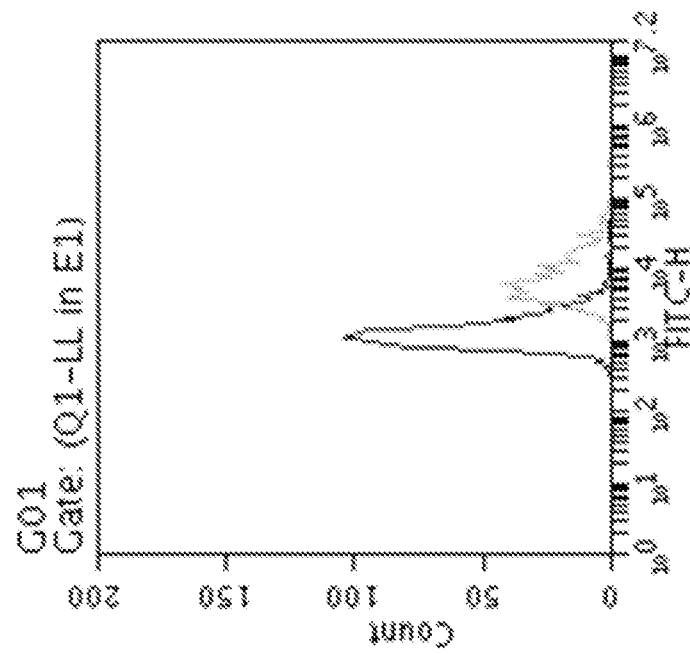

Additionally, cyno MS4A6A expression constructs were generated and transfected into the cell lines described above. As cyno MS4A6A protein can be detected on the cell surface by flow cytometry, this method was used to confirm surface expression of MS4A6A in stable U937 cell and K562 cell transfectants. The results are shown in FIG. 3A (U937 cells) and FIG. 3B (K562 cells). FIG. 3A shows binding to cyno MS4A6A-transfected U937 cells (right trace) compared to binding to non-transfected U937 cells (left trace). FIG. 3B shows binding to cyno MS4A6A-transfected K562 cells (right trace) compared to binding to non-transfected K562 cells (left trace). These results showed that the anti-MS4A6A hybridoma supernatants are able to bind cell-surface expressed cyno MS4A6A in transfected cells.

Example 5: Primary Screening of Anti-MS4A6A Hybridomas

Initial screening of the anti-MS4A6A hybridomas was performed as follows. Tissue culture supernatants from 960 hybridomas obtained were initially screened for their ability to differentially bind cyno MS4A6A-transfected HEK293 cells by comparing the extent of binding to parental (non-transfected) HEK293 cells compared to transfected cells. MS4A6A-expressing cells were produced via transient transfection of HEK293 cells using the lipofectamine system, according to the manufacturer's protocol with modifications as described above. To ensure reproducibility across screening experiments, a large bank of transfected cells (~1×10$^9$) was prepared in a single round of transient transfection, and aliquoted and frozen for all further screening experiments.

For screening of hybridoma cell culture supernatants, cyno MS4A6A-transfected HEK293 cells were aliquoted in 96-well U-bottom plates (2×10$^5$ cells per well) and incubated with 50 µL of hybridoma cell culture supernatant on ice for 30 minutes. After this primary incubation, the supernatant was removed via centrifugation, the cells were washed twice with 175 µL of ice-cold FACS buffer (PBS+ 1% FBS+2 mM EDTA), and then further incubated on ice for 20 minutes with anti-mouse IgG Fc-allophycocyanin (APC) (Jackson Labs, CAT #115-136-071) (diluted 1:200). Following this secondary incubation, the cells were again washed twice with ice-cold FACS buffer and resuspended in a final volume of 30 µL of FACS buffer+0.25 µl well propidium iodide (BD Biosciences CAT #556463). Binding intensity on cells were analyzed by the FACS Canto system (BD Biosciences), with sort gates drawn to exclude dead cells, as judged by lack of propidium iodide exclusion. Ratio of APC mean fluorescence intensity (MFI) on MS4A6A-transfectants vs. HEK293 parental cells was calculated for each hybridoma supernatant. A total of 55 clones were identified that displayed greater than 1.5-fold difference in binding to MS4A6A-transiently transfected HEK293 cells compared to binding to parental (non-transfected) HEK293 cells.

Positive clones were expanded and then rescreened for specificity against HEK293 cells overexpressing cyno MS4A6A and parental HEK293 cells. Briefly, previously prepared, cryopreserved transiently-transfected cells were labeled with LIVE/DEAD Fixable Aqua Dead Cell Stain Kit (ThermoFisher Scientific L34957) on ice for 30 minutes. After a wash with PBS, 2×10$^5$ cells were aliquoted per well in 96-well round bottom plates and incubated with 50 µl of culture supernatant on ice for 30 mins. After primary incubation, the supernatant was removed via centrifugation, the cells were washed twice with 175 µl of ice-cold FACS buffer (PBS+1% FBS+2 mM EDTA) and then incubated with anti-mouse IgG Fc-APC (Jackson ImmunoResearch Labs, West Grove, PA, CAT #115-136-071) diluted 1:200 on ice for 20 mins. Following this secondary incubation, the cells were again washed twice with ice-cold FACS buffer and resuspended in a final volume of 200 µl of FACS buffer. Analysis was performed on a FACS Canto system (BD Biosciences), with sort gates drawn to exclude dead (Aqua-positive) cells. Ratio of APC MFI on MS4A6A+/HEK parental cells was calculated for each hybridoma; these results are shown below in Table 2. The screen was repeated twice, and the numbers reported here represent the ratio of mean fluorescence level in transfected cells over parental cells.

TABLE 2

| Clone | Screen 1 | Screen 2 | Mouse strain |
| --- | --- | --- | --- |
| 6A-1 | 7.5 | 7.6 | Balb/c |
| 6A-2 | 25.7 | 75.5 | Balb/c |
| 6A-3 | 24.1 | 63.7 | Balb/c |
| 6A-4 | 5.4 | 16.2 | Balb/c |

TABLE 2-continued

| Clone | Screen 1 | Screen 2 | Mouse strain |
|---|---|---|---|
| 6A-5 | 24.3 | 188.7 | Balb/c |
| 6A-6 | 13.5 | 62.1 | Balb/c |
| 6A-7 | 3.6 | 8.3 | Balb/c |
| 6A-8 | 26.7 | 69.5 | Balb/c |
| 6A-9 | 12.6 | 84.0 | Balb/c |
| 6A-10 | 18.0 | 95.2 | Balb/c |
| 6A-11 | 8.6 | 61.7 | Balb/c |
| 6A-12 | 40.3 | 45.5 | Balb/c |
| 6A-13 | 24.8 | 30.3 | Balb/c |
| 6A-14 | 20.2 | 59.1 | Balb/c |
| 6A-15 | 3.8 | 8.4 | Balb/c |
| 6A-16 | 14.4 | 28.5 | Balb/c |
| 6A-17 | 19.3 | 178.4 | Balb/c |
| 6A-18 | 4.1 | 20.3 | Balb/c |
| 6A-19 | 2.8 | 35.8 | Balb/c |
| 6A-20 | 2.7 | 0.2 | SJL |
| 6A-21 | 71.8 | 136.0 | Balb/c |
| 6A-22 | 175.3 | 68.8 | Balb/c |
| 6A-23 | 155.5 | 82.0 | Balb/c |

Example 6: Anti-MS4A6A Antibody ELISA Screen

Anti-MS4A6A hybridoma supernatants were tested for binding to MS4A6A peptides derived from ECL1 (amino acid residues 68-85 of human MS4A6A of SEQ ID NO:1) and ECL2 (amino acid residues 138-185 of human MS4A6A of SEQ ID NO:1) sequences, using an enzyme-linked immunosorbent assay (ELISA). Briefly, 96-well polystyrene plates were coated with 1-10 µg/mL of synthetic free or BSA-conjugated peptides in coating buffer (0.05M carbonate buffer, pH9.6, Millipore Sigma C3041) overnight at 4° C. Coated plates were then blocked with ELISA diluent (PBS+ 0.5% BSA+0.05% Tween20) for 1-hour, washed 3×300 µL in PBST (PBS+0.05% Tween20, Thermo 28352), and then the antibodies were added at various dilutions (100-1000×) in ELISA diluent. After 30 mins incubation (room temperature, with shaking), the plates were washed 3×300 µl in PBST. A secondary anti-mouse HRP antibody (Jackson Immunoresearch CAT #115-035-003) was added at a 1:1000 dilution in ELISA diluent (50 µL/well) and incubated for 30 minutes at room temperature with shaking. After a final set of washes (3×300 µl in PBST), 50 µL of TMB substrate (BioFx TMBW-1000-01) was added and the reaction was then quenched after 5-10 mins with 50 µL of stop solution (BioFx BSTP-1000-01). The quenched reaction wells were detected for absorbance at 650 nm with a BioTek Synergy Microplate Reader using GENS 2.04 software.

Of the 23 anti-MS4A6A positive hybridoma clones identified, supernatants from 17 hybridoma clones displayed strong binding to the BSA-MS4A6A-ELC2 peptide compared to BSA-mouse DAP12, an irrelevant control peptide. Even though these clones were initially selected by their ability to bind to cell surface expressed cyno MS4A6A protein, many of the clones still display binding to the human M4A6A ECL2 peptide, indicating some cross-reactivity of these clones between these two closely-related MS4A6A sequences. The hybridoma clones displaying no binding may be accounted by several factors, e.g., these antibodies may bind to conformational epitopes that were not modeled by this methodology, these antibodies may recognize epitopes that are made up of both ECL1 and ECL2, or these antibodies may not cross-react to human MS4A6A protein.

Binding to ECL1, on the other hand, was not detected for any of the hybridoma clones screened. This is likely due to the smaller size of ECL1, which is 18 amino acid residues in length compared to that of ECL2, which is 48 amino acid residues in length. If MS4A6A forms a barreled structure similar to that of CD81, a molecule that similarly spans the cell membrane four times, then the larger ECL2 domain may dominate the exposed surface available for antibody binding. It is possible that certain antibodies identified herein recognize epitopes formed by a combination of amino acid residues located in ECL1 and ECL2, and thus would not detected by this methodology. It is noted that the amino acids of ECL1 of human MS4A6A and cyno MS4A6A are identical.

The results of the ELISA binding experiments are shown below in Table 3.

TABLE 3

| Clones showing strong binding to MS4A6A-ECL2 BSA conjugated peptide | Clones with no binding detected |
|---|---|
| 6A-2, 6A-3, 6A-6, 6A-8, 6A-9, 6A-10, 6A-11, 6A-12, 6A-13, 6A-14, 6A-15, 6A-16, 6A-18, 6A-19, 6A-21, 6A-22, 6A-23 | 6A-1, 6A-4, 6A-5, 6A-7, 6A-17, 6A-20 |

Example 7: Molecular Cloning of Anti-MS4A6A Hybridoma Antibodies

Anti-MS4A6A antibodies obtained from the hybridomas described above were cloned as follows. $5 \times 10^5$ hybridoma cells were resuspended in 0.5ml Trizol solution (Thermo Fisher Scientific, CAT #15596026). Total RNA was extracted from the cells by chloroform extraction and ethanol precipitation. cDNA was generated by using Clontech's SMARTer® RACE 5'/3' Kit (Takara Bio USA Inc, Cat. No. 634859) following the manufacture's protocol. Variable heavy and light immunoglobulin regions were cloned separately by touchdown PCR using the 5' UPM primer provided in the RACE kit and heavy chain constant region primer (5'-AGCTGGGAAGGTGTGCACA-3') (SEQ ID NO:129) and light constant region primer (5'-CCATTTTGTCGTT-CACTGCCA-3') (SEQ ID NO:130). PCR products were purified by QIAquick PCR Purification Kit (QIAGEN, Cat No. 28106) and ligated into a pCR2.1®-TOPO® cloning vector (TOPO® TA cloning Kit, Invitrogen) and transformed into ONESHOT® TOP10 Competent cells. Transformed *Escherichia coli* (*E. coli*) colonies were isolated and the variable heavy chain (VH) and variable light chain (VL) nucleic acids were sequenced for each corresponding hybridoma cell line. Following the sequence determination, variable heavy chain regions and variable light chain regions were amplified by PCR using primers containing endonuclease restriction sites (BsrGI and BstEII for HV and BssHII and BsiWI for LV) and subcloned into pJG mammalian expression vector (Alector Inc.) encoding human IgG1 and IgGK, respectively.

Example 8: Production of Recombinant Anti-MS4A6A Antibodies

Purified hybridoma-derived anti-MS4A6A antibodies were purified using Protein A from hybridoma supernatants after culturing the hybridomas in low-IgG or chemically defined media. Some of the anti-MS4A6A antibodies were also produced via direct cloning of the variable gene regions obtained from the hybridomas into a recombinant expression plasmid for production of chimeric antibodies containing a human Fc domain (human IgG1). The expression plasmids were transiently transfected into Expi293 cells and the resulting anti-MS4A6A antibodies purified via Protein A.

Recombinant production of anti-MS4A6A antibodies was performed as follows. Expression plasmids containing nucleic acid encoding the anti-MS4A6A antibody VH and VL chains used for recombinant antibody expression in Expi293 cells. Transfection of expression plasmids was carried out using the Expifectamine-293 system (ThermoFischerScientific CAT #A14524) according to the manufacturer's protocol. Briefly, for each anti-MS4A6A antibody, 12 µg of light chain plasmid DNA and 18 µg of heavy chain plasmid DNA was diluted into 1.5 mL OptiMEM (ThermoFischerScientific CAT #31985070), to which was added 80 µL of Expifectamine reagent. The resulting solution was mixed and incubated at room temperature for 30 minutes prior to addition to 30 mL of Expi293 cells (ThemoFischerScientific A14527) in Expi293 expression media (ThermoFischerScientific CAT #A1435101) in 125 mL flasks (Fischer Scientific FIS #PBV12-5). The cells were cultured to approximately $3 \times 10^{\wedge}6$ cells/mL prior to transfection. Culture conditions for Expi293 cells were 37° C./8% CO2 with orbital shaking at 125 rpm. 16-24 hours after transfection, 150 µL of ExpiFectamine™293 Transfection Enhancer 1 and 1.5 mL of ExpiFectamine™293 Transfection Enhancer 2 were added to each flask to enhance recombinant antibody yield. Culture supernatants were harvested 5-7 days after transfection, filtered (0.2 micron), and purified via Protein A chromatography.

Example 9: Antibody Heavy Chain and Light Chain Variable Domain Sequences

Using standard techniques, the amino acid sequences encoding the light chain variable regions and the heavy chain variable regions of the generated antibodies were determined for 22 of the 23 antibodies identified. The Kabat light chain CDR sequences and heavy chain CDR sequences of the antibodies are set forth in Table 4A below. The light chain variable region and heavy chain variable region sequences of the antibodies are set forth in Table 4B below.

TABLE 4A

Antibody CDR sequences

| Clone ID | CDR-H1 | CDR-H2 | CDR-H3 | CDR-L1 | CDR-L2 | CDR-L3 |
|---|---|---|---|---|---|---|
| 6A-1 | GYYMH (SEQ ID NO: 4) | AINPSTGGSTY SEQ ID (SEQ ID NO: 17) | FDGYGY (SEQ ID NO: 32) | RSSKSLLHSNGI TYLY (SEQ ID NO: 46) | QMSNLAS (SEQ ID NO: 61) | AQNLELPWT (SEQ ID NO: 77) |
| 6A-2 | SGYYW N (SEQ ID NO: 5) | YITYDGDTDY NPSLKN (SEQ ID NO: 18) | EDSFGY (SEQ ID NO: 33) | RASESVDNYG VSFMN (SEQ ID NO: 47) | AASNQGS (SEQ ID NO: 62) | QQSKEVPWT (SEQ ID NO: 78) |
| 6A-3 | DYFMK (SEQID NO: 6) | DINPKNGDTF YNQKFKG (SEQ ID NO: 19) | PGYFDV (SEQ ID NO: 34) | KSSQSLLDSDG KTYLS (SEQ ID NO: 48) | LMSKLDS (SEQ ID NO: 63) | WQGTHFPQT (SEQ ID NO: 79) |
| 6A-4 | GYYMH (SEQID NO: 4) | AINPSTGGSTY SQKFKD (SEQ ID NO: 17) | FDGYGY (SEQ ID NO: 32) | RSSKSLLHSNGI TYLY (SEQ ID NO: 46) | QMSNLAS (SEQ ID NO: 61) | AQNLELPWT (SEQ ID NO: 77) |
| 6A-5 | SYWIN (SEQID NO: 7) | DIYPGSGSTNY DEKFKS (SEQ ID NO: 20) | SRYDGYYAAY (SEQ ID NO: 35) | RASDHIHNWL A (SEQ ID NO: 49) | GATSLET (SEQ ID NO: 64) | QHYWSIPWT (SEQ ID NO: 80) |
| 6A-6 | NYGMN (SEQ ID NO: 8) | YINIYSGKSRY ADDFKG (SEQ ID NO: 21) | DNDYFDY (SEQ ID NO: 36) | RASQSISDNLH (SEQ ID NO: 50) | YASQSIS (SEQ ID NO: 65) | QQSNSWPYT (SEQ ID NO: 81) |
| 6A-7 | SYAMH (SEQ ID NO: 9) | YINPSSGYTYY NQKFKD (SEQ ID NO: 22) | SYYGNYEGYL DV (SEQ ID NO: 37) | RASESVESYGK SFIH (SEQ ID NO: 51) | LASNLES (SEQ ID NO: 66) | QQNNVGPYT (SEQ ID NO: 82) |
| 6A-8 | DYYIN (SEQ ID NO: 10) | EIYPRSGNAYY NEKFRG (SEQ ID NO: 23) | GDGNWYFDV (SEQ ID NO: 38) | KSSQSLLNSGD QENYLV (SEQ ID NO: 52) | GASTRES (SEQ ID NO: 67) | QSDHSYPLT (SEQ ID NO: 83) |
| 6A-9 | GYYIH (SEQ ID NO: 11) | RINPKNGVTSY NQNFKD (SEQ ID NO: 24) | TFITG (SEQ ID NO: 39) | RSSQTIVHSDG NTYLE (SEQ ID NO: 53) | TVSNRFS (SEQ ID NO: 68) | FQGSHVPWT (SEQ ID NO: 84) |
| 6A-10 | NYGMN (SEQ ID NO: 8) | WINTYTGEPT YADDFKG (SEQ ID NO: 25) | AYGNSAWFA Y (SEQ ID NO: 40) | RASSSVSYMH (SEQ ID NO: 54) | ATSNLAS (SEQ ID NO: 69) | QQWSSNPWT (SEQ ID NO: 85) |
| 6A-11 | GYYIH (SEQ ID NO: 11) | RINPNNGATN YNQIFKD (SEQ ID NO: 26) | TFITG (SEQ ID NO: 39) | RSSQTIVHSDG NTYLE (SEQ ID NO: 53) | KVSIRFS (SEQ ID NO: 70) | FQGSHVPWT (SEQ ID NO: 84) |

TABLE 4A-continued

Antibody CDR sequences

| Clone ID | CDR-H1 | CDR-H2 | CDR-H3 | CDR-L1 | CDR-L2 | CDR-L3 |
|---|---|---|---|---|---|---|
| 6A-12 | GYYMH (SEQ ID NO: 4) | AINPSTGGSTY SQKFKD (SEQ ID NO: 17) | FDGYGY (SEQ ID NO: 32) | RSSKSLLHSNGI TYLY (SEQ ID NO: 46) | QMSNLAS (SEQ ID NO: 61) | AQNLELPWT (SEQ ID NO: 77) |
| 6A-13 | DYYMT (SEQ ID NO: 12) | FIRNKANGYT TEYNSSVKG (SEQ ID NO: 27) | SMDY (SEQ ID NO: 41) | KASENVGTYV S (SEQ ID NO: 55) | GASNRYT (SEQ ID NO: 71) | GQTYSFPYT (SEQ ID NO: 86) |
| 6A-14 | TYGVH (SEQ ID NO: 13) | VIWSGGSTDY NAAFIS (SEQ ID NO: 28) | GYGSSYEYFD V (SEQ ID NO: 42) | RASESVDSYGN SFMH (SEQ ID NO: 56) | RASNLES (SEQ ID NO: 72) | QQSNEDPLT (SEQ ID NO: 87) |
| 6A-15 | SHAMS (SEQ ID NO: 14) | TISSGDSYTYY PDSVKG (SEQ ID NO: 29) | HIYYGNLYYA MDY (SEQ ID NO: 43) | RSSQSIIHNNGN TYLE (SEQ ID NO: 57) | KVSNRFS (SEQ ID NO: 73) | FQGSHVPWT (SEQ ID NO: 84) |
| 6A-16 | GYYIH (SEQ ID NO: 11) | RINPKNGVTSY NQNFKD (SEQ ID NO: 24) | TFITG (SEQ ID NO: 39) | RSSQTIVHSDG NTYLE (SEQ ID NO: 53) | TVSNRFS (SEQ ID NO: 68) | FQGSHVPWT (SEQ ID NO: 84) |
| 6A-17 | SYGVH (SEQ ID NO: 15) | VIWSDGSTTY NSALKS (SEQ ID NO: 30) | HRGNYPYYT MDY (SEQ ID NO: 44) | RASQDISNYLN (SEQ ID NO: 58) | YTSVLHS (SEQ ID NO: 74) | QQGNTLPWT (SEQ ID NO: 88) |
| 6A-18 | GYYIH (SEQ ID NO: 11) | RINPKNGVTSY NQNFKD (SEQ ID NO: 24) | TFITG (SEQ ID NO: 39) | RSSQTIVHSDG NTYLE (SEQ ID NO: 53) | TVSNRFS (SEQ ID NO: 68) | FQGSHVPWT (SEQ ID NO: 84) |
| 6A-20 | DYFMK (SEQ ID NO: 6) | DINPKNGDTF YNQKFKG (SEQ ID NO: 19) | PGYFDV (SEQ ID NO: 34) | RSSKSLLHSDG NTYLY (SEQ ID NO: 59) | RMSNLAP (SEQ ID NO: 75) | MQHLEFPFI (SEQ ID NO: 89) |
| 6A-21 | DYFMK (SEQ ID NO: 6) | DINPKNGDTF YNQKFKG (SEQ ID NO: 19) | PGYFDV (SEQ ID NO: 34) | KSSQSLLDSDG KTYLS (SEQ ID NO: 48) | LMSKLDS (SEQ ID NO: 63) | WQGTHFPQT (SEQ ID NO: 79) |
| 6A-22 | DAWMD (SEQ ID NO: 16) | EIKNKANNYV TFYAASVKG (SEQID NO: 31) | GSVYGNWFPY RKNYLT (SEQ ID NO: 45) | KSSQSLFNSRT (SEQ ID NO: 60) | WASTRES (SEQ ID NO: 76) | KQSYNLLT (SEQ ID NO: 90) |
| 6A-23 | DAWMD (SEQ ID NO: 16) | EIKNKANNYV TFYAASVKG (SEQ ID NO: 31) | GSVYGNWFPY RKNYLT (SEQ ID NO: 45) | KSSQSLFNSRT (SEQ ID NO: 60) | WASTRES (SEQ ID NO: 76) | KQSYNLLT (SEQ ID NO: 90) |

TABLE 4B $V_H$ and $V_L$ sequences

| Clone ID | $V_H$: | $V_L$: |
|---|---|---|
| 6A-1 | EVQLQQSGPELVKPGASVKISCKASGYSFTGYYMHW VKQSPEDSLEWIGAINPSTGGSTYSQKFKDKATLTVD KSSSTAYMQLKSLTSEESAVYYCTRFDGYGYWGQG TLVTVSA (SEQ ID NO: 91) | DIVMTQAAFSNPVTLGTSASISCRSSKSLLHS NGITYLYWLQKPGQSLQLLIYQMSNLASG VPDRFSGSGSGTDFTLRISRVEAEDVGVYYC AQNLELPWTFGGGTKLEIK (SEQ ID NO: 109) |
| 6A-2 | DVQLQESGPGLVKPSQSLSLTCSVTGYSITSGYYWN WIRQFPGNKLEWLGYITYDGDTDYNPSLKNRVSITR DTSKNQFFLNLISVTPEDTATYYCAREDSFGYWGQG TLVTVSA (SEQ ID NO: 92) | DIVLTQSPASLTVSLGQRATISCRASESVDNY GVSFMNWFQQKPGQPPKLLIYAASNQGSGV PARFSGSGSGTDFSLNIHPMEEEDTAMYFCQ QSKEVPWTFGGGTKLEIK (SEQ ID NO: 110) |
| 6A-3 | EVQLQQSGPELVKPGASVKMSCKASGYTFTDYFMK WVKQSHGKSLEWIGDINPKNGDTFYNQKFKGKATLT VDKSSSTAYMQLNSLTSEDSAVYYCARPGYFDVWG AGTTVTVSS (SEQ ID NO: 93) | DVVMTQAPLILSITIGQPASISCKSSQSLLDSD GKTYLSWLLQRPGQSPKRLIYLMSKLDSGVP DRFTGSGSGTDFTLKISRVEAEDLGVYYCW QGTHFPQTFGGGTKLEIK (SEQ ID NO: 111) |

TABLE 4B-continued

V_H and V_L sequences

| Clone ID | V_H: | V_L: |
|---|---|---|
| 6A-4 | EVQLQQSGPELVKPGASVKISCKASGYSFTGYYMHW VKQSPEDSLEWIGAINPSTGGSTYSQKFKDKATLTVD KSSSTAYMQLKSLTSEESAVYYCTRFDGYGYWGQG TLVTVSA (SEQ ID NO: 91) | DIVMTQAAFSNPVTLGTSASISCRSSKSLLHS NGITYLYWYLQKPGQSLQLLIYQMSNLASG VPDRFSGSGSGTDFTLRISRVEAEDVGVYYC AQNLELPWTFGGGTKLEIK (SEQ ID NO: 109) |
| 6A-5 | EVQLQQSGPELVKPGASVKISCKASGYSFTGYYMHW VKQSPEDSLEWIGAINPSTGGSTYSQKFKDKATLTVD KSSSTAYMQLKSLTSEESAVYYCTRFDGYGYWGQG TLVTVSA (SEQ ID NO: 94) | DIQMTQSSSYLSVSLGGRVTITCRASDHIHN WLAWYQQKPGDAPRLLISGATSLETGVPSRF SGSGSGKDYTLSITSLQTEDVATYYCQHYWS IPWTFGGGTKLEIK (SEQ ID NO: 112) |
| 6A-6 | QIQLVQSGPELKKPGESVKISCKASGYTFANYGMNW VKLAPGKGLKWMGYINIYSGKSRYADDFKGRFAFSL ETSASTAYLQINNLKNEDMATYFCARDNDYFDYWG QGTTLTVSS (SEQ ID NO: 95) | DIVLTQSPATLSVTPGDTVSLSCRASQSISDN LHWYQQKSHESPGLLIKYASQSISGIPSRFSG RGSGTDFTLSINSVDSEDFGVYFCQQSNSWP YTFGGGTKLEIK (SEQ ID NO: 113) |
| 6A-7 | QVQLQQSGAELARPGASVKMSCKASGYTFTSYAMH WVKQRPGQGLEWIGYINPSSGYTYYNQKFKDKATLT ADKSSSTAYMQLSSLTSEDSAVYYCARSYYGNYEGY LD VWGAGTT VT VS S (SEQ ID NO: 96) | NIVLTQSPASLAVSLGQRATISCRASESVESY GKSFIHWYQQKPGQPPKLLIFLASNLESGVP ARFSGSGSRTDFTLTIDPVEADDAATYYCQQ NNVGPYTFGGGTKLEIK (SEQ ID NO: 114) |
| 6A-8 | QVQLQQSGAELARPGTSVKLSCKASGYTFTDYYINW VKQRNGQGLEWIGEIYPRSGNAYYNEKFRGKATLTT DKSSSTAYMQLSGLTSEDSAVYFCARGDGNWYFDV WGAGTTVIVSS (SEQ ID NO: 97) | DIVMTQSPSSLSVSAGEKVTMSCKSSQSLLN SGDQENYLVWYQQKPGQPPKLLIYGASTRE SGVPDRFTGSGSGTDFTLTISSVLAEDLAVY YCQSDHSYPLTFGAGTKLELK (SEQ ID NO: 115) |
| 6A-9 | EVQLQQSGPELVKPGASVKISCKASGYSFTGYYIHW VKESHVKSLEWIGRINPKNGVTSYNQNFKDKASLTV DRSSSTAYMDLYSLTSEDSAVYYCASTFITGWGQGT SLTVSS (SEQ ID NO: 98) | DVLLTQAPLSLPVSLGDQASISCRSSQTIVHS DGNTYLEWYLQKPGQSPKLLIYTVSNRFSGV PDRFSGSGSGTDFTLKISRVEAEDLGVYYCF QGSHVPWTFGGGTKLEIK (SEQ ID NO: 116) |
| 6A-10 | QIQLVQSGPELKKPGETVKISCKASGYTFTNYGMNW VKQAPGKGLKWMGWINTYTGEPTYADDFKGRFAFS LETSASTAYLQINNLKNEDMATYFCARAYGNSAWFA YWGQGTLVTVSA (SEQ ID NO: 99) | QIVLSQSPAILSASPGEKVTMTCRASSSVSYM HWYQQKPGSSPKPWIYATSNLASGVPARFS GSGSGTSYSLTISRVEAEDAATYYCQQWSSN PWTFGGGTKLEIK (SEQ ID NO: 117) |
| 6A-11 | EVQLQQSGPDLVKPGASVKISCKASGYSFTGYYIHW VKQSHIKSLEWIGRINPNNGATNYNQIFKDKATLTVD RSSSTAYMDLHSLTSEDSAVYYCVSTFITGWGQGTTL TVSS (SEQ ID NO: 100) | DVLLTQTPLSLPVSLGDQASISCRSSQTIVHS DGNTYLEWYLQRPGLSPKLLIYKVSIRFSGV PDRFSGSGSGTDFTLKISRVEAEDLGVYYCF QGSHVPWTFGGGTKLEIK (SEQ ID NO: 118) |
| 6A-12 | EVQLQQSGPELVKPGASVKISCKASGYSFTGYYMHW VKQSPEDSLEWIGAINPSTGGSTYSQKFKDKATLTVD KSSSTAYMQLKSLTSEESAVYYCTRFDGYGYWGQG TLVTVSS (SEQ ID NO: 101) | DIVMTQAAFSNPVTLGTSASISCRSSKSLLHS NGITYLYWYLQKPGQSLQLLIYQMSNLASG VPDRFSGSGSGTDFTLRISRVEAEDVGVYYC AQNLELPWTFGGGTKLEIK (SEQ ID NO: 109) |
| 6A-13 | EVVVESGGGLVQPGGSLRLSCATAGFIH IDYYMT WVRQPPGKALEWLGFIRNKANGYTTEYNSSVKGRFT ISRDNSRSILYLQMNTLRAEDSATYYCARSMDYWGQ GTSVTVSS (SEQ ID NO: 102) | NIVMTQSPNSMSMSVGERVTLSCKASENVG TYVSWYQQKPDQSPKLLIYGASNRYTGVPD RFTGGGSATDFTLTISSVQAEDLADYHCGQT YSFPYTFGGGTKLEIK (SEQ ID NO: 119) |
| 6A-14 | QVQLKQSGPGLVQPSQSLSITCTVSGFSLTTYGVHWV RQSPGKGLEWLGVIWSGGSTDYNAAFISRLNISKDNS KSQVFFKMNSLQANDTAIYYCARGYGSSYEYFDVW GAGTTVTVSS (SEQ ID NO: 103) | DIVLTQSPASLAVSLGQRATISCRASESVDSY GNSFMHWYQQKPGQPPKLLIYRASNLESGIP ARFSGSGSRTDFTLTINPVEADDVATYYCQQ SNEDPLTFGAGTKLELK (SEQ ID NO: 120) |
| 6A-15 | EVMLVESGGGLVKPGGSLKLSCAASGFTFSSHAMSW VRQTPEKRLEWVAPISSGDSYTYYPDSVKGRFTISRD NAKNTLYLQMTSLRSEDTAMYYCIRHIYYGNLYYA MDYWGQGTSVTVSS (SEQ ID NO: 104) | DVLMTQTPLSLPVSLGDQASISCRSSQSIIHN NGNTYLEWYLQKPGQSPKLLIYKVSNRFSG VPDRFSGSGSGTYFTLKISRVEADDLGVYYC FQGSHVPWTFGGGTKLEIK (SEQ ID NO: 121) |

TABLE 4B-continued

V_H and V_L sequences

| Clone ID | V_H: | V_L: |
|---|---|---|
| 6A-16 | EVQLQQSGPELVKPGASVKISCKASGYSFTGYYIHW VKESHVKSLEWIGRINPKNGVTSYNQNFKDKASLTV DRSSSTAYMDLYSLTSEDSAVYYCASTFITGWGQGT TVTVSS (SEQ ID NO: 105) | DVLLTQAPLSLPVSLGDQASISCRSSQTIVHS DGNTYLEWYLQKPGQSPKLLIYTVSNRFSGV PDRFSGSGSGTDFTLKISRVEAEDLGVYYCF QGSHVPWTFGGGTKLEIK (SEQ ID NO: 116) |
| 6A-17 | QVQLKESGPGLVAPSQSLSITCTISGFSLTSYGVHWV RQPPGKGLEWLVVIWSDGSTTYNSALKSRLSISKDNS KSQVFLKMNGLQTDDTAMYYCARHRGNYPYYTMD YWGQGTSVTVSS (SEQ ID NO: 106) | DIQMTQTTSSLSASLGDRVTISCRASQDISNY LNWYQQKPDGTVKLLIYYTSVLHSGVPSRFS GSGSGTDYSLTISNLEQEDIATYFCQQGNTLP WTFGGGTKLEIK (SEQ ID NO: 122) |
| 6A-18 | EVQLQQSGPELVKPGASVKISCKASGYSFTGYYIHW VKESHVKSLEWIGRINPKNGVTSYNQNFKDKASLTV DRSSSTAYMDLYSLTSEDSAVYYCASTFITGWGQGT SLTVSS (SEQ ID NO: 98) | DVLLTQAPLSLPVSLGDQASISCRSSQTIVHS DGNTYLEWYLQKPGQSPKLLIYTVSNRFSGV PDRFSGSGSGTDFTLKISRVEAEDLGVYYCF QGSHVPWTFGGGTKLEIK (SEQ ID NO: 116) |
| 6A-20 | EVQLQQSGPELVKPGASVKMSCKASGYTFTDYFMK WVKQSHGKSLEWIGDINPKNGDTFYNQKFKGKATLT VDKSSSTAYMQLNSLTSEDSAVYYCARPGYFDVWG AGTTVTVSS (SEQ ID NO: 93) | DIVMTQAAPSVPVTPGESVSISCRSSKSLLHS DGNTYLYWFLQRPGQSPQLLIYRMSNLAPG VPDRFSGSGSGTAFTLRISRVEAEDVGVYYC MQHLEFPPFIFGAGTKLELK (SEQ ID NO: 123) |
| 6A-21 | EVQLQQSGPELVKPGASVKMSCKASGYTFTDYFMK WVKQSHGKSLEWIGDINPKNGDTFYNQKFKGKATLT VDKSSSTAYMQLNSLTSEDSAVYYCARPGYFDVWG AGTTVTVSS (SEQ ID NO: 93) | DVVMTQAPLILSITIGQPASISCKSSQSLLDSD GKTYLSWLLQRPGRSPKRLIYLMSKLDSGVP DRFTGSGSGTDFTLKISRVEAEDLGVYYCW QGTHFPQTFGGGTKLEIK (SEQ ID NO: 124) |
| 6A-22 | EVNLEESGGDLVQPGGSMKLSCLASGFTFSDAWMD WVRQSPEKGLEWVAEIKNKANNYVTFYAASVKGRF TISRDDSKSSVYLQMNNLRPEDTGIYFCTRGSVYGN WFPYWGQGTLVTVSA (SEQ ID NO: 107) | DIVMSQSPSSLAVSAGEKVTMTCKSSQSLFN SRTRKNYLTWYQQKPGQSPKVLIYWASTRE SGVPDRFTGSGSGTDFSLTISSVQADDLAVY YCKQSYNLLTFGAGTRLELK (SEQ ID NO: 125) |
| 6A-23 | EVNLEESGGDLVQPGGSMKLSCLASGFTFSDAWMD WVRQSPEKGLEWVAEIKNKANNYVTFYAASVKGRF TISRDDSKSSVYLQMNSLRLEDTGIYFCTRGSVYGNW FPYWGQGTLVTVSA (SEQ ID NO: 108) | DIVMSQSPSSLAVSAGEKVTMTCKSSQSLFN SRTRKNYLTWYQQKPGQSPKVLIYWASTRE SGVPDRFTGSGSGTDFSLTINSVQADDLAVY YCKQSYNLLTFGAGTKLELK (SEQ ID NO: 126) |

Example 10: Kinetic Characterization of Anti-MS4A6A Antibodies

Binding kinetic characterization of the purified antibodies to MS4A6A ECL1 and ECL2 peptides was performed by Carterra (South San Francisco, CA) using a proprietary array Surface Plasmon Resonance (SPR) instrument (MX-96) as follows. Antibodies were printed onto a CMD5OOD chip (Xantec #SPMX CMD500D lot #SC CMD500D0117. a Exp. 31.12.18) using the Continuous Flow Microspotter (CFM). First, the chip was activated with 100 mM MES pH 5.5, 100 μL EDC (133 mM final), 100 μL of S-NHS (33.3 mM final), for 7 minutes. A lawn of anti-mouse IgG-Fc (Jackson ImmunoResearch CAT #115-005-071 lot #130410) was injected for 15 minutes to establish a surface density of 10000-12000 RU, after which the chip surface was deactivated with 1 M ethanolamine at pH 8.5 for 10 minutes. Anti-MS4A6A antibodies in question, in the form of hybridoma supernatants diluted 2:1 with HBS-EP+buffer (Teknova CAT #H8022), were then printed as duplicates with a 20 minute and a 5 minutes print from the same sample solution. Control antibodies were diluted to 20 μ/ml for printing.

To perform kinetic analysis, the peptides in question were prepared in HBS-EP+buffer with 1 mg/ml BSA at final assay concentrations of 2000 nM, 400 nM, 80 nM, 16 nmM, and 3.2 nM. These were then injected on the chip for five minutes, followed by a seven-minute dissociation period at 8 uL per second in a non-regenerative kinetic series. Duplicate measurements for each anti-MS4A6A antibody were taken to ensure reproducibility.

$K_a$ (association rate constant; $K_{on}$), $K_d$ (dissociation rate constant; $K_{off}$) and KD (equilibrium constant) to MS4A6A ECL-2 peptides were calculated for each of the 23 anti-MS4A6A antibodies tested, the results of which are shown below in Table 5 (clones that bound too weakly to determine these values are denoted as N/A in Table 5). No binding to ECL-1 peptide was observed for any of the anti-MS4A antibodies tested.

TABLE 5

| CLONE NUMBER | $k_a$ (M-1 s-1) $K_{on}$ | $k_d$ (s-1) $K_{off}$ | $K_D$ (M) |
|---|---|---|---|
| 6A-1 | N/A | N/A | N/A |
| 6A-1 | N/A | N/A | N/A |
| 6A-2 | 5.3E+03 | 1.0E-03 | 2.0E-07 |
| 6A-2 | 8.3E+03 | 9.8E-04 | 1.2E-07 |
| 6A-3 | 4.8E+03 | 6.0E-04 | 1.2E-07 |
| 6A-3 | 6.8E+03 | 6.5E-04 | 9.4E-08 |

TABLE 5-continued

| CLONE NUMBER | $k_a$ (M-1 s-1) $K_{on}$ | $k_d$ (s-1) $K_{off}$ | $K_D$ (M) |
|---|---|---|---|
| 6A-4 | N/A | N/A | N/A |
| 6A-4 | N/A | N/A | N/A |
| 6A-5 | N/A | N/A | N/A |
| 6A-5 | N/A | N/A | N/A |
| 6A-6 | N/A | N/A | N/A |
| 6A-6 | N/A | N/A | N/A |
| 6A-7 | N/A | N/A | N/A |
| 6A-7 | N/A | N/A | N/A |
| 6A-8 | N/A | N/A | N/A |
| 6A-8 | 6.3E+03 | 1.0E−03 | 1.7E−07 |
| 6A-9 | 3.9E+03 | 1.1E−03 | 2.9E−07 |
| 6A-9 | N/A | N/A | N/A |
| 6A-10 | N/A | N/A | N/A |
| 6A-10 | 6.6E+03 | 1.3E−03 | 1.9E−07 |
| 6A-11 | N/A | N/A | N/A |
| 6A-11 | N/A | N/A | N/A |
| 6A-12 | 5.2E+03 | 6.7E−04 | 1.3E−07 |
| 6A-12 | 5.1E+03 | 8.1E−04 | 1.6E−07 |
| 6A-13 | 4.8E+03 | 6.6E−04 | 1.4E−07 |
| 6A-13 | 5.3E+03 | 9.2E−04 | 1.8E−07 |
| 6A-14 | 5.7E+03 | 9.6E−04 | 1.7E−07 |
| 6A-14 | 6.9E+03 | 1.0E−03 | 1.5E−07 |
| 6A-15 | 5.0E+03 | 3.8E−04 | 7.6E−08 |
| 6A-15 | 5.0E+03 | 4.3E−04 | 8.6E−08 |
| 6A-16 | 5.5E+03 | 9.7E−04 | 1.8E−07 |
| 6A-16 | 3.4E+03 | 4.9E−04 | 1.5E−07 |
| 6A-17 | N/A | N/A | N/A |
| 6A-17 | N/A | N/A | N/A |
| 6A-18 | N/A | N/A | N/A |
| 6A-18 | 2.7E+03 | 4.9E−04 | 1.8E−07 |
| 6A-19 | 4.5E+03 | 1.3E−04 | 3.0E−08 |
| 6A-19 | 4.4E+03 | 1.0E−05 | 2.3E−09 |
| 6A-20 | N/A | N/A | N/A |
| 6A-20 | N/A | N/A | N/A |
| 6A-21 | 5.3E+03 | 1.0E−03 | 2.0E−07 |
| 6A-21 | N/A | N/A | N/A |
| 6A-22 | 6.0E+03 | 2.3E−03 | 3.9E−07 |
| 6A-22 | 8.4E+03 | 2.1E−03 | 2.5E−07 |
| 6A-23 | 5.4E+03 | 6.5E−04 | 1.2E−07 |
| 6A-23 | 5.5E+03 | 8.0E−04 | 1.5E−07 |

15 of the 23 anti-MS4A6A antibodies bound to the MS4A6A ECL2 peptide and yielded an overall KD value below 10e-07. This largely corresponded to the ELISA data in Example 7 above, except two of the anti-MS4A6A antibodies (6A-6 and 6A-11) were positive for binding as measured by ELISA but did not display binding by Carterra. Among these two antibodies, 6A-6 displayed binding on the SPR traces, though the over signals were weak and thus no KD value was determined. None of the antibodies tested bound to an irrelevant control peptide. Specificity of the assay was affirmed using isotype control antibodies, irrelevant hybridoma clones, anti-HIS control antibody, and medium-alone control; none of these control reagents showed any binding to the cells.

The lack of binding to ECL1 peptide is consistent across both methodologies used. This is likely due to the smaller size of ECL1, which is 18 amino acids in length compared to 48 amino acids of ECL2. If MS4A6A forms a barreled structure similar to that of CD81, a molecule that similarly spans the cell membrane four times, then it is expected that the much larger ECL2 would dominate the exposed surface available for antibody binding. It is possible that certain anti-MS4A6A antibodies identified here recognize epitopes formed by a combination of amino acid residues of ECL1 and ECL2, and thus cannot detected by using methodology. It is noted that human and cyno MS4A6A ECL1 have identical amino acid sequences; thus lack of cross-reactivity is not of concern.

Example 11: Affinity Measurement of MS4A6A Antibodies to Transiently and Natively-Expressing Cell Line Purified anti-MS4A6A antibodies are evaluated for their binding affinity to various MS4A6A-expressing cell lines including HEK293 transiently-transfected with human or cyno MS4A6A expression plasmids, as well as HeLa cells and A549 cells. Antibodies tested are either mouse IgGs purified from hybridoma supernatant or human IgG1 Fc chimeras produced recombinantly in Expi293 cells. Affinity binding to cells is determined as follows. Briefly, cells are harvested, washed and labeled with Aqua Live/Dead for viability discrimination. After a wash with PBS, 2×10^5 cells are aliquoted per well in 96-well U-bottom plates and incubated with 50 µL of purified anti-MS4A6A antibody at various concentrations (3× dilutions starting at 10 µg/mL) in FACS buffer (PBS+2% FBS+1 mM EDTA). After primary incubation, the supernatant is removed via centrifugation, washed 2× with 150 µL of ice-cold FACS buffer and incubated with the appropriate secondary antibody on ice for 30 minutes. Following the secondary incubation, the cells are again washed 2× with ice-cold FACS buffer and resuspended in a final volume of 200 µL of FACS buffer. Flow cytometry analysis is performed on a FACSCanto system (BD Biosciences). Binding data is analyzed using mean fluorescent intensity, and curves are fitted in Prism (nonlinear regression: log inhibitor vs. dose response with four parameters) to determine EC50 values.

Example 12: Epitope Determination of Anti-MS4A6A Antibodies by Peptide Binding

Additional binding characterization of the anti-MS4A6A antibodies is performed as follows. Specifically, epitope mapping of the anti-MS4A6A antibodies is performed by Carterra using a pre-mix epitope binning approach. Epitope binding characteristics of anti-MS4A6A antibodies are determined by two complementary approaches. First, a panel of overlapping peptides derived from the extracellular loops are synthesized by JPT peptides (Berlin, Germany) or Elim Biopharm (Hayward, CA, USA). These are then transferred to Carterra (South San Francisco, CA, USA) which uses a proprietary array surface plasmon resonance (SPR) instrument (MX-96) to determine binding characteristics, using a protocol analogous to that described above, as follows.

The peptide library is printed onto a CMD500D chip using the Continuous Flow Microspotter (CFM). First, the chip is activated with 100 mM MES pH 5.5, EDC (133 mM final), 100 µL of S-NHS (33.3 mM final). The peptide library is immobilized onto the chip, after which the chip surface is deactivated with 1 M ethanolamine at pH 8.5 for 10 minutes. Anti-MS4A6A antibodies to be tested are prepared in HBS-EP+buffer with 1 mg/ml BSA at various final assay concentrations. These are then injected on the chip for five minutes, followed by a seven-minute dissociation period at 8 µL per second in a non-regenerative kinetic series. Duplicate measurements for each anti-MS4A6A antibody are taken to ensure reproducibility. Binding characteristics are determined for each peptide-antibody combination, allowing the mapping of the linear peptide region each antibody interacts with.

Some anti-MS4A6A antibodies bind to discontinuous epitopes. Pepscan (Lelstad, The Netherlands) has developed technology, known as Chemical Linkage of Peptides onto Scaffolds (CLIPS), designed to address such epitopes. In this technology, a library of tertiary-structure mimics is designed and synthesized onto a solid support. These mimics can model secondary structural elements in proteins, such as loops, alpha-helices and beta-strands. The binding of the antibody to each peptide construct is determined and quantified. The extent of binding to the library indicates the region to which a given antibody interacts with, thus its epitope.

Example 13: Epitope Binning of Anti-MS4A6A Antibodies by Cell Binding

As MS4A6A is a multi-pass transmembrane protein, recombinantly produced soluble proteins may not be appropriate reagents for investigating Ab:protein interactions. Anti-MS4A6A antibodies are binned using a cell-based variant of the classical sandwich method. To determine whether antibodies A and B, for example, are in the same bin, cells expressing MS4A6A are first incubated with saturating levels of antibody A. After washes with FACS buffer, antibody B, labeled with fluorophore allophycocyanin (APC), is added to the cells for incubation on ice for 15 minutes. The cells are analyzed by FACS Canto system (BD Biosciences), with gates drawn to exclude dead cells. The level of antibody B binding in the presence or absence of antibody A are compared. Reduction or extinction of binding in the presence of antibody A indicates competition between these two antibodies. This procedure is repeated against other antibodies so the entire panel is binned.

Example 14: Downregulation of MS4A6A by Anti-MS4A6A Antibodies in Cell Lines The ability of anti-MS4A6A antibodies to reduce cell surface and total cellular protein levels of MS4A6A in various cell lines is evaluated as follows. Reduction in MS4A6A protein in either compartment indicates a reduction in MS4A6A activity in the cells.

Cell lines expressing MS4A6A are incubated with anti-MS4A6A antibodies of the present disclosure for various time periods and then the levels of MS4A6A remaining associated with the cells assayed by either FACS (cell surface) or western blot (total protein level). For FACS assays, detection of the remaining MS4A6A is carried out with direct-allophycocyanin (APC) conjugated, non-competing antibodies. For Western blot detection, cells are lysed by the addition of 50 uL lysis buffer (RIPA lysis buffer (ThermoFischer Scientific CAT #89900)+1:100 HALT protease inhibitor cocktail (ThermoFischer Scientific CAT #87786)), and cleared for insoluble debris by centrifugation at 14,000 ×g for 15 minutes. Soluble fraction is assayed with bicinchoninic acid (BCA) reagent for protein quantification. Equal amounts of proteins from each sample are loaded on a 4-12% Bis-Tris Plus polyacrylamide gel (ThermoFisher Scientific NW04120) and subjected to electrophoresis separation, after which proteins in the gel are transferred onto a polyvinylidene difluoride (PVDF) membrane using iBlot2 (ThermoFisher Scientific IM21001) and Transfer Stacks (ThermoFisher Scientific IB24002). The membrane is blocked with either 1% bovine serum albumin or 5% non-fat milk to prevent non-specific binding. It is then incubated with in-house or commercial detection antibodies, washed, and incubated with HRP-conjugated secondary antibody (rabbit, Abcam #205718; mouse, Abcam #205719). Binding is visualized by developing with SuperSignal West Pico Plus chemiluminescent substrate (ThermoFisher Scientific #34577), and recorded digitally with iBright FL1000 (ThermoFisher Scientific A32752) or other compatible systems.

Example 15: Downregulation of MS4A6A by Anti-MS4A6A Antibodies in Primary Cell Cultures The ability of anti-MS4A6A antibodies of the present disclosure to reduce or down-regulate cell surface/cellular expression in primary cell cultures is evaluated as follows. Mouse primary cortical neurons are harvested from early postnatal mice (day 0-3) and cultured according to standard methods in the field (Maximov et al. (2007), J. Neu. Meth., 161 75-87). Cultured neurons are then incubated with anti-MS4A6A antibodies in various conditions (1-20 ug/mL, 2-48 hrs), harvested, and total MS4A6A levels quantified via either FACS (for cell-surface levels) or Western blot (for total protein levels).

Primary cortical neurons are isolated as follows. Briefly, cells in the cortex, hippocampus, or striatum of P0 mouse pups are dissociated by incubation for 7 min at 37° C. in digestion solution containing 6 mg/ml trypsin (Sigma, CAT #T1005-1G), 0.5 mg/ml DNAse (Sigma, CAT #D5025) and (in mM) 137 NaCl, 5 KCl, 7 Na2HPO4, and 25 HEPES—NaOH pH 7.2. The dissociated cells containing neurons are then washed once with Hank's balanced salt solution (HBS) containing 20% fetal bovine serum (FBS) followed by two washes in serum-free HBS, and further dissociated by gentle pipetting in HBS containing 12 mM MgSO4 and 0.5 mg/ml DNAse. The cell suspension is centrifuged for 10 min at 160 g and plated on Matrigel (Collaborative Biomedical Products, CAT #871-275-0004) coated circular glass coverslips (Ø 12 mm) in MEM (Invitrogen) supplemented with B27 (Invitrogen, CAT #17504-044), glucose, transferrin and 5% fetal bovine serum. For cortical cultures, the cell suspension obtained from the cortex of a single brain is used to plate 12 wells in a 24-well plate. For all cultures, the initial cell density (including glia) at plating varies between 1500 and 2500 per square millimeter. When the confluency of glia cells in the culture reached ~40-50% (usually 2 days after plating), 50% of the conditioned culture medium is replaced with fresh medium containing 4 mM Ara-C (Sigma). The cultures are maintained in medium containing 2 mM Ara-C at 37° C. and 5% $CO_2$ until experiments (13-18 DIV).

Primary neurons in culture are then incubated with anti-MS4A6A antibodies of the present disclosure for various time periods and then the levels of MS4A6A remaining associated with the cells assayed by either FACS (cell surface) or western blot (total protein level), as described above in Example 14.

Example 16: Intracellular Signal Transduction Triggered by Anti-MS4A6A Antibodies As a membrane-bound molecule, MS4A6A may directly or indirectly be involved in the cells' interaction with extracellular signals. Other molecules in the MS4A family have been shown to be components of surface receptor complexes and to modulate signal transduction. The topology of MS4A6A suggests that it has the capacity to act as an ion-channel, by forming a bundled barrel across the plasma membrane. Calcium is a common second messenger for such ion channels. The potential for anti-MS4A6A antibodies to induce or increase calcium flux in cell lines and primary cells is investigated as follows. Cells are loaded with a calcium-sensitive dye such as Fura-2, Indo-1 or Fluo-4 (ThermoFisher Scientific). Cells are then incubated with anti-MS4A6A antibodies for up to thirty minutes and the level of fluorescence monitored by a flow cytometer, a fluorescent microscope or a fluorospectrometer.

MS4A6A may also modulate other signaling events directly or indirectly. In particular, protein phosphorylation/dephosphorylation is a major mechanism for intracellular signal transduction. While MS4A6A contains no defined protein motifs associated with phosphorylation activity, MS4A6A does contain several tyrosine residues in the intracellular C-terminus region. The most distal of these tyrosine residues resembles the consensus sequence of hemi-ITAM, a motif used by a number of receptors to engage Src homology 2 (SH2)-containing adaptor molecules to mediate downstream signaling. MS4A6A may use a hemi-ITAM motif to transmit downstream signals. Alternatively, MS4A6A may modulate downstream phosphorylation or dephosphorylation events through interaction with other signaling molecules.

To examine this, MS4A6A-expressing cell lines and primary cells are incubated with anti-MS4A6A antibodies. At various treatment time points, cells are harvested and analyzed for their intracellular protein serine/threonine phosphorylation or tyrosine phosphorylation by Western Blotting. For Western blot detection, cells are lysed by the addition of 50 uL lysis buffer (RIPA lysis buffer (ThermoFischerScientific CAT #89900)+1:100 HALT protease inhibitor cocktail (ThermoFischerScientific CAT #87786)), and cleared for insoluble debris by centrifugation at 14000×g for 15 minutes. Soluble fraction is assayed with bicinchoninic acid (BCA) reagent for protein quantification. Equal amounts of proteins from each sample are loaded on a 4-12% Bis-Tris Plus polyacrylamide gel (ThermoFisher Scientific NW04120) and subjected to electrophoresis separation, after which proteins in the gel are transferred onto a polyvinylidene difluoride (PVDF) membrane using iBlot2 (ThermoFisher Scientific IM21001) and Transfer Stacks (ThermoFisher Scientific IB24002). The membrane is blocked with either 1% bovine serum albumin or 5% non-fat milk to prevent non-specific binding. It is then incubated with in-house or commercial detection antibodies directed against serine/threonine phosorylation or tyrosine phosphorylation. The membrane is then washed, and incubated with HRP-conjugated secondary antibody (rabbit, Abcam #205718; mouse, Abcam #205719). Binding is visualized by developing with SuperSignal West Pico Plus chemiluminescent substrate (ThermoFisher Scientific #34577), and recorded digitally with iBright FL1000 (ThermoFisher A32752) or other compatible systems.

It is possible that MS4A6A does not engage extracellular ligands directly, but rather may exerts its effect on other cellular receptors in a receptor protein complex on the plasma membrane. For example, MS4A6A may form protein complexes with toll-like receptors (TLRs), cytokine receptors, chemokine receptors, scavenger receptors, Triggering Receptors Expressed on Myeloid cells 1 or 2, inhibitory receptors such as CD33, Siglec family or CD200, Fc receptors, or other cell surface receptors that modulate myeloid cell or microglia cell function. To examine this, MS4A6A-expressing cell lines and primary cells are co-engaged with both the cognate ligands of these receptors and anti-MS4A6A antibodies. Downstream signaling events such as calcium mobilization and protein phosphorylation are examined as described above. In addition, changes in gene expression are analyzed through RT-PCR or global profiling methods such as RNASeq or microarrays.

Example 17: Characterization of Interactions Between MS4A6A and Binding Partners Use of anti-MS4A6A antibodies to block the interaction of MS4A6A with various binding partners may be tested. Little is known about which proteins interact with MS4A6A in vivo. To identify such binding partners, MS4A6A is immunoprecipitated from myeloid cell lines and primary cells. The immunoprecipitated complexes are then subjected to tandem mass spectrometry to identify proteins that have co-precipitated with MS4A6A. Once identified, this interaction is further confirmed by western blotting or fluorescence resonance energy transfer (FRET) analyses. Alternatively, MS4A6A-expressing cell lines may be administered anti-MS4A6A antibodies and then stained for both MS4A6A and a potential binding partner, with the readout being either co-localization or fluorescence resonance energy transfer (FRET).

Example 18: Characterization of the Effects of Anti-MS4A6A Antibodies on Myeloid Cell Metabolism, Biology, and Function The downstream sequelae of engagement of anti-MS4A6A antibodies binding to their target on myeloid cells, including microglia in the CNS, is examined in detail using cultures of myeloid cell lines and primary cells, such as for example monocyte-derived macrophages and dendritic cells, as model systems. These cells are widely used to investigate the biology of myeloid cells as their functions are regularly studied in vitro. These functions include, but are not limited to, energy metabolism, cytokine production, phagocytosis, cell surface molecule expression, polarization, migration, and antigen presentation. Briefly, MS4A6A-expressing cells are incubated with anti-MS4A6A antibodies presented in plate-bound, soluble, or pre-complexed formats, which mimic the different ways antibodies are presented to their cellular target in vivo. The incubation conditions and times depend on the readout to be analyzed, but in general range from about 1 hour to about seven days. After incubation, cells are harvested and lysed for mRNA or protein analyses. The cells are also subjected to flow cytometry analysis for cell surface molecule expression.

For metabolic studies, cells are incubated with CellTiter-Glo (Promega) or other compatible reagents, which measures ATP content within the cells or other parameters for cell viability. Culture supernatants are harvested and subjected to ELISA or other similar methods to determine secretion of cytokines, chemokines, and other molecules following treatment with anti-MS4A6A antibodies. Phagocytosis capacity of treated cells is determined by feeding cells with fluorescently-labelled substrates such as latex beads, bacterial or fungal particles, and aggregate particles of protein such as A-beta, Tau or prion molecules. Cell migration is determined by the macrophage scratch assay (Liang et. al., Nature Protocols 2007; 2(2): 329) or the transwell assay (Corning, Corning, NY, USA).

Example 19: Characterization of the Effects of Anti-MS4A6A Antibodies Utilizing Animal Models for Aging, Seizures, Spinal Cord Injury, Retinal Dystrophy, Frontotemporal Dementia, and Alzheimer's Disease The therapeutic utility of anti-MS4A6A antibodies can also be tested in animal models for aging, seizures, spinal cord injury, retinal dystrophy, frontotemporal dementia, and Alzheimer disease, as previously described (e.g., Beattie, M S et al., (2002) Neuron 36, 375-386; Volosin, M et al., (2006) J. Neurosci. 26, 7756-7766; Nykjaer, A et al., (2005) Curr. Opin. Neurobiol. 15, 49-57; Jansen, P et al., (2007) Nat. Neurosci. 10, 1449-1457; Volosin, M et al., (2008) J. Neurosci. 28, 9870-9879; Fahnestock, M et al., (2001) Mol. Cell Neurosci. 18, 210-220; Nakamura, K et al., (2007) Cell Death. Differ. 14, 1552-1554; Yune, T et al., (2007) Brain Res. 1183, 32-42; Wei, Y et al., (2007) Neurosci. Lett. 429, 169-174; Provenzano, M J et al., (2008) Laryngoscope 118, 87-93; Nykjaer, A et al., (2004) Nature 427, 843-848; Harrington, A W et al., (2004) Proc. Natl. Acad. Sci. U.S.A. 101, 6226-6230; Teng, H K et al., (2005) J. Neurosci. 25, 5455-5463; Jansen, P et al., (2007) Nat. Neurosci. 10, 1449-1457; Volosin, M et al., (2008) J. Neurosci. 28, 9870-9879; Fan, Y J et al., (2008) Eur. J. Neurosci. 27, 2380-2390; Al-Shawi, R et al., (2008) Eur. J. Neurosci. 27, 2103-2114; and Yano, H et al., (2009) J. Neurosci. 29, 14790-14802).

Example 20: Characterization of the Effects of Anti-MS4A6A Antibodies Utilizing Animal Models for Oncology Myeloid cells represent a major component of the immune cells present in most solid tumors. Due to the plasticity of myeloid cells, their role in tumor biology is context-dependent—while they have the potential to play a key role in the eradication of tumors, they are most often co-opted by the host tumor to assist in providing a pro-tumor phenotype. This can be achieved, for example, through the polarization of myeloid cells towards the M2-phenotype, which is typically immunosuppressive and thus block the immune system from engaging and eradicating the tumor. Anti-MS4A6A antibodies, through repolarization of myeloid cells, may reverse this immunosuppressive phenotype and promote an anti-tumor immune response.

Numerous animal tumor models exist. Models most relevant to MS4A6A are the humanized mouse models, where the mouse immune system is genetically deleted, as typified by the NSG mice (Jackson Laboratory, Bar Harbor, Maine). These mice act as receptive hosts for human immune cells, leading to the engraftment of human adaptive and innate immune cells. These animals are then inoculated with tumor cells, usually under the skin on the flanks. Tumor size over time represents the balance between the growth of tumor cells and their eradication by the host immune system. Throughout the time course the animals are treated with anti-MS4A6A antibodies, which modifies tumor progression when compared to isotype-treated animals. At the end of treatment period tumors are extracted and subjected to various analyses to determine the effect of anti-MS4A6A antibodies on the tumor cells and infiltrating immune cells. Tumors can be sectioned, mounted onto slides and analyzed under the microscope for histological changes. mRNA can be analyzed by RT-PCR, RNASeq or microarray to determine changes in gene expression. Single cell suspensions of tumor and infiltrating immune cells can be prepared, stained with antibodies against various cell surface markers and analyzed by flow cytometry, to delineate changes in cell surface phenotype, especially in immune cells such as macrophages and T cells. Changes observed as a result of anti-MS4A6A treatment in any of these analyses indicates an immune-modulatory function for these antibodies.

What is claimed is:

1. An isolated antibody that binds to human MS4A6A, wherein the antibody comprises a heavy chain variable region and a light chain variable region, wherein:

(i) the heavy chain variable region comprises
an HVR-H1 comprising the amino acid sequence of SEQ ID NO: 14;
an HVR-H2 comprising the amino acid sequence of SEQ ID NO: 29;
an HVR-H3 comprising the amino acid sequence of SEQ ID NO: 43; and
the light chain variable region comprises:
an HVR-L1 comprising the amino acid sequence of SEQ ID NO: 57;
an HVR-L2 comprising the amino acid sequence of SEQ ID NO: 73; and
an HVR-L3 comprising the amino acid sequence of SEQ ID NO: 84;
or
(ii) the heavy chain variable region comprises:
an HVR-H1 comprising the amino acid sequence of SEQ ID NO: 11;
an HVR-H2 comprising the amino acid sequence of SEQ ID NO: 24;
an HVR-H3 comprising the amino acid sequence of SEQ ID NO: 39; and
the light chain variable region comprises:
an HVR-L1 comprising the amino acid sequence of SEQ ID NO: 53;
an HVR-L2 comprising the amino acid sequence of SEQ ID NO: 68; and
an HVR-L3 comprising the amino acid sequence of SEQ ID NO: 84.

2. The antibody of claim 1, wherein the antibody comprises
an HVR-H1 comprising the amino acid sequence of SEQ ID NO: 14;
an HVR-H2 comprising the amino acid sequence of SEQ ID NO: 29;
an HVR-H3 comprising the amino acid sequence of SEQ ID NO: 43;
an HVR-L1 comprising the amino acid sequence of SEQ ID NO: 57;
an HVR-L2 comprising the amino acid sequence of SEQ ID NO: 73; and
an HVR-L3 comprising the amino acid sequence of SEQ ID NO: 84.

3. The antibody of claim 2, wherein the heavy chain variable region and light chain variable region comprise the amino acid sequences of SEQ ID NOs: 104 and 121, respectively.

4. The antibody of claim 2, wherein the antibody is a monoclonal antibody.

5. The antibody of claim 3, wherein the antibody is of the IgG class, the IgM class, or the IgA class.

6. The antibody of claim 5, wherein the antibody is of the IgG class and has an IgG1, IgG2, or IgG4 isotype.

7. The antibody of claim 3, wherein the antibody is an antibody fragment.

8. The antibody of claim 7, wherein the fragment is a Fab, Fab', Fab'-SH, F(ab')2, Fv or scFv fragment.

9. The antibody of claim 2, wherein the antibody is a multispecific antibody comprising a first antigen binding region that binds to MS4A6A and a second antigen binding region that binds to a second target, wherein the second target is
a protein, lipid, polysaccharide, or glycolipid expressed on one or more tumor cells.

10. A pharmaceutical composition comprising the antibody of claim 2 and a pharmaceutically acceptable carrier.

11. A pharmaceutical composition comprising the antibody of claim 3 and a pharmaceutically acceptable carrier.

12. The antibody of claim 1, wherein the antibody comprises
an HVR-H1 comprising the amino acid sequence of SEQ ID NO: 11;
an HVR-H2 comprising the amino acid sequence of SEQ ID NO: 24;
an HVR-H3 comprising the amino acid sequence of SEQ ID NO: 39;
an HVR-L1 comprising the amino acid sequence of SEQ ID NO: 53;
an HVR-L2 comprising the amino acid sequence of SEQ ID NO: 68; and
an HVR-L3 comprising the amino acid sequence of SEQ ID NO: 84.

13. The antibody of claim 12, wherein the heavy chain variable region and light chain variable region comprises the amino acid sequences of SEQ ID NOs: 98 and 116, respectively.

14. The antibody of claim 13, wherein the antibody is of the IgG class, the IgM class, or the IgA class.

15. The antibody of claim 14, wherein the antibody is of the IgG class and has an IgG1, IgG2, or IgG4 isotype.

16. The antibody of claim 13, wherein the antibody is an antibody fragment.

17. The antibody of claim 16, wherein the fragment is a Fab, Fab', Fab'-SH, F (ab') 2, Fv or scFv fragment.

18. A pharmaceutical composition comprising the antibody of claim 12 and a pharmaceutically acceptable carrier.

19. A pharmaceutical composition comprising the antibody of claim 14 and a pharmaceutically acceptable carrier.

* * * * *

SEQUENCE LISTING

```
<160> NUMBER OF SEQ ID NOS: 130

<210> SEQ ID NO 1
<211> LENGTH: 248
<212> TYPE: PRT
<213> ORGANISM: Homo sapiens

<400> SEQUENCE: 1

Met Thr Ser Gln Pro Val Pro Asn Glu Thr Ile Ile Val Leu Pro Ser
1               5                   10                  15

Asn Val Ile Asn Phe Ser Gln Ala Glu Lys Pro Glu Pro Thr Asn Gln
            20                  25                  30

Gly Gln Asp Ser Leu Lys Lys His Leu His Ala Glu Ile Lys Val Ile
        35                  40                  45

Gly Thr Ile Gln Ile Leu Cys Gly Met Met Val Leu Ser Leu Gly Ile
    50                  55                  60

Ile Leu Ala Ser Ala Ser Phe Ser Pro Asn Phe Thr Gln Val Thr Ser
65                  70                  75                  80

Thr Leu Leu Asn Ser Ala Tyr Pro Phe Ile Gly Pro Phe Phe Phe Ile
                85                  90                  95

Ile Ser Gly Ser Leu Ser Ile Ala Thr Glu Lys Arg Leu Thr Lys Leu
            100                 105                 110

Leu Val His Ser Ser Leu Val Gly Ser Ile Leu Ser Ala Leu Ser Ala
        115                 120                 125

Leu Val Gly Phe Ile Ile Leu Ser Val Lys Gln Ala Thr Leu Asn Pro
    130                 135                 140

Ala Ser Leu Gln Cys Glu Leu Asp Lys Asn Asn Ile Pro Thr Arg Ser
145                 150                 155                 160

Tyr Val Ser Tyr Phe Tyr His Asp Ser Leu Tyr Thr Thr Asp Cys Tyr
                165                 170                 175
```

```
Thr Ala Lys Ala Ser Leu Ala Gly Thr Leu Ser Leu Met Leu Ile Cys
            180                 185                 190

Thr Leu Leu Glu Phe Cys Leu Ala Val Leu Thr Ala Val Leu Arg Trp
            195                 200                 205

Lys Gln Ala Tyr Ser Asp Phe Pro Gly Ser Val Leu Phe Leu Pro His
            210                 215                 220

Ser Tyr Ile Gly Asn Ser Gly Met Ser Ser Lys Met Thr His Asp Cys
225                 230                 235                 240

Gly Tyr Glu Glu Leu Leu Thr Ser
                245

<210> SEQ ID NO 2
<211> LENGTH: 139
<212> TYPE: PRT
<213> ORGANISM: Mus musculus

<400> SEQUENCE: 2

Met Thr Lys Pro Leu Val His Ser Ser Leu Ala Leu Ser Ile Leu Ser
1               5                   10                  15

Val Leu Ser Ala Leu Thr Gly Ile Ala Ile Leu Ser Val Ser Leu Ala
            20                  25                  30

Ala Leu Glu Pro Ala Leu Gln Gln Cys Lys Leu Ala Phe Thr Gln Leu
        35                  40                  45

Asp Thr Thr Gln Asp Ala Tyr His Phe Phe Ser Pro Glu Pro Leu Asn
    50                  55                  60

Ser Cys Phe Val Ala Lys Ala Ala Leu Thr Gly Val Phe Ser Leu Met
65                  70                  75                  80

Leu Ile Ser Ser Val Leu Glu Leu Gly Leu Ala Val Leu Thr Ala Thr
                85                  90                  95

Leu Trp Trp Lys Gln Ser Ser Ser Ala Phe Ser Gly Asn Val Ile Phe
            100                 105                 110

Leu Ser Gln Asn Ser Lys Asn Lys Ser Ser Val Ser Ser Glu Ser Leu
        115                 120                 125

Cys Asn Pro Thr Tyr Glu Asn Ile Leu Thr Ser
    130                 135

<210> SEQ ID NO 3
<211> LENGTH: 247
<212> TYPE: PRT
<213> ORGANISM: Macaca fascicularis

<400> SEQUENCE: 3

Met Thr Ser Gln Pro Val Pro Asn Glu Thr Met Ile Val Leu Pro Ser
1               5                   10                  15

Asn Val Ile Asn Phe Ser Gln Ala Glu Lys Pro Glu Pro Thr Asn Gln
            20                  25                  30

Gly Gln Asp Ser Leu Lys Lys Arg Leu Gln Ala Glu Val Lys Val Ile
        35                  40                  45

Gly Thr Ile Gln Ile Leu Cys Gly Val Met Val Leu Ser Leu Gly Ile
    50                  55                  60

Met Leu Ala Ser Ala Ser Phe Pro Asn Phe Thr Gln Val Thr Ser
65                  70                  75                  80

Thr Leu Leu Asn Ser Ala Tyr Pro Phe Ile Gly Pro Phe Phe Phe Ile
                85                  90                  95

Ile Ser Gly Ser Leu Ser Ile Ala Thr Glu Lys Lys Leu Thr Lys Leu
            100                 105                 110
```

```
Leu Val His Ser Ser Leu Val Gly Ser Ile Leu Ser Ala Leu Ser Ala
        115                 120                 125

Leu Val Gly Phe Ile Ile Leu Ser Val Glu Leu Ala Ala Leu Asn Pro
130                 135                 140

Ala Ser Leu Gln Cys Glu Leu Asp Lys Asn Asn Ile Pro Thr Arg Ser
145                 150                 155                 160

Tyr Val Ser Tyr Tyr His Asp Ser Leu Tyr Thr Met Asp Cys Tyr
                165                 170                 175

Thr Val Lys Ala Ser Leu Ala Gly Pro Leu Ser Leu Met Leu Ile Cys
            180                 185                 190

Thr Leu Leu Glu Phe Cys Leu Ala Val Leu Thr Ala Val Leu Arg Trp
            195                 200                 205

Lys Gln Thr Val Ser Asp Phe Pro Gly Ser Val Leu Phe Leu Pro His
        210                 215                 220

Ser Tyr Ile Asp Asn Ser Gly Met Ser Ser Lys Met Thr His Gly Pro
225                 230                 235                 240

Gly Tyr Glu Glu Leu Leu Ser
                245

<210> SEQ ID NO 4
<211> LENGTH: 5
<212> TYPE: PRT
<213> ORGANISM: Artificial Sequence
<220> FEATURE:
<223> OTHER INFORMATION: Synthetic Construct

<400> SEQUENCE: 4

Gly Tyr Tyr Met His
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic Construct

<400> SEQUENCE: 5

Ser Gly Tyr Tyr Trp Asn
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Construct

<400> SEQUENCE: 6

Asp Tyr Phe Met Lys
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic Construct

<400> SEQUENCE: 7

Ser Tyr Trp Ile Asn
1               5
```

```
<210> SEQ ID NO 8
<211> LENGTH: 5
<212> TYPE: PRT
<213> ORGANISM: Artificial Sequence
<220> FEATURE:
<223> OTHER INFORMATION: Synthetic Construct

<400> SEQUENCE: 8

Asn Tyr Gly Met Asn
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Construct

<400> SEQUENCE: 9

Ser Tyr Ala Met His
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic Construct

<400> SEQUENCE: 10

Asp Tyr Tyr Ile Asn
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic Construct

<400> SEQUENCE: 11

Gly Tyr Tyr Ile His
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic Construct

<400> SEQUENCE: 12

Asp Tyr Tyr Met Thr
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic Construct

<400> SEQUENCE: 13

Thr Tyr Gly Val His
1               5
```

```
<210> SEQ ID NO 14
<211> LENGTH: 5
<212> TYPE: PRT
<213> ORGANISM: Artificial Sequence
<220> FEATURE:
<223> OTHER INFORMATION: Synthetic Construct

<400> SEQUENCE: 14

Ser His Ala Met Ser
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic Construct

<400> SEQUENCE: 15

Ser Tyr Gly Val His
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic Construct

<400> SEQUENCE: 16

Asp Ala Trp Met Asp
1               5

<210> SEQ ID NO 17
<211> LENGTH: 17
<212> TYPE: PRT
<213> ORGANISM: Artificial Sequence
<220> FEATURE:
<223> OTHER INFORMATION: Synthetic Construct

<400> SEQUENCE: 17

Ala Ile Asn Pro Ser Thr Gly Gly Ser Thr Tyr Ser Gln Lys Phe Lys
1               5                   10                  15

Asp

<210> SEQ ID NO 18
<211> LENGTH: 16
<212> TYPE: PRT
<213> ORGANISM: Artificial Sequence
<220> FEATURE:
<223> OTHER INFORMATION: Synthetic Construct

<400> SEQUENCE: 18

Tyr Ile Thr Tyr Asp Gly Asp Thr Asp Tyr Asn Pro Ser Leu Lys Asn
1               5                   10                  15

<210> SEQ ID NO 19
<211> LENGTH: 17
<212> TYPE: PRT
<213> ORGANISM: Artificial Sequence
<220> FEATURE:
<223> OTHER INFORMATION: Synthetic Construct

<400> SEQUENCE: 19

Asp Ile Asn Pro Lys Asn Gly Asp Thr Phe Tyr Asn Gln Lys Phe Lys
1               5                   10                  15
```

Gly

<210> SEQ ID NO 20
<211> LENGTH: 17
<212> TYPE: PRT
<213> ORGANISM: Artificial Sequence
<220> FEATURE:
<223> OTHER INFORMATION: Synthetic Construct

<400> SEQUENCE: 20

```
Asp Ile Tyr Pro Gly Ser Gly Ser Thr Asn Tyr Asp Glu Lys Phe Lys
1               5                   10                  15

Ser
```

<210> SEQ ID NO 21
<211> LENGTH: 17
<212> TYPE: PRT
<213> ORGANISM: Artificial Sequence
<220> FEATURE:
<223> OTHER INFORMATION: Synthetic Construct

<400> SEQUENCE: 21

```
Tyr Ile Asn Ile Tyr Ser Gly Lys Ser Arg Tyr Ala Asp Asp Phe Lys
1               5                   10                  15

Gly
```

<210> SEQ ID NO 22
<211> LENGTH: 17
<212> TYPE: PRT
<213> ORGANISM: Artificial Sequence
<220> FEATURE:
<223> OTHER INFORMATION: Synthetic Construct

<400> SEQUENCE: 22

```
Tyr Ile Asn Pro Ser Ser Gly Tyr Thr Tyr Tyr Asn Gln Lys Phe Lys
1               5                   10                  15

Asp
```

<210> SEQ ID NO 23
<211> LENGTH: 17
<212> TYPE: PRT
<213> ORGANISM: Artificial Sequence
<220> FEATURE:
<223> OTHER INFORMATION: Synthetic Construct

<400> SEQUENCE: 23

```
Glu Ile Tyr Pro Arg Ser Gly Asn Ala Tyr Tyr Asn Glu Lys Phe Arg
1               5                   10                  15

Gly
```

<210> SEQ ID NO 24
<211> LENGTH: 17
<212> TYPE: PRT
<213> ORGANISM: Artificial Sequence
<220> FEATURE:
<223> OTHER INFORMATION: Synthetic Construct

<400> SEQUENCE: 24

```
Arg Ile Asn Pro Lys Asn Gly Val Thr Ser Tyr Asn Gln Asn Phe Lys
1               5                   10                  15

Asp
```

```
<210> SEQ ID NO 25
<211> LENGTH: 17
<212> TYPE: PRT
<213> ORGANISM: Artificial Sequence
<220> FEATURE:
<223> OTHER INFORMATION: Synthetic Construct

<400> SEQUENCE: 25

Trp Ile Asn Thr Tyr Thr Gly Glu Pro Thr Tyr Ala Asp Asp Phe Lys
1               5                   10                  15
Gly

<210> SEQ ID NO 26
<211> LENGTH: 17
<212> TYPE: PRT
<213> ORGANISM: Artificial Sequence
<220> FEATURE:
<223> OTHER INFORMATION: Synthetic Construct

<400> SEQUENCE: 26

Arg Ile Asn Pro Asn Asn Gly Ala Thr Asn Tyr Asn Gln Ile Phe Lys
1               5                   10                  15
Asp

<210> SEQ ID NO 27
<211> LENGTH: 19
<212> TYPE: PRT
<213> ORGANISM: Artificial Sequence
<220> FEATURE:
<223> OTHER INFORMATION: Synthetic Construct

<400> SEQUENCE: 27

Phe Ile Arg Asn Lys Ala Asn Gly Tyr Thr Thr Glu Tyr Asn Ser Ser
1               5                   10                  15
Val Lys Gly

<210> SEQ ID NO 28
<211> LENGTH: 16
<212> TYPE: PRT
<213> ORGANISM: Artificial Sequence
<220> FEATURE:
<223> OTHER INFORMATION: Synthetic Construct

<400> SEQUENCE: 28

Val Ile Trp Ser Gly Gly Ser Thr Asp Tyr Asn Ala Ala Phe Ile Ser
1               5                   10                  15

<210> SEQ ID NO 29
<211> LENGTH: 17
<212> TYPE: PRT
<213> ORGANISM: Artificial Sequence
<220> FEATURE:
<223> OTHER INFORMATION: Synthetic Construct

<400> SEQUENCE: 29

Thr Ile Ser Ser Gly Asp Ser Tyr Thr Tyr Tyr Pro Asp Ser Val Lys
1               5                   10                  15
Gly

<210> SEQ ID NO 30
<211> LENGTH: 16
<212> TYPE: PRT
<213> ORGANISM: Artificial Sequence
<220> FEATURE:
<223> OTHER INFORMATION: Synthetic Construct
```

```
<400> SEQUENCE: 30

Val Ile Trp Ser Asp Gly Ser Thr Thr Tyr Asn Ser Ala Leu Lys Ser
1               5                   10                  15

<210> SEQ ID NO 31
<211> LENGTH: 19
<212> TYPE: PRT
<213> ORGANISM: Artificial Sequence
<220> FEATURE:
<223> OTHER INFORMATION: Synthetic Construct

<400> SEQUENCE: 31

Glu Ile Lys Asn Lys Ala Asn Asn Tyr Val Thr Phe Tyr Ala Ala Ser
1               5                   10                  15

Val Lys Gly

<210> SEQ ID NO 32
<211> LENGTH: 6
<212> TYPE: PRT
<213> ORGANISM: Artificial Sequence
<220> FEATURE:
<223> OTHER INFORMATION: Synthetic Construct

<400> SEQUENCE: 32

Phe Asp Gly Tyr Gly Tyr
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic Construct

<400> SEQUENCE: 33

Glu Asp Ser Phe Gly Tyr
1               5

<210> SEQ ID NO 34
<211> LENGTH: 6
<212> TYPE: PRT
<213> ORGANISM: Artificial Sequence
<220> FEATURE:
<223> OTHER INFORMATION: Synthetic Construct

<400> SEQUENCE: 34

Pro Gly Tyr Phe Asp Val
1               5

<210> SEQ ID NO 35
<211> LENGTH: 10
<212> TYPE: PRT
<213> ORGANISM: Artificial Sequence
<220> FEATURE:
<223> OTHER INFORMATION: Synthetic Construct

<400> SEQUENCE: 35

Ser Arg Tyr Asp Gly Tyr Tyr Ala Ala Tyr
1               5                   10

<210> SEQ ID NO 36
<211> LENGTH: 7
<212> TYPE: PRT
<213> ORGANISM: Artificial Sequence
<220> FEATURE:
```

```
<223> OTHER INFORMATION: Synthetic Construct

<400> SEQUENCE: 36

Asp Asn Asp Tyr Phe Asp Tyr
1               5

<210> SEQ ID NO 37
<211> LENGTH: 12
<212> TYPE: PRT
<213> ORGANISM: Artificial Sequence
<220> FEATURE:
<223> OTHER INFORMATION: Synthetic Construct

<400> SEQUENCE: 37

Ser Tyr Tyr Gly Asn Tyr Glu Gly Tyr Leu Asp Val
1               5                   10

<210> SEQ ID NO 38
<211> LENGTH: 9
<212> TYPE: PRT
<213> ORGANISM: Artificial Sequence
<220> FEATURE:
<223> OTHER INFORMATION: Synthetic Construct

<400> SEQUENCE: 38

Gly Asp Gly Asn Trp Tyr Phe Asp Val
1               5

<210> SEQ ID NO 39
<211> LENGTH: 5
<212> TYPE: PRT
<213> ORGANISM: Artificial Sequence
<220> FEATURE:
<223> OTHER INFORMATION: Synthetic Construct

<400> SEQUENCE: 39

Thr Phe Ile Thr Gly
1               5

<210> SEQ ID NO 40
<211> LENGTH: 10
<212> TYPE: PRT
<213> ORGANISM: Artificial Sequence
<220> FEATURE:
<223> OTHER INFORMATION: Synthetic Construct

<400> SEQUENCE: 40

Ala Tyr Gly Asn Ser Ala Trp Phe Ala Tyr
1               5                   10

<210> SEQ ID NO 41
<211> LENGTH: 4
<212> TYPE: PRT
<213> ORGANISM: Artificial Sequence
<220> FEATURE:
<223> OTHER INFORMATION: Synthetic Construct

<400> SEQUENCE: 41

Ser Met Asp Tyr
1

<210> SEQ ID NO 42
<211> LENGTH: 11
<212> TYPE: PRT
<213> ORGANISM: Artificial Sequence
<220> FEATURE:
<223> OTHER INFORMATION: Synthetic Construct
```

```
<400> SEQUENCE: 42

Gly Tyr Gly Ser Ser Tyr Glu Tyr Phe Asp Val
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Synthetic Construct

<400> SEQUENCE: 43

His Ile Tyr Tyr Gly Asn Leu Tyr Tyr Ala Met Asp Tyr
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Synthetic Construct

<400> SEQUENCE: 44

His Arg Gly Asn Tyr Pro Tyr Tyr Thr Met Asp Tyr
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Synthetic Construct

<400> SEQUENCE: 45

Gly Ser Val Tyr Gly Asn Trp Phe Pro Tyr
1               5                   10

<210> SEQ ID NO 46
<211> LENGTH: 16
<212> TYPE: PRT
<213> ORGANISM: Artificial Sequence
<220> FEATURE:
<223> OTHER INFORMATION: Synthetic Construct

<400> SEQUENCE: 46

Arg Ser Ser Lys Ser Leu Leu His Ser Asn Gly Ile Thr Tyr Leu Tyr
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Synthetic Construct

<400> SEQUENCE: 47

Arg Ala Ser Glu Ser Val Asp Asn Tyr Gly Val Ser Phe Met Asn
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: Synthetic Construct
```

```
<400> SEQUENCE: 48

Lys Ser Ser Gln Ser Leu Leu Asp Ser Asp Gly Lys Thr Tyr Leu Ser
1               5                   10                  15

<210> SEQ ID NO 49
<211> LENGTH: 11
<212> TYPE: PRT
<213> ORGANISM: Artificial Sequence
<220> FEATURE:
<223> OTHER INFORMATION: Synthetic Construct

<400> SEQUENCE: 49

Arg Ala Ser Asp His Ile His Asn Trp Leu Ala
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Synthetic Construct

<400> SEQUENCE: 50

Arg Ala Ser Gln Ser Ile Ser Asp Asn Leu His
1               5                   10

<210> SEQ ID NO 51
<211> LENGTH: 15
<212> TYPE: PRT
<213> ORGANISM: Artificial Sequence
<220> FEATURE:
<223> OTHER INFORMATION: Synthetic Construct

<400> SEQUENCE: 51

Arg Ala Ser Glu Ser Val Glu Ser Tyr Gly Lys Ser Phe Ile His
1               5                   10                  15

<210> SEQ ID NO 52
<211> LENGTH: 17
<212> TYPE: PRT
<213> ORGANISM: Artificial Sequence
<220> FEATURE:
<223> OTHER INFORMATION: Synthetic Construct

<400> SEQUENCE: 52

Lys Ser Ser Gln Ser Leu Leu Asn Ser Gly Asp Gln Glu Asn Tyr Leu
1               5                   10                  15

Val

<210> SEQ ID NO 53
<211> LENGTH: 16
<212> TYPE: PRT
<213> ORGANISM: Artificial Sequence
<220> FEATURE:
<223> OTHER INFORMATION: Synthetic Construct

<400> SEQUENCE: 53

Arg Ser Ser Gln Thr Ile Val His Ser Asp Gly Asn Thr Tyr Leu Glu
1               5                   10                  15

<210> SEQ ID NO 54
<211> LENGTH: 10
<212> TYPE: PRT
<213> ORGANISM: Artificial Sequence
<220> FEATURE:
<223> OTHER INFORMATION: Synthetic Construct
```

```
<400> SEQUENCE: 54

Arg Ala Ser Ser Ser Val Ser Tyr Met His
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Synthetic Construct

<400> SEQUENCE: 55

Lys Ala Ser Glu Asn Val Gly Thr Tyr Val Ser
1               5                   10

<210> SEQ ID NO 56
<211> LENGTH: 15
<212> TYPE: PRT
<213> ORGANISM: Artificial Sequence
<220> FEATURE:
<223> OTHER INFORMATION: Synthetic Construct

<400> SEQUENCE: 56

Arg Ala Ser Glu Ser Val Asp Ser Tyr Gly Asn Ser Phe Met His
1               5                   10                  15

<210> SEQ ID NO 57
<211> LENGTH: 16
<212> TYPE: PRT
<213> ORGANISM: Artificial Sequence
<220> FEATURE:
<223> OTHER INFORMATION: Synthetic Construct

<400> SEQUENCE: 57

Arg Ser Ser Gln Ser Ile Ile His Asn Asn Gly Asn Thr Tyr Leu Glu
1               5                   10                  15

<210> SEQ ID NO 58
<211> LENGTH: 11
<212> TYPE: PRT
<213> ORGANISM: Artificial Sequence
<220> FEATURE:
<223> OTHER INFORMATION: Synthetic Construct

<400> SEQUENCE: 58

Arg Ala Ser Gln Asp Ile Ser Asn Tyr Leu Asn
1               5                   10

<210> SEQ ID NO 59
<211> LENGTH: 16
<212> TYPE: PRT
<213> ORGANISM: Artificial Sequence
<220> FEATURE:
<223> OTHER INFORMATION: Synthetic Construct

<400> SEQUENCE: 59

Arg Ser Ser Lys Ser Leu Leu His Ser Asp Gly Asn Thr Tyr Leu Tyr
1               5                   10                  15

<210> SEQ ID NO 60
<211> LENGTH: 17
<212> TYPE: PRT
<213> ORGANISM: Artificial Sequence
<220> FEATURE:
<223> OTHER INFORMATION: Synthetic Construct
```

```
<400> SEQUENCE: 60

Lys Ser Ser Gln Ser Leu Phe Asn Ser Arg Thr Arg Lys Asn Tyr Leu
1               5                   10                  15
Thr

<210> SEQ ID NO 61
<211> LENGTH: 7
<212> TYPE: PRT
<213> ORGANISM: Artificial Sequence
<220> FEATURE:
<223> OTHER INFORMATION: Synthetic Construct

<400> SEQUENCE: 61

Gln Met Ser Asn Leu Ala Ser
1               5

<210> SEQ ID NO 62
<211> LENGTH: 7
<212> TYPE: PRT
<213> ORGANISM: Artificial Sequence
<220> FEATURE:
<223> OTHER INFORMATION: Synthetic Construct

<400> SEQUENCE: 62

Ala Ala Ser Asn Gln Gly Ser
1               5

<210> SEQ ID NO 63
<211> LENGTH: 7
<212> TYPE: PRT
<213> ORGANISM: Artificial Sequence
<220> FEATURE:
<223> OTHER INFORMATION: Synthetic Construct

<400> SEQUENCE: 63

Leu Met Ser Lys Leu Asp Ser
1               5

<210> SEQ ID NO 64
<211> LENGTH: 7
<212> TYPE: PRT
<213> ORGANISM: Artificial Sequence
<220> FEATURE:
<223> OTHER INFORMATION: Synthetic Construct

<400> SEQUENCE: 64

Gly Ala Thr Ser Leu Glu Thr
1               5

<210> SEQ ID NO 65
<211> LENGTH: 7
<212> TYPE: PRT
<213> ORGANISM: Artificial Sequence
<220> FEATURE:
<223> OTHER INFORMATION: Synthetic Construct

<400> SEQUENCE: 65

Tyr Ala Ser Gln Ser Ile Ser
1               5

<210> SEQ ID NO 66
<211> LENGTH: 7
<212> TYPE: PRT
<213> ORGANISM: Artificial Sequence
<220> FEATURE:
<223> OTHER INFORMATION: Synthetic Construct
```

```
<400> SEQUENCE: 66

Leu Ala Ser Asn Leu Glu Ser
1               5

<210> SEQ ID NO 67
<211> LENGTH: 7
<212> TYPE: PRT
<213> ORGANISM: Artificial Sequence
<220> FEATURE:
<223> OTHER INFORMATION: Synthetic Construct

<400> SEQUENCE: 67

Gly Ala Ser Thr Arg Glu Ser
1               5

<210> SEQ ID NO 68
<211> LENGTH: 7
<212> TYPE: PRT
<213> ORGANISM: Artificial Sequence
<220> FEATURE:
<223> OTHER INFORMATION: Synthetic Construct

<400> SEQUENCE: 68

Thr Val Ser Asn Arg Phe Ser
1               5

<210> SEQ ID NO 69
<211> LENGTH: 7
<212> TYPE: PRT
<213> ORGANISM: Artificial Sequence
<220> FEATURE:
<223> OTHER INFORMATION: Synthetic Construct

<400> SEQUENCE: 69

Ala Thr Ser Asn Leu Ala Ser
1               5

<210> SEQ ID NO 70
<211> LENGTH: 7
<212> TYPE: PRT
<213> ORGANISM: Artificial Sequence
<220> FEATURE:
<223> OTHER INFORMATION: Synthetic Construct

<400> SEQUENCE: 70

Lys Val Ser Ile Arg Phe Ser
1               5

<210> SEQ ID NO 71
<211> LENGTH: 7
<212> TYPE: PRT
<213> ORGANISM: Artificial Sequence
<220> FEATURE:
<223> OTHER INFORMATION: Synthetic Construct

<400> SEQUENCE: 71

Gly Ala Ser Asn Arg Tyr Thr
1               5

<210> SEQ ID NO 72
<211> LENGTH: 7
<212> TYPE: PRT
<213> ORGANISM: Artificial Sequence
<220> FEATURE:
<223> OTHER INFORMATION: Synthetic Construct
```

```
<400> SEQUENCE: 72

Arg Ala Ser Asn Leu Glu Ser
1               5

<210> SEQ ID NO 73
<211> LENGTH: 7
<212> TYPE: PRT
<213> ORGANISM: Artificial Sequence
<220> FEATURE:
<223> OTHER INFORMATION: Synthetic Construct

<400> SEQUENCE: 73

Lys Val Ser Asn Arg Phe Ser
1               5

<210> SEQ ID NO 74
<211> LENGTH: 7
<212> TYPE: PRT
<213> ORGANISM: Artificial Sequence
<220> FEATURE:
<223> OTHER INFORMATION: Synthetic Construct

<400> SEQUENCE: 74

Tyr Thr Ser Val Leu His Ser
1               5

<210> SEQ ID NO 75
<211> LENGTH: 7
<212> TYPE: PRT
<213> ORGANISM: Artificial Sequence
<220> FEATURE:
<223> OTHER INFORMATION: Synthetic Construct

<400> SEQUENCE: 75

Arg Met Ser Asn Leu Ala Pro
1               5

<210> SEQ ID NO 76
<211> LENGTH: 7
<212> TYPE: PRT
<213> ORGANISM: Artificial Sequence
<220> FEATURE:
<223> OTHER INFORMATION: Synthetic Construct

<400> SEQUENCE: 76

Trp Ala Ser Thr Arg Glu Ser
1               5

<210> SEQ ID NO 77
<211> LENGTH: 9
<212> TYPE: PRT
<213> ORGANISM: Artificial Sequence
<220> FEATURE:
<223> OTHER INFORMATION: Synthetic Construct

<400> SEQUENCE: 77

Ala Gln Asn Leu Glu Leu Pro Trp Thr
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic Construct

<400> SEQUENCE: 78
```

```
Gln Gln Ser Lys Glu Val Pro Trp Thr
1               5
```

<210> SEQ ID NO 79
<211> LENGTH: 9
<212> TYPE: PRT
<213> ORGANISM: Artificial Sequence
<220> FEATURE:
<223> OTHER INFORMATION: Synthetic Construct

<400> SEQUENCE: 79

```
Trp Gln Gly Thr His Phe Pro Gln Thr
1               5
```

<210> SEQ ID NO 80
<211> LENGTH: 9
<212> TYPE: PRT
<213> ORGANISM: Artificial Sequence
<220> FEATURE:
<223> OTHER INFORMATION: Synthetic Construct

<400> SEQUENCE: 80

```
Gln His Tyr Trp Ser Ile Pro Trp Thr
1               5
```

<210> SEQ ID NO 81
<211> LENGTH: 9
<212> TYPE: PRT
<213> ORGANISM: Artificial Sequence
<220> FEATURE:
<223> OTHER INFORMATION: Synthetic Construct

<400> SEQUENCE: 81

```
Gln Gln Ser Asn Ser Trp Pro Tyr Thr
1               5
```

<210> SEQ ID NO 82
<211> LENGTH: 9
<212> TYPE: PRT
<213> ORGANISM: Artificial Sequence
<220> FEATURE:
<223> OTHER INFORMATION: Synthetic Construct

<400> SEQUENCE: 82

```
Gln Gln Asn Asn Val Gly Pro Tyr Thr
1               5
```

<210> SEQ ID NO 83
<211> LENGTH: 9
<212> TYPE: PRT
<213> ORGANISM: Artificial Sequence
<220> FEATURE:
<223> OTHER INFORMATION: Synthetic Construct

<400> SEQUENCE: 83

```
Gln Ser Asp His Ser Tyr Pro Leu Thr
1               5
```

<210> SEQ ID NO 84
<211> LENGTH: 9
<212> TYPE: PRT
<213> ORGANISM: Artificial Sequence
<220> FEATURE:
<223> OTHER INFORMATION: Synthetic Construct

<400> SEQUENCE: 84

```
Phe Gln Gly Ser His Val Pro Trp Thr
1               5

<210> SEQ ID NO 85
<211> LENGTH: 9
<212> TYPE: PRT
<213> ORGANISM: Artificial Sequence
<220> FEATURE:
<223> OTHER INFORMATION: Synthetic Construct

<400> SEQUENCE: 85

Gln Gln Trp Ser Ser Asn Pro Trp Thr
1               5

<210> SEQ ID NO 86
<211> LENGTH: 9
<212> TYPE: PRT
<213> ORGANISM: Artificial Sequence
<220> FEATURE:
<223> OTHER INFORMATION: Synthetic Construct

<400> SEQUENCE: 86

Gly Gln Thr Tyr Ser Phe Pro Tyr Thr
1               5

<210> SEQ ID NO 87
<211> LENGTH: 9
<212> TYPE: PRT
<213> ORGANISM: Artificial Sequence
<220> FEATURE:
<223> OTHER INFORMATION: Synthetic Construct

<400> SEQUENCE: 87

Gln Gln Ser Asn Glu Asp Pro Leu Thr
1               5

<210> SEQ ID NO 88
<211> LENGTH: 9
<212> TYPE: PRT
<213> ORGANISM: Artificial Sequence
<220> FEATURE:
<223> OTHER INFORMATION: Synthetic Construct

<400> SEQUENCE: 88

Gln Gln Gly Asn Thr Leu Pro Trp Thr
1               5

<210> SEQ ID NO 89
<211> LENGTH: 9
<212> TYPE: PRT
<213> ORGANISM: Artificial Sequence
<220> FEATURE:
<223> OTHER INFORMATION: Synthetic Construct

<400> SEQUENCE: 89

Met Gln His Leu Glu Phe Pro Phe Ile
1               5

<210> SEQ ID NO 90
<211> LENGTH: 8
<212> TYPE: PRT
<213> ORGANISM: Artificial Sequence
<220> FEATURE:
<223> OTHER INFORMATION: Synthetic Construct

<400> SEQUENCE: 90

Lys Gln Ser Tyr Asn Leu Leu Thr
```

<210> SEQ ID NO 91
<211> LENGTH: 115
<212> TYPE: PRT
<213> ORGANISM: Artificial Sequence
<220> FEATURE:
<223> OTHER INFORMATION: Synthetic Construct

<400> SEQUENCE: 91

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Met His Trp Val Lys Gln Ser Pro Glu Asp Ser Leu Glu Trp Ile
        35                  40                  45

Gly Ala Ile Asn Pro Ser Thr Gly Ser Thr Tyr Ser Gln Lys Phe
    50                  55                  60

Lys Asp Lys Ala Thr Leu Thr Val Asp Lys Ser Ser Thr Ala Tyr
65                  70                  75                  80

Met Gln Leu Lys Ser Leu Thr Ser Glu Glu Ser Ala Val Tyr Tyr Cys
            85                  90                  95

Thr Arg Phe Asp Gly Tyr Gly Tyr Trp Gly Gln Gly Thr Leu Val Thr
            100                 105                 110

Val Ser Ala
        115

<210> SEQ ID NO 92
<211> LENGTH: 115
<212> TYPE: PRT
<213> ORGANISM: Artificial Sequence
<220> FEATURE:
<223> OTHER INFORMATION: Synthetic Construct

<400> SEQUENCE: 92

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Leu Gly Tyr Ile Thr Tyr Asp Gly Asp Thr Tyr Asn Pro Ser Leu
    50                  55                  60

Lys Asn Arg Val Ser Ile Thr Arg Asp Thr Ser Lys Asn Gln Phe Phe
65                  70                  75                  80

Leu Asn Leu Ile Ser Val Thr Pro Glu Asp Thr Ala Thr Tyr Tyr Cys
            85                  90                  95

Ala Arg Glu Asp Ser Phe Gly Tyr Trp Gly Gln Gly Thr Leu Val Thr
            100                 105                 110

Val Ser Ala
        115

<210> SEQ ID NO 93
<211> LENGTH: 115
<212> TYPE: PRT
<213> ORGANISM: Artificial Sequence
<220> FEATURE:
<223> OTHER INFORMATION: Synthetic Construct

<400> SEQUENCE: 93

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Phe Met Lys Trp Val Lys Gln Ser His Gly Lys Ser Leu Glu Trp Ile
        35                  40                  45

Gly Asp Ile Asn Pro Lys Asn Gly Asp Thr Phe Tyr Asn Gln Lys Phe
    50                  55                  60

Lys Gly Lys Ala Thr Leu Thr Val Asp Lys Ser Ser Thr Ala Tyr
65                  70                  75                  80

Met Gln Leu Asn Ser Leu Thr Ser Glu Asp Ser Ala Val Tyr Tyr Cys
            85                  90                  95

Ala Arg Pro Gly Tyr Phe Asp Val Trp Gly Ala Gly Thr Thr Val Thr
            100                 105                 110

Val Ser Ser
        115

<210> SEQ ID NO 94
<211> LENGTH: 115
<212> TYPE: PRT
<213> ORGANISM: Artificial Sequence
<220> FEATURE:
<223> OTHER INFORMATION: Synthetic Construct

<400> SEQUENCE: 94

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Met His Trp Val Lys Gln Ser Pro Glu Asp Ser Leu Glu Trp Ile
        35                  40                  45

Gly Ala Ile Asn Pro Ser Thr Gly Gly Ser Thr Tyr Ser Gln Lys Phe
    50                  55                  60

Lys Asp Lys Ala Thr Leu Thr Val Asp Lys Ser Ser Ser Thr Ala Tyr
65                  70                  75                  80

Met Gln Leu Lys Ser Leu Thr Ser Glu Glu Ser Ala Val Tyr Tyr Cys
            85                  90                  95

Thr Arg Phe Asp Gly Tyr Gly Tyr Trp Gly Gln Gly Thr Leu Val Thr
            100                 105                 110

Val Ser Ala
        115

<210> SEQ ID NO 95
<211> LENGTH: 116
<212> TYPE: PRT
<213> ORGANISM: Artificial Sequence
<220> FEATURE:
<223> OTHER INFORMATION: Synthetic Construct

<400> SEQUENCE: 95

Gln Ile Gln Leu Val Gln Ser Gly Pro Glu Leu Lys Lys Pro Gly Glu
1               5                   10                  15

Ser Val Lys Ile Ser Cys Lys Ala Ser Gly Tyr Thr Phe Ala Asn Tyr
            20                  25                  30

Gly Met Asn Trp Val Lys Leu Ala Pro Gly Lys Gly Leu Lys Trp Met
        35                  40                  45

Gly Tyr Ile Asn Ile Tyr Ser Gly Lys Ser Arg Tyr Ala Asp Asp Phe

```
                50                  55                  60
Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Met Ala Thr Tyr Phe Cys
                    85                  90                  95

Ala Arg Asp Asn Asp Tyr Phe Asp Tyr Trp Gly Gln Gly Thr Thr Leu
                100                 105                 110

Thr Val Ser Ser
        115

<210> SEQ ID NO 96
<211> LENGTH: 121
<212> TYPE: PRT
<213> ORGANISM: Artificial Sequence
<220> FEATURE:
<223> OTHER INFORMATION: Synthetic Construct

<400> SEQUENCE: 96

Gln Val Gln Leu Gln Gln Ser Gly Ala Glu Leu Ala Arg Pro Gly Ala
 1               5                  10                  15

Ser Val Lys Met Ser Cys Lys Ala Ser Gly Tyr Thr Phe Thr Ser Tyr
                20                  25                  30

Ala Met His Trp Val Lys Gln Arg Pro Gly Gln Gly Leu Glu Trp Ile
            35                  40                  45

Gly Tyr Ile Asn Pro Ser Ser Gly Tyr Thr Tyr Tyr Asn Gln Lys Phe
        50                  55                  60

Lys Asp Lys Ala Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Tyr Cys
                85                  90                  95

Ala Arg Ser Tyr Tyr Gly Asn Tyr Glu Gly Tyr Leu Asp Val Trp Gly
                100                 105                 110

Ala Gly Thr Thr Val Thr Val Ser Ser
        115                 120

<210> SEQ ID NO 97
<211> LENGTH: 118
<212> TYPE: PRT
<213> ORGANISM: Artificial Sequence
<220> FEATURE:
<223> OTHER INFORMATION: Synthetic Construct

<400> SEQUENCE: 97

Gln Val Gln Leu Gln Gln Ser Gly Ala Glu Leu Ala Arg Pro Gly Thr
 1               5                  10                  15

Ser Val Lys Leu Ser Cys Lys Ala Ser Gly Tyr Thr Phe Thr Asp Tyr
                20                  25                  30

Tyr Ile Asn Trp Val Lys Gln Arg Asn Gly Gln Gly Leu Glu Trp Ile
            35                  40                  45

Gly Glu Ile Tyr Pro Arg Ser Gly Asn Ala Tyr Tyr Asn Glu Lys Phe
        50                  55                  60

Arg Gly Lys Ala Thr Leu Thr Thr Asp Lys Ser Ser Ser Thr Ala Tyr
 65                  70                  75                  80

Met Gln Leu Ser Gly Leu Thr Ser Glu Asp Ser Ala Val Tyr Phe Cys
                85                  90                  95

Ala Arg Gly Asp Gly Asn Trp Tyr Phe Asp Val Trp Gly Ala Gly Thr
                100                 105                 110
```

Thr Val Ile Val Ser Ser
         115

<210> SEQ ID NO 98
<211> LENGTH: 114
<212> TYPE: PRT
<213> ORGANISM: Artificial Sequence
<220> FEATURE:
<223> OTHER INFORMATION: Synthetic Construct

<400> SEQUENCE: 98

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Ile His Trp Val Lys Glu Ser His Val Lys Ser Leu Glu Trp Ile
        35                  40                  45

Gly Arg Ile Asn Pro Lys Asn Gly Val Thr Ser Tyr Asn Gln Asn Phe
    50                  55                  60

Lys Asp Lys Ala Ser Leu Thr Val Asp Arg Ser Ser Thr Ala Tyr
65                  70                  75                  80

Met Asp Leu Tyr Ser Leu Thr Ser Glu Asp Ser Ala Val Tyr Tyr Cys
                85                  90                  95

Ala Ser Thr Phe Ile Thr Gly Trp Gly Gln Gly Thr Ser Leu Thr Val
            100                 105                 110

Ser Ser

<210> SEQ ID NO 99
<211> LENGTH: 119
<212> TYPE: PRT
<213> ORGANISM: Artificial Sequence
<220> FEATURE:
<223> OTHER INFORMATION: Synthetic Construct

<400> SEQUENCE: 99

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Ala Tyr Gly Asn Ser Ala Trp Phe Ala Tyr Trp Gly Gln Gly
            100                 105                 110

Thr Leu Val Thr Val Ser Ala
        115

<210> SEQ ID NO 100
<211> LENGTH: 114
<212> TYPE: PRT
<213> ORGANISM: Artificial Sequence
<220> FEATURE:
<223> OTHER INFORMATION: Synthetic Construct

<400> SEQUENCE: 100

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Ser Phe Thr Gly Tyr
                20                  25                  30

Tyr Ile His Trp Val Lys Gln Ser His Ile Lys Ser Leu Glu Trp Ile
            35                  40                  45

Gly Arg Ile Asn Pro Asn Asn Gly Ala Thr Asn Tyr Asn Gln Ile Phe
        50                  55                  60

Lys Asp Lys Ala Thr Leu Thr Val Asp Arg Ser Ser Thr Ala Tyr
65                  70                  75                  80

Met Asp Leu His Ser Leu Thr Ser Glu Asp Ser Ala Val Tyr Tyr Cys
            85                  90                  95

Val Ser Thr Phe Ile Thr Gly Trp Gly Gln Gly Thr Thr Leu Thr Val
            100                 105                 110

Ser Ser

<210> SEQ ID NO 101
<211> LENGTH: 115
<212> TYPE: PRT
<213> ORGANISM: Artificial Sequence
<220> FEATURE:
<223> OTHER INFORMATION: Synthetic Construct

<400> SEQUENCE: 101

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
                20                  25                  30

Tyr Met His Trp Val Lys Gln Ser Pro Glu Asp Ser Leu Glu Trp Ile
            35                  40                  45

Gly Ala Ile Asn Pro Ser Thr Gly Gly Ser Tyr Ser Gln Lys Phe
        50                  55                  60

Lys Asp Lys Ala Thr Leu Thr Val Asp Lys Ser Ser Ser Thr Ala Tyr
65                  70                  75                  80

Met Gln Leu Lys Ser Leu Thr Ser Glu Glu Ser Ala Val Tyr Tyr Cys
            85                  90                  95

Thr Arg Phe Asp Gly Tyr Gly Tyr Trp Gly Gln Gly Thr Leu Val Thr
            100                 105                 110

Val Ser Ser
        115

<210> SEQ ID NO 102
<211> LENGTH: 115
<212> TYPE: PRT
<213> ORGANISM: Artificial Sequence
<220> FEATURE:
<223> OTHER INFORMATION: Synthetic Construct

<400> SEQUENCE: 102

Glu Val Lys Val Val Glu Ser Gly Gly Gly Leu Val Gln Pro Gly Gly
1               5                   10                  15

Ser Leu Arg Leu Ser Cys Ala Thr Ala Gly Phe Thr Phe Thr Asp Tyr
                20                  25                  30

Tyr Met Thr Trp Val Arg Gln Pro Pro Gly Lys Ala Leu Glu Trp Leu
            35                  40                  45

Gly Phe Ile Arg Asn Lys Ala Asn Gly Tyr Thr Thr Glu Tyr Asn Ser
        50                  55                  60

```
Ser Val Lys Gly Arg Phe Thr Ile Ser Arg Asp Asn Ser Arg Ser Ile
 65                  70                  75                  80

Leu Tyr Leu Gln Met Asn Thr Leu Arg Ala Glu Asp Ser Ala Thr Tyr
             85                  90                  95

Tyr Cys Ala Arg Ser Met Asp Tyr Trp Gly Gln Gly Thr Ser Val Thr
            100                 105                 110

Val Ser Ser
        115

<210> SEQ ID NO 103
<211> LENGTH: 119
<212> TYPE: PRT
<213> ORGANISM: Artificial Sequence
<220> FEATURE:
<223> OTHER INFORMATION: Synthetic Construct

<400> SEQUENCE: 103

Gln Val Gln Leu Lys Gln Ser Gly Pro Gly Leu Val Gln Pro Ser Gln
 1               5                  10                  15

Ser Leu Ser Ile Thr Cys Thr Val Ser Gly Phe Ser Leu Thr Thr Tyr
             20                  25                  30

Gly Val His Trp Val Arg Gln Ser Pro Gly Lys Gly Leu Glu Trp Leu
             35                  40                  45

Gly Val Ile Trp Ser Gly Gly Ser Thr Asp Tyr Asn Ala Ala Phe Ile
         50                  55                  60

Ser Arg Leu Asn Ile Ser Lys Asp Asn Ser Lys Ser Gln Val Phe Phe
 65                  70                  75                  80

Lys Met Asn Ser Leu Gln Ala Asn Asp Thr Ala Ile Tyr Tyr Cys Ala
             85                  90                  95

Arg Gly Tyr Gly Ser Ser Tyr Glu Tyr Phe Asp Val Trp Gly Ala Gly
            100                 105                 110

Thr Thr Val Thr Val Ser Ser
        115

<210> SEQ ID NO 104
<211> LENGTH: 122
<212> TYPE: PRT
<213> ORGANISM: Artificial Sequence
<220> FEATURE:
<223> OTHER INFORMATION: Synthetic Construct

<400> SEQUENCE: 104

Glu Val Met Leu Val Glu Ser Gly Gly Gly Leu Val Lys Pro Gly Gly
 1               5                  10                  15

Ser Leu Lys Leu Ser Cys Ala Ala Ser Gly Phe Thr Phe Ser Ser His
             20                  25                  30

Ala Met Ser Trp Val Arg Gln Thr Pro Glu Lys Arg Leu Glu Trp Val
             35                  40                  45

Ala Thr Ile Ser Ser Gly Asp Ser Tyr Thr Tyr Tyr Pro Asp Ser Val
         50                  55                  60

Lys Gly Arg Phe Thr Ile Ser Arg Asp Asn Ala Lys Asn Thr Leu Tyr
 65                  70                  75                  80

Leu Gln Met Thr Ser Leu Arg Ser Glu Asp Thr Ala Met Tyr Tyr Cys
             85                  90                  95

Ile Arg His Ile Tyr Tyr Gly Asn Leu Tyr Tyr Ala Met Asp Tyr Trp
            100                 105                 110

Gly Gln Gly Thr Ser Val Thr Val Ser Ser
```

<210> SEQ ID NO 105
<211> LENGTH: 114
<212> TYPE: PRT
<213> ORGANISM: Artificial Sequence
<220> FEATURE:
<223> OTHER INFORMATION: Synthetic Construct

<400> SEQUENCE: 105

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Ile His Trp Val Lys Glu Ser His Val Lys Ser Leu Glu Trp Ile
        35                  40                  45

Gly Arg Ile Asn Pro Lys Asn Gly Val Thr Ser Tyr Asn Gln Asn Phe
    50                  55                  60

Lys Asp Lys Ala Ser Leu Thr Val Asp Arg Ser Ser Thr Ala Tyr
65                  70                  75                  80

Met Asp Leu Tyr Ser Leu Thr Ser Glu Asp Ser Ala Val Tyr Tyr Cys
                85                  90                  95

Ala Ser Thr Phe Ile Thr Gly Trp Gly Gln Gly Thr Thr Val Thr Val
            100                 105                 110

Ser Ser

<210> SEQ ID NO 106
<211> LENGTH: 120
<212> TYPE: PRT
<213> ORGANISM: Artificial Sequence
<220> FEATURE:
<223> OTHER INFORMATION: Synthetic Construct

<400> SEQUENCE: 106

Gln Val Gln Leu Lys Glu Ser Gly Pro Gly Leu Val Ala Pro Ser Gln
1               5                   10                  15

Ser Leu Ser Ile Thr Cys Thr Ile Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Val Val Ile Trp Ser Asp Gly Ser Thr Thr Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Gly Leu Gln Thr Asp Asp Thr Ala Met Tyr Tyr Cys Ala
                85                  90                  95

Arg His Arg Gly Asn Tyr Pro Tyr Tyr Thr Met Asp Tyr Trp Gly Gln
            100                 105                 110

Gly Thr Ser Val Thr Val Ser Ser
        115                 120

<210> SEQ ID NO 107
<211> LENGTH: 121
<212> TYPE: PRT
<213> ORGANISM: Artificial Sequence
<220> FEATURE:
<223> OTHER INFORMATION: Synthetic Construct

<400> SEQUENCE: 107

```
Glu Val Asn Leu Glu Glu Ser Gly Gly Asp Leu Val Gln Pro Gly Gly
1               5                   10                  15

Ser Met Lys Leu Ser Cys Leu Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Lys Asn Lys Ala Asn Asn Tyr Val Thr Phe Tyr Ala Ala
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Pro Glu Asp Thr Gly Ile Tyr
                85                  90                  95

Phe Cys Thr Arg Gly Ser Val Tyr Gly Asn Trp Phe Pro Tyr Trp Gly
                100                 105                 110

Gln Gly Thr Leu Val Thr Val Ser Ala
            115                 120
```

<210> SEQ ID NO 108
<211> LENGTH: 121
<212> TYPE: PRT
<213> ORGANISM: Artificial Sequence
<220> FEATURE:
<223> OTHER INFORMATION: Synthetic Construct

<400> SEQUENCE: 108

```
Glu Val Asn Leu Glu Glu Ser Gly Gly Asp Leu Val Gln Pro Gly Gly
1               5                   10                  15

Ser Met Lys Leu Ser Cys Leu Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Lys Asn Lys Ala Asn Asn Tyr Val Thr Phe Tyr Ala Ala
    50                  55                  60

Ser Val Lys Gly Arg Phe Thr Ile Ser Arg Asp Asp Ser Lys Ser Ser
65                  70                  75                  80

Val Tyr Leu Gln Met Asn Ser Leu Arg Leu Glu Asp Thr Gly Ile Tyr
                85                  90                  95

Phe Cys Thr Arg Gly Ser Val Tyr Gly Asn Trp Phe Pro Tyr Trp Gly
                100                 105                 110

Gln Gly Thr Leu Val Thr Val Ser Ala
            115                 120
```

<210> SEQ ID NO 109
<211> LENGTH: 112
<212> TYPE: PRT
<213> ORGANISM: Artificial Sequence
<220> FEATURE:
<223> OTHER INFORMATION: Synthetic Construct

<400> SEQUENCE: 109

```
Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Leu Gln Leu Leu Ile Tyr Gln Met Ser Asn Leu Ala Ser Gly Val Pro
    50                  55                  60
```

Asp Arg Phe Ser Gly Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Leu Glu Ile Lys
            100                 105                 110

<210> SEQ ID NO 110
<211> LENGTH: 111
<212> TYPE: PRT
<213> ORGANISM: Artificial Sequence
<220> FEATURE:
<223> OTHER INFORMATION: Synthetic Construct

<400> SEQUENCE: 110

Asp Ile Val Leu Thr Gln Ser Pro Ala Ser Leu Thr Val Ser Leu Gly
1               5                   10                  15

Gln Arg Ala Thr Ile Ser Cys Arg Ala Ser Glu Ser Val Asp Asn Tyr
            20                  25                  30

Gly Val Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Glu Asp Thr Ala Met Tyr Phe Cys Gln Gln Ser Lys
                85                  90                  95

Glu Val Pro Trp Thr Phe Gly Gly Gly Thr Lys Leu Glu Ile Lys
            100                 105                 110

<210> SEQ ID NO 111
<211> LENGTH: 112
<212> TYPE: PRT
<213> ORGANISM: Artificial Sequence
<220> FEATURE:
<223> OTHER INFORMATION: Synthetic Construct

<400> SEQUENCE: 111

Asp Val Val Met Thr Gln Ala Pro Leu Ile Leu Ser Ile Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Ser Trp Leu Leu Gln Arg Pro Gly Gln Ser
        35                  40                  45

Pro Lys Arg Leu Ile Tyr Leu Met Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110

<210> SEQ ID NO 112
<211> LENGTH: 107
<212> TYPE: PRT
<213> ORGANISM: Artificial Sequence
<220> FEATURE:
<223> OTHER INFORMATION: Synthetic Construct

<400> SEQUENCE: 112

Asp Ile Gln Met Thr Gln Ser Ser Ser Tyr Leu Ser Val Ser Leu Gly
1               5                   10                  15

Gly Arg Val Thr Ile Thr Cys Arg Ala Ser Asp His Ile His Asn Trp
            20                  25                  30

Leu Ala Trp Tyr Gln Gln Lys Pro Gly Asp Ala Pro Arg Leu Leu Ile
        35                  40                  45

Ser Gly Ala Thr Ser Leu Glu Thr Gly Val Pro Ser Arg Phe Ser Gly
50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln His Tyr Trp Ser Ile Pro Trp
                85                  90                  95

Thr Phe Gly Gly Gly Thr Lys Leu Glu Ile Lys
            100                 105

<210> SEQ ID NO 113
<211> LENGTH: 107
<212> TYPE: PRT
<213> ORGANISM: Artificial Sequence
<220> FEATURE:
<223> OTHER INFORMATION: Synthetic Construct

<400> SEQUENCE: 113

Asp Ile Val Leu Thr Gln Ser Pro Ala Thr Leu Ser Val Thr Pro Gly
1               5                   10                  15

Asp Thr Val Ser Leu Ser Cys Arg Ala Ser Gln Ser Ile Ser Asp Asn
            20                  25                  30

Leu His Trp Tyr Gln Gln Lys Ser His Glu Ser Pro Gly Leu Leu Ile
        35                  40                  45

Lys Tyr Ala Ser Gln Ser Ile Ser Gly Ile Pro Ser Arg Phe Ser Gly
50                  55                  60

Arg Gly Ser Gly Thr Asp Phe Thr Leu Ser Ile Asn Ser Val Asp Ser
65                  70                  75                  80

Glu Asp Phe Gly Val Tyr Phe Cys Gln Gln Ser Asn Ser Trp Pro Tyr
                85                  90                  95

Thr Phe Gly Gly Gly Thr Lys Leu Glu Ile Lys
            100                 105

<210> SEQ ID NO 114
<211> LENGTH: 111
<212> TYPE: PRT
<213> ORGANISM: Artificial Sequence
<220> FEATURE:
<223> OTHER INFORMATION: Synthetic Construct

<400> SEQUENCE: 114

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Ser Tyr
            20                  25                  30

Gly Lys Ser Phe Ile His Trp Tyr Gln Gln Lys Pro Gly Gln Pro Pro
        35                  40                  45

Lys Leu Leu Ile Phe Leu Ala Ser Asn Leu Glu Ser Gly Val Pro Ala
50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Val Gly Pro Tyr Thr Phe Gly Gly Gly Thr Lys Leu Glu Ile Lys
            100                 105                 110

<210> SEQ ID NO 115
<211> LENGTH: 113
<212> TYPE: PRT
<213> ORGANISM: Artificial Sequence
<220> FEATURE:
<223> OTHER INFORMATION: Synthetic Construct

<400> SEQUENCE: 115

Asp Ile Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
            20                  25                  30

Gly Asp Gln Glu Asn Tyr Leu Val Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Leu Ala Glu Asp Leu Ala Val Tyr Tyr Cys Gln Ser
                85                  90                  95

Asp His Ser Tyr Pro Leu Thr Phe Gly Ala Gly Thr Lys Leu Glu Leu
            100                 105                 110

Lys

<210> SEQ ID NO 116
<211> LENGTH: 112
<212> TYPE: PRT
<213> ORGANISM: Artificial Sequence
<220> FEATURE:
<223> OTHER INFORMATION: Synthetic Construct

<400> SEQUENCE: 116

Asp Val Leu Leu Thr Gln Ala Pro Leu Ser Leu Pro Val Ser Leu Gly
1               5                   10                  15

Asp Gln Ala Ser Ile Ser Cys Arg Ser Ser Gln Thr Ile Val His Ser
            20                  25                  30

Asp Gly Asn Thr Tyr Leu Glu Trp Tyr Leu Gln Lys Pro Gly Gln Ser
        35                  40                  45

Pro Lys Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 117
<211> LENGTH: 106
<212> TYPE: PRT
<213> ORGANISM: Artificial Sequence
<220> FEATURE:
<223> OTHER INFORMATION: Synthetic Construct

```
<400> SEQUENCE: 117

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Val Ser Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asn Pro Trp Thr
                85                  90                  95

Phe Gly Gly Gly Thr Lys Leu Glu Ile Lys
            100                 105

<210> SEQ ID NO 118
<211> LENGTH: 112
<212> TYPE: PRT
<213> ORGANISM: Artificial Sequence
<220> FEATURE:
<223> OTHER INFORMATION: Synthetic Construct

<400> SEQUENCE: 118

Asp Val Leu Leu Thr Gln Thr Pro Leu Ser Leu Pro Val Ser Leu Gly
1               5                   10                  15

Asp Gln Ala Ser Ile Ser Cys Arg Ser Ser Gln Thr Ile Val His Ser
            20                  25                  30

Asp Gly Asn Thr Tyr Leu Glu Trp Tyr Leu Gln Arg Pro Gly Leu Ser
        35                  40                  45

Pro Lys Leu Leu Ile Tyr Lys Val Ser Ile Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 119
<211> LENGTH: 107
<212> TYPE: PRT
<213> ORGANISM: Artificial Sequence
<220> FEATURE:
<223> OTHER INFORMATION: Synthetic Construct

<400> SEQUENCE: 119

Asn Ile Val Met Thr Gln Ser Pro Asn Ser Met Ser Met Ser Val Gly
1               5                   10                  15

Glu Arg Val Thr Leu Ser Cys Lys Ala Ser Glu Asn Val Gly Thr Tyr
            20                  25                  30

Val Ser Trp Tyr Gln Gln Lys Pro Asp Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Gly Gly Ser Ala Thr Asp Phe Thr Leu Thr Ile Ser Ser Val Gln Ala
65                  70                  75                  80
```

Glu Asp Leu Ala Asp Tyr His Cys Gly Gln Thr Tyr Ser Phe Pro Tyr
            85                  90                  95

Thr Phe Gly Gly Gly Thr Lys Leu Glu Ile Lys
            100                 105

<210> SEQ ID NO 120
<211> LENGTH: 111
<212> TYPE: PRT
<213> ORGANISM: Artificial Sequence
<220> FEATURE:
<223> OTHER INFORMATION: Synthetic Construct

<400> SEQUENCE: 120

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Leu Thr Phe Gly Ala Gly Thr Lys Leu Glu Leu Lys
            100                 105                 110

<210> SEQ ID NO 121
<211> LENGTH: 112
<212> TYPE: PRT
<213> ORGANISM: Artificial Sequence
<220> FEATURE:
<223> OTHER INFORMATION: Synthetic Construct

<400> SEQUENCE: 121

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Ile His Asn
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 122
<211> LENGTH: 107
<212> TYPE: PRT
<213> ORGANISM: Artificial Sequence
<220> FEATURE:
<223> OTHER INFORMATION: Synthetic Construct

<400> SEQUENCE: 122

Asp Ile Gln Met Thr Gln Thr Thr Ser Ser Leu Ser Ala Ser Leu Gly

```
                1               5              10              15

Asp Arg Val Thr Ile Ser Cys Arg Ala Ser Gln Asp Ile Ser Asn Tyr
                20                  25                  30

Leu Asn Trp Tyr Gln Gln Lys Pro Asp Gly Thr Val Lys Leu Leu Ile
            35                  40                  45

Tyr Tyr Thr Ser Val Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
                100                 105

<210> SEQ ID NO 123
<211> LENGTH: 112
<212> TYPE: PRT
<213> ORGANISM: Artificial Sequence
<220> FEATURE:
<223> OTHER INFORMATION: Synthetic Construct

<400> SEQUENCE: 123

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
                20                  25                  30

Asp Gly Asn Thr Tyr Leu Tyr Trp Phe Leu Gln Arg Pro Gly Gln Ser
            35                  40                  45

Pro Gln Leu Leu Ile Tyr Arg Met Ser Asn Leu Ala Pro Gly Val Pro
        50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Phe Pro Phe Ile Phe Gly Ala Gly Thr Lys Leu Glu Leu Lys
                100                 105                 110

<210> SEQ ID NO 124
<211> LENGTH: 112
<212> TYPE: PRT
<213> ORGANISM: Artificial Sequence
<220> FEATURE:
<223> OTHER INFORMATION: Synthetic Construct

<400> SEQUENCE: 124

Asp Val Val Met Thr Gln Ala Pro Leu Ile Leu Ser Ile Thr Ile Gly
1               5                   10                  15

Gln Pro Ala Ser Ile Ser Cys Lys Ser Ser Gln Ser Leu Leu Asp Ser
                20                  25                  30

Asp Gly Lys Thr Tyr Leu Ser Trp Leu Leu Gln Arg Pro Gly Arg Ser
            35                  40                  45

Pro Lys Arg Leu Ile Tyr Leu Met Ser Lys Leu Asp Ser Gly Val Pro
        50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95
```

```
Thr His Phe Pro Gln Thr Phe Gly Gly Gly Thr Lys Leu Glu Ile Lys
            100                 105                 110
```

<210> SEQ ID NO 125
<211> LENGTH: 112
<212> TYPE: PRT
<213> ORGANISM: Artificial Sequence
<220> FEATURE:
<223> OTHER INFORMATION: Synthetic Construct

<400> SEQUENCE: 125

```
Asp Ile Val Met Ser Gln Ser Pro Ser Ser Leu Ala Val Ser Ala Gly
1               5                   10                  15

Glu Lys Val Thr Met Thr Cys Lys Ser Ser Gln Ser Leu Phe Asn Ser
            20                  25                  30

Arg Thr Arg Lys Asn Tyr Leu Thr Trp Tyr Gln Gln Lys Pro Gly Gln
        35                  40                  45

Ser Pro Lys Val Leu Ile Tyr Trp Ala Ser Thr Arg Glu Ser Gly Val
    50                  55                  60

Pro Asp Arg Phe Thr Gly Ser Gly Ser Gly Thr Asp Phe Ser Leu Thr
65                  70                  75                  80

Ile Ser Ser Val Gln Ala Asp Asp Leu Ala Val Tyr Tyr Cys Lys Gln
                85                  90                  95

Ser Tyr Asn Leu Leu Thr Phe Gly Ala Gly Thr Arg Leu Glu Leu Lys
            100                 105                 110
```

<210> SEQ ID NO 126
<211> LENGTH: 112
<212> TYPE: PRT
<213> ORGANISM: Artificial Sequence
<220> FEATURE:
<223> OTHER INFORMATION: Synthetic Construct

<400> SEQUENCE: 126

```
Asp Ile Val Met Ser Gln Ser Pro Ser Ser Leu Ala Val Ser Ala Gly
1               5                   10                  15

Glu Lys Val Thr Met Thr Cys Lys Ser Ser Gln Ser Leu Phe Asn Ser
            20                  25                  30

Arg Thr Arg Lys Asn Tyr Leu Thr Trp Tyr Gln Gln Lys Pro Gly Gln
        35                  40                  45

Ser Pro Lys Val Leu Ile Tyr Trp Ala Ser Thr Arg Glu Ser Gly Val
    50                  55                  60

Pro Asp Arg Phe Thr Gly Ser Gly Ser Gly Thr Asp Phe Ser Leu Thr
65                  70                  75                  80

Ile Asn Ser Val Gln Ala Asp Asp Leu Ala Val Tyr Tyr Cys Lys Gln
                85                  90                  95

Ser Tyr Asn Leu Leu Thr Phe Gly Ala Gly Thr Lys Leu Glu Leu Lys
            100                 105                 110
```

<210> SEQ ID NO 127
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(1)
<223> OTHER INFORMATION: Xaa = Ser, Ile, Val, or Leu
<220> FEATURE:
<221> NAME/KEY: VARIANT
<222> LOCATION: (2)..(2)

```
<223> OTHER INFORMATION: Xaa = Any Amino Acid
<220> FEATURE:
<221> NAME/KEY: VARIANT
<222> LOCATION: (4)..(4)
<223> OTHER INFORMATION: Xaa = Any Amino Acid
<220> FEATURE:
<221> NAME/KEY: VARIANT
<222> LOCATION: (5)..(5)
<223> OTHER INFORMATION: Xaa = Any Amino Acid
<220> FEATURE:
<221> NAME/KEY: VARIANT
<222> LOCATION: (6)..(6)
<223> OTHER INFORMATION: Xaa = Ile, Val, or Leu

<400> SEQUENCE: 127

Xaa Xaa Tyr Xaa Xaa Xaa
1               5

<210> SEQ ID NO 128
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (2)..(3)
<223> OTHER INFORMATION: Xaa = Any Amino Acid
<220> FEATURE:
<221> NAME/KEY: VARIANT
<222> LOCATION: (4)..(4)
<223> OTHER INFORMATION: Xaa = Leu or Ile
<220> FEATURE:
<221> NAME/KEY: VARIANT
<222> LOCATION: (5)..(16)
<223> OTHER INFORMATION: Xaa = Any Amino Acid, and up to 6 of them can
      be present or absent
<220> FEATURE:
<221> NAME/KEY: VARIANT
<222> LOCATION: (18)..(19)
<223> OTHER INFORMATION: Xaa = Any Amino Acid
<220> FEATURE:
<221> NAME/KEY: VARIANT
<222> LOCATION: (20)..(20)
<223> OTHER INFORMATION: Xaa = Leu or Ile

<400> SEQUENCE: 128

Tyr Xaa Xaa Xaa Xaa Xaa Xaa Xaa Xaa Xaa Xaa Xaa Xaa Xaa Xaa Xaa
1               5                   10                  15

Tyr Xaa Xaa Xaa
            20

<210> SEQ ID NO 129
<211> LENGTH: 19
<212> TYPE: DNA
<213> ORGANISM: Artificial Sequence
<220> FEATURE:
<223> OTHER INFORMATION: Synthetic Construct

<400> SEQUENCE: 129
agctgggaag gtgtgcaca                                                19
```

```
<210> SEQ ID NO 130
<211> LENGTH: 21
<212> TYPE: DNA
<213> ORGANISM: Artificial Sequence
<220> FEATURE:
<223> OTHER INFORMATION: Synthetic Construct

<400> SEQUENCE: 130 ccatttgtc gttcactgcc a                                              21
```